(12) United States Patent
Kawahara et al.

(10) Patent No.: US 7,282,601 B2
(45) Date of Patent: Oct. 16, 2007

(54) DICARBOXYLIC DIESTER, PROCESS FOR PRODUCING THE SAME, AND REFRIGERATING MACHINE LUBRICATING OIL COMPRISING THE ESTER

(75) Inventors: Yasuyuki Kawahara, Uji (JP); Kouji Takahashi, Kyoto (JP); Makiko Takii, Uji (JP)

(73) Assignee: New Japan Chemical Co., Ltd., Kyoto-Shi (JP)

( * ) Notice: Subject to any disclaimer, the term of this patent is extended or adjusted under 35 U.S.C. 154(b) by 281 days.

(21) Appl. No.: 10/952,925

(22) Filed: Sep. 30, 2004

(65) Prior Publication Data

US 2005/0038283 A1    Feb. 17, 2005

Related U.S. Application Data

(62) Division of application No. 10/019,287, filed as application No. PCT/JP00/04838 on Jul. 19, 2000.

(30) Foreign Application Priority Data

| Jul. 19, 1999 | (JP) | ............................... 1999-204033 |
| Jul. 19, 1999 | (JP) | ............................... 1999-204034 |
| Apr. 3, 2000  | (JP) | ............................... 2000-100551 |

(51) Int. Cl.
*C07C 69/74* (2006.01)
*C07C 69/76* (2006.01)

(52) U.S. Cl. ................ 560/76; 560/128; 560/127

(58) Field of Classification Search ................ 560/76, 560/127, 128; 508/465, 484
See application file for complete search history.

(56) References Cited

U.S. PATENT DOCUMENTS

| 2,975,210 | A |   | 3/1961 | Raether et al. |
| 4,514,190 | A |   | 4/1985 | Cousineau et al. |
| 5,185,092 | A | * | 2/1993 | Fukuda et al. ............. 508/440 |
| 5,231,218 | A |   | 7/1993 | Summer, Jr. et al. ....... 560/127 |
| 5,342,533 | A |   | 8/1994 | Kondo et al. |
| 6,231,782 | B1 |  | 5/2001 | Shimomura et al. |

FOREIGN PATENT DOCUMENTS

| EP | 1 184 446  | 3/2002 |
| EP | 1 205 534  | 5/2002 |
| JP | 02-242888  | 9/1990 |
| JP | 03-033193  | 2/1991 |
| JP | 03-128991  | 5/1991 |
| JP | 03-200895  | 9/1991 |
| JP | 04-020597  | 1/1992 |
| JP | 4-226193   | 8/1992 |
| JP | 04-226193  | 8/1992 |
| JP | 6-25683    | 2/1994 |
| JP | 06-128578  | 5/1994 |
| JP | 7-233385   | 9/1995 |
| JP | 9-221690   | 8/1997 |
| JP | 10-130673  | 5/1998 |
| JP | 10-140170  | 5/1998 |
| JP | 2000-273477 | 10/2000 |
| JP | 2000-273479 | 10/2000 |
| WO | WO97/21792 | 6/1997 |

OTHER PUBLICATIONS

International Search Report dated Oct. 24, 2000.
Chinese Office Action with English Translation dated Jun. 18, 2004.
A Copy of International Search Report.
A copy of the European Office Communication for corresponding European Patent Application No. 00 94 6399 dated Jun. 15, 2005.

* cited by examiner

*Primary Examiner*—Taylor Victor Oh
(74) *Attorney, Agent, or Firm*—Kratz, Quintos & Hanson, LLP

(57) ABSTRACT

A diester represented by the formula

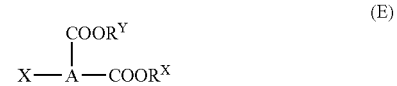

wherein A represents a cyclohexane ring, cyclohexene ring or benzene ring, X is H or methyl group, $R^X$ and $R^Y$ are the same or different and each is C3-C18 branched-chain alkyl group, C1-C18 straight-chain alkyl group, C2-C18 straight-chain alkenyl or C3-C18 cycloalkyl, provided that when A is a benzene ring, $R^X$ and $R^Y$ are different from each other and —$COOR^X$ and —$COOR^Y$ are attached to two adjacent carbon atoms of the benzene ring, and having the following properties:
1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less;
7) a volume resistivity of $1 \times 10^{11}$ Ω·cm or more,
8) a hydroxyl value of 3 mgKOH/g or less, and
9) a water content of 100 ppm or less,
a process for preparing the same and a refrigerator lubricating oil comprising the diester.

10 Claims, No Drawings

DICARBOXYLIC DIESTER, PROCESS FOR PRODUCING THE SAME, AND REFRIGERATING MACHINE LUBRICATING OIL COMPRISING THE ESTER

This application is a Divisional application of U.S. application Ser. No. 10/019,287, filed Jan. 2, 2002, which is a 371 of PCT/JP00/04838, filed on Jul. 19, 2000, which are hereby incorporated by reference.

FIELD OF THE INVENTION

The present invention relates to an alicyclic dicarboxylic acid diester suitable as a lubricating oil for a refrigerator and a process for preparing the same.

Furthermore, the present invention concerns with an alicyclic or aromatic adjacent dicarboxylic acid mixed diester prepared by a 2-step process, the ester being useful as a lubricating oil (hereinafter referred to as "refrigerator oil") for compressors in automotive air conditioners, refrigerators, room air conditioners, large-size industrial refrigerators or the like using hydrofluorocarbon refrigerants, a process for preparing the same and a refrigerator oil containing the ester.

The term "alicyclic or aromatic adjacent dicarboxylic acid mixed diester" used in this specification and claims refers to an alicyclic or aromatic dicarboxylic acid diester wherein the two ester groups thereof are attached to two adjacent carbon atoms of the alicyclic or aromatic group such as cyclohexane, cyclohexene or benzene, the two ester groups being different from each other.

PRIOR ART

In recent years, an attempt is going on to substitute a refrigerant such as HFC-134a which is a hydrofluorocarbon (HFC) for R11 or R12 which is a chloro-fluorocarbon (CFC) or R22 which is a hydrochloro-fluorocarbon (HCFC) to overcome the problems of ozone layer depletion and global warming. Now oxygen-containing synthetic oils have come into use as a refrigerator oil for HFC. Examples are polyol esters (JP-A-3-128991, JP-A-3-200895, etc.), polyvinyl ethers (JP-A-6-128578, etc.) and polyalkylene glycol (JP-A-2-242888, JP-A-3-33193, etc.).

WO 97/21792 discloses that an alicyclic dicarboxylic acid diester available as a new type of ester has a high hydrolysis stability and can be used as a metal cutting fluid or as a refrigerator oil.

More recently, however, the critical mind toward global warming has become intensified so that the development of efficient machinery is on the way to save energy in refrigerators for the purpose of reducing the emission level of carbon dioxide which causes global warming. On the other hand, since a CFC substitute itself (CFC and HCFC substitutes), used as a refrigerant, is one of global warming substances, it is desired to decrease the quantity of the refrigerant to be used. To improve the efficiency of machinery and to decrease the refrigerant consumption, a compact machinery may be a candidate for achieving the goals. In compact machinery, however, lubricating oils will be used unavoidably under severer conditions. Therefore, new refrigerator oils need to be improved over conventional oils in hydrolysis stability, heat stability, electrical insulating property, lubricity and the like. Yet new refrigerator oils which can meet these requirements have not been developed. Thus, there is a need for providing an alicyclic dicarboxylic acid diester which is suitable as a refrigerator oil and which has an improved performance.

Generally a refrigerator oil is selected considering whether it has a viscosity characteristic suitable for a particular apparatus to be used. For example, JIS-K-2211 classifies refrigerator oils into five categories. Thus, various refrigerator oils having different viscosities are necessary for different apparatuses and for different intended uses.

At the moment, polyol ester refrigerator oils are available for practical applications. Viscosity adjustment of such refrigerator oils is carried out by (1) mixing at least 2 kinds of polyol esters of different viscosities or by (2) providing a polyol mixed ester of the desired viscosity in a 1-step process using a mixture of at least two alcohols or acids as the starting materials for esterification, as disclosed, for example, in JP-A-3-200895 and JP-A-4-20597.

WO 97/21792 discloses, as mentioned above, that an alicyclic adjacent dicarboxylic acid ester available as a new type of ester has an excellent hydrolysis stability and can be used as a metal cutting fluid or as a refrigerator oil. JP-A-4-226193 describes an aromatic adjacent dicarboxylic acid ester has a high performance as a refrigerator oil.

DISCLOSURE OF THE INVENTION

In view of the foregoing, a first object of the present invention is to provide a process for preparing a dicarboxylic acid diester which is excellent in hydrolysis stability, heat stability, electrical insulating property, lubricity and the like.

Furthermore, the present inventors intensively investigated alicyclic dicarboxylic acid esters in an attempt to cope with the need for various viscosity grades of refrigerator oils, and found that when the viscosity adjustment is carried out by mixing at least two alicyclic adjacent dicarboxylic acid esters of different viscosities according to method (1) above, the obtained ester mixture may be inferior in stability, electrical insulating property, lubricity, miscibility with refrigerants, etc. due to the drawbacks of low-viscosity esters or high-viscosity esters. On the other hand, the inventors discovered that alicyclic adjacent dicarboxylic acid mixed diesters can cope with the need for refrigerator oils of various viscosity grades. However, when a mixed diester is prepared by method (2) above, the obtained diester is not satisfactory in stability, electrical insulating property, lubricity and the like when used under recent stricter conditions, because the quality of the mixed diester is low due to low reactivity in esterification.

In this situation, a second object of the present invention is to provide a process for preparing a mixed diester which, when used as a refrigerator oil, is easily adjustable to a wide range of viscosities and which is excellent in hydrolysis stability, heat stability, electrical insulating property and lubricity.

The present inventors conducted extensive research to achieve the foregoing objects and found that alicyclic dicarboxylic acid diesters or alicyclic or aromatic adjacent dicarboxylic acid mixed diesters having specific properties are outstanding in hydrolysis stability, heat stability, electrical insulating property, lubricity and the like.

The present invention provides an ester (or a refrigerator lubricating oil comprising said ester), said ester being selected from the group consisting of alicyclic or aromatic adjacent dicarboxylic acid diesters represented by the formula (E)

wherein A represents a cyclohexane ring, a cyclohexene ring or a benzene ring, X is a hydrogen atom or methyl, $R^X$ and $R^Y$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, with the proviso that when A is a benzene ring, $R^X$ and $R^Y$ are different from each other and the group —$COOR^X$ and the group —$COOR^Y$ are attached to two adjacent carbon atoms of the benzene ring, said ester (or said refrigerator lubricating oil) having the following properties:
1) a total acid number: 0.05 mgKOH/g or less;
2) a sulfated ash content: 10 ppm or less;
3) a sulfur content: 20 ppm or less;
4) a phosphorus content: 20 ppm or less;
5) a peroxide value: 1.0 meq/kg or less;
6) a carbonyl value: 10 or less;
7) a volume resistivity: $1\times10^{11}$ Ω·cm or more;
8) a hydroxyl value: 3 mgKOH/g or less, and
9) a water content: 100 ppm or less.

The alicyclic or aromatic dicarboxylic acid diesters represented by the formula (E) include alicyclic dicarboxylic acid diesters represented by the formula (1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, as well as alicyclic or aromatic adjacent dicarboxylic acid mixed diesters represented by the formula (4)

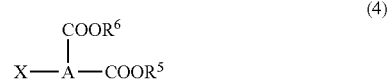

wherein A represents a cyclohexane ring, a cyclohexene ring or a benzene ring, X is a hydrogen atom or methyl, $R^5$ and $R^6$ are different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, and groups —$COOR^5$ and —$COOR^6$ are attached to two adjacent carbon atoms of the cyclohexane, cyclohexene or benzene ring represented by A.

According to the inventors' research, it was discovered that the alicyclic dicarboxylic acid diester represented by the formula (1) and the alicyclic or aromatic adjacent dicarboxylic acid mixed diester represented by the formula (4) prepared by specific processes have the properties 1) to 9) described above, and are excellent in hydrolysis stability, heat stability, electrical insulating property, lubricity and the like.

Especially, the present inventors conducted extensive research to achieve the foregoing first object and found that an ester prepared by esterification or ester interchange reaction using an alcohol having specific properties and a specific catalyst has an excellent hue and exhibits excellent electrical insulating property, heat stability and long-term hydrolysis stability when used as a refrigerator oil, and therefore can provide a refrigerator oil having remarkably high performance compared with conventional refrigerator oils. Based on these novel findings, the inventions described below in items 1 to 4 were completed.

Thus, the present invention relates to the following inventions.

Item 1. An alicyclic dicarboxylic acid diester (or a refrigerator lubricating oil comprising the alicyclic dicarboxylic acid diester), the ester being represented by the formula (1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms; the alicyclic dicarboxylic acid diester (or the refrigerator lubricating oil comprising the alicyclic dicarboxylic acid diester) having the following properties:
1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1\times10^{11}$ Ω·cm or more,
8) a hydroxyl value of 3 mgKOH/g or less, and
9) a water content of 100 ppm or less.

It is preferable that the alicyclic dicarboxylic acid diester (or the refrigerator lubricating oil comprising the alicyclic dicarboxylic acid diester) further has a hue of 50 or less (as measured according to JIS-K-0071-1-1998).

Item 2. A process for preparing alicyclic dicarboxylic acid diester represented by the formula (1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms; and having the following properties:
1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1 \times 10^{11}$ Ω·cm or more,
8) a hydroxyl value of 3 mgKOH/g or less, and
9) a water content of 100 ppm or less, the process comprising the steps of
(i) subjecting
a) an alicyclic dicarboxylic acid represented by the formula (2)

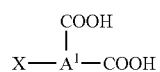
(2)

wherein $A^1$ and X are as defined above, or an anhydride thereof, and
b) an aliphatic monohydric alcohol having 1 to 18 carbon atoms or an alicyclic monohydric alcohol having 3 to 10 carbon atoms each having a peroxide value of 1.0 meq/kg or less to esterification reaction in the absence of a catalyst or in the presence of a sulfur-free and phosphorus-free catalyst, or subjecting
a') an alicyclic dicarboxylic acid diester represented by the formula (3)

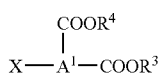
(3)

wherein $A^1$ and X are as defined above, $R^3$ and $R^4$ are the same or different and each is a branched-chain alkyl group having 3 or 4 carbon atoms or a straight-chain alkyl group having 1 to 4 carbon atoms, and
b') an aliphatic monohydric alcohol of 5 to 18 carbon atoms or an alicyclic monohydric alcohol of 3 to 10 carbon atoms each having a peroxide value of 1.0 meq/kg or less to ester interchange reaction in the absence of a catalyst or in the presence of a sulfur-free and phosphorus-free catalyst, to thereby obtain a reaction mixture containing the diester represented by the formula (1),
(ii) removing excess starting materials from the reaction mixture obtained in step (i) to thereby obtain the diester in a crude form,
(iii) neutralizing the crude diester obtained in step (ii) and washing the neutralized crude diester with water,
(iv) purifying the crude diester neutralized and washed with water in step (iii) by treatment with 1 to 4 kinds of adsorbents, and
(v) dehydrating the diester purified in step (iv).

Item 3. A refrigerator lubricating oil comprising the alicyclic dicarboxylic acid diester represented by the formula (1) and having properties 1)-9) according to item 1 above.

Item 4. A refrigerator lubricating oil comprising the alicyclic dicarboxylic acid diester represented by the formula (1) and having properties 1) to 9) and obtainable by the process according to item 2.

It is preferable that in the refrigerator lubricating oil of item 4, the alicyclic dicarboxylic acid diester represented by the formula (1) contained in said lubricating oil is an ester obtained by carrying out the esterification in an inert gas atmosphere or in an inert gas stream.

In the specification, the inventions as defined above in Items 1 to 4 and the inventions relating to the alicyclic dicarboxylic acid diesters of the formula (1) are referred to as "embodiment I".

Furthermore, the present inventors conducted intensive investigations to achieve said second object using the foregoing alicyclic adjacent dicarboxylic acid mixed diester represented by the formula (4) as an refrigerator oil. We discovered that when a 2-step esterification process is carried out in preparing the alicyclic adjacent dicarboxylic acid mixed diester, a high-quality mixed diester can be produced under mild conditions and that when the obtained mixed diester is used as a refrigerator oil, it can be easily adjusted to a wide range of viscosities and it is excellent in hydrolysis stability, heat stability, electrical insulating property and lubricity. Moreover, the present inventors found that when this technique is applied for preparing the aromatic adjacent dicarboxylic acid mixed diester, the same effects can be produced. After carrying out further investigation, the inventors completed the inventions as defined in Items 5 to 9 to be described below.

Item 5. An alicyclic or aromatic adjacent dicarboxylic acid mixed diester (or a refrigerator lubricating oil comprising said alicyclic or aromatic adjacent dicarboxylic acid mixed diester) represented by the formula (4)

(4)

wherein A represents a cyclohexane ring, a cyclohexene ring or a benzene ring, X is a hydrogen atom or methyl, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, and group —COOR$^5$ and group —COOR$^6$ are attached to two adjacent carbon atoms of the cyclohexane, cyclohexene or benzene ring, the ester (or the refrigerator lubricating oil) having the following properties:
1) a total acid number: 0.05 mgKOH/g or less;
2) a sulfated ash content: 10 ppm or less;
3) a sulfur content: 20 ppm or less;
4) a phosphorus content: 20 ppm or less;
5) a peroxide value: 1.0 meq/kg or less;
6) a carbonyl value: 10 or less;
7) a volume resistivity: $1 \times 10^{11}$ Ω·cm or more;
8) a hydroxyl value: 3 mgKOH/g or less; and
9) a water content: 100 ppm or less.

Item 6. An ester mixture of (1) an alicyclic or aromatic adjacent dicarboxylic acid di(lower alkyl)ester represented by the formula (7)

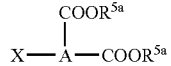
(7)

wherein A represents a cyclohexane ring, a cyclohexene ring or a benzene ring, X is a hydrogen atom or methyl, and $R^{5a}$ is a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and the two —$COOR^{5a}$ groups are the same and attached to two adjacent carbon atoms of the cyclohexane, cyclohexene or benzene ring represented by A;

(2) an alicyclic or aromatic adjacent dicarboxylic acid mixed diester represented by the formula (4a)

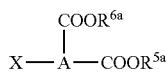
(4a)

wherein A and X are as defined in the formula (7), and $R^{5a}$ and $R^{6a}$ are different from each other and $R^{5a}$ is as defined in the formula (7), and $R^{6a}$ is a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and the group —$COOR^{5a}$ and the group —$COOR^{6a}$ are attached to two adjacent carbon atoms of the cyclohexane, cyclohexene or benzene ring represented by A, and (3) an alicyclic or aromatic adjacent dicarboxylic acid di(higher alkyl)ester represented by the formula (8)

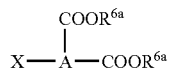
(8)

wherein A, X and $R^{6a}$ are as defined in the formula (4a), and the two —$COOR^{6a}$ groups are the same and attached to two adjacent carbon atoms of the cyclohexane, cyclohexene or benzene ring represented by A, the ester mixture having the following properties:

1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1\times10^{11}$ Ω·cm or more,
8) a hydroxyl value of 3 mgKOH/g or less, and
9) a water content of 100 ppm or less.

Item 7. A process for preparing an alicyclic or aromatic adjacent dicarboxylic acid mixed diester or an ester mixture, wherein the alicyclic or aromatic adjacent dicarboxylic acid mixed diester is represented by the formula (4)

(4)

wherein A represents a cyclohexane ring, a cyclohexene ring or a benzene ring, X is a hydrogen atom or methyl, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms (particularly, $R^5$ is a straight-chain alkyl group having 1 to 5 carbon atoms or a branched-chain alkyl group having 3 to 5 carbon atoms, $R^6$ is a straight-chain or branched-chain alkyl group having 6 to 11 carbon atoms), and the group —$COOR^5$ and the group —$COOR^6$ are attached to two adjacent carbon atoms of the cyclohexane, cyclohexene or benzene ring represented by A; and said ester mixture is a mixture of (1) an alicyclic or aromatic adjacent dicarboxylic acid di(lower alkyl)ester represented by the formula (7)

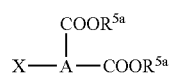
(7)

wherein A and X are as defined in the formula (4), and $R^{5a}$ represents a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and the two —$COOR^{5a}$ groups are the same and attached to two adjacent carbon atoms of the cyclohexane, cyclohexene or benzene ring represented by A, (2) an alicyclic or aromatic adjacent dicarboxylic acid mixed diester represented by the formula (4a)

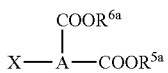
(4a)

wherein A and X are as defined in the formula (7), and $R^{5a}$ and $R^{6a}$ are different from each other and $R^{5a}$ is as defined above, and $R^{6a}$ is a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and the group —$COOR^{5a}$ and the group —$COOR^{6a}$ are attached to two adjacent carbon atoms of the cyclohexane, cyclohexene or benzene ring represented by A, and (3) an alicyclic or aromatic adjacent dicarboxylic acid di(higher alkyl)ester represented by the formula (8)

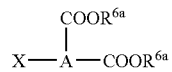
(8)

wherein A, X and $R^{6a}$ are as defined in the formula (4a), and the two —$COOR^{6a}$ groups are the same and attached to two adjacent carbon atoms of the cyclohexane, cyclohexene or benzene ring represented by A, and wherein the alicyclic or aromatic adjacent dicarboxylic acid diester or the ester mixture has the following properties:
1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1 \times 10^{11}$ Ω·cm or more,
8) a hydroxyl value of 3 mgKOH/g or less, and
9) a water content of 100 ppm or less, the process comprising the steps of
(i) (a) subjecting an alicyclic or aromatic adjacent dicarboxylic acid anhydride represented by the formula (5s)

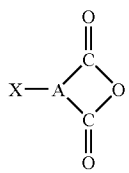
(5s)

wherein A and X are as defined above and "alcohol component 1" (namely, a single alcohol or alcohol mixture comprising a monohydric alcohol having 1 to 5 carbon atoms (P) and a monohydric alcohol having 6 to 18 carbon atoms (Q) wherein (P):(Q) is 0.1:99.9 to 100:0 (molar ratio)) to esterification reaction to thereby give an alicyclic or aromatic adjacent dicarboxylic acid monoester represented by the formula (5)

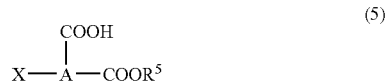
(5)

wherein A, X and $R^5$ are as defined above, and the group —COOR$^5$ and the group —COOH are attached to two adjacent carbon atoms of the cyclohexane, cyclohexene or benzene ring represented by A,
(b) subjecting the alicyclic or aromatic adjacent dicarboxylic acid monoester represented by the formula (5) obtained in step (a) and "alcohol component 2" (namely, a single alcohol or alcohol mixture comprising a monohydric alcohol having 1 to 5 carbon atoms (S) and a monohydric alcohol having 6 to 18 carbon atoms (T) wherein (S):(T) is 0:100 to 99.9:0.1 (molar ratio)) to a further esterification reaction in the absence of a catalyst or in the presence of a sulfur-free and phosphorus-free catalyst
to thereby give a reaction mixture containing said ester mixture of (1) the alicyclic or aromatic adjacent dicarboxylic acid di(lower alkyl)ester represented by the formula (7), (2) the alicyclic or aromatic adjacent dicarboxylic acid mixed diester represented by the formula (4a), and (3) the alicyclic or aromatic adjacent dicarboxylic acid di(higher alkyl)ester represented by the formula (8),
(ii) removing excess starting materials from the reaction mixture obtained in step (i) to thereby obtain the ester mixture in a crude form, (iii) neutralizing the crude diester obtained in step (ii) and washing the neutralized crude diester with water,
(iv) purifying the crude diester neutralized and washed with water in step (iii) by treatment with 1 to 4 kinds of adsorbents,
(v) dehydrating the diester purified in step (iv) to thereby give the ester mixture having the properties 1) to 9), and if desired,
(vi) separating the aromatic adjacent dicarboxylic acid mixed diester-mixture represented by the formula (4a) from the obtained ester mixture to thereby give the alicyclic or aromatic adjacent dicarboxylic acid mixed diester represented by the formula (4).

Item 8. A refrigerator lubricating oil comprising the alicyclic or aromatic adjacent dicarboxylic acid mixed diester represented by the formula (4) having the properties 1) to 9) of Item 5 above or the ester mixture having properties 1) to 9) of Item 6 above.

Item 9. A refrigerator lubricating oil comprising the alicyclic or aromatic adjacent dicarboxylic acid mixed diester represented by the formula (4) having properties 1) to 9) or the ester mixture having properties 1) to 9), which is obtainable by the process of Item 7.

It is preferable that in the refrigerator lubricating oil of item 9, the alicyclic or aromatic adjacent dicarboxylic acid mixed diester or the ester mixture represented by the formula (4) contained in said lubricating oil is the ester prepared by carrying out the esterification reactions in steps (a) and (b) in an inert gas atmosphere or in an inert gas stream.

In the specification, the inventions as defined above in Items 5 to 9 and the inventions relating to the process for preparing the above alicyclic or aromatic adjacent dicarboxylic acid mixed diester and the refrigerator oil containing said mixed diester are referred to as "embodiment II".

Described below are the esters of embodiment I, processes for preparing the same, the esters of embodiment II, processes for preparing the same, methods for purification of esters according to embodiments I and II, and then lubricating oils for refrigerators (hereinafter referred to as "refrigerator oils") which contain these esters.

Esters of Embodiment I and Process for Preparation Thereof

Alicyclic Dicarboxylic Acid Diester Represented by the Formula (1)

The alicyclic dicarboxylic acid diester represented by the formula (1) according to the invention (hereinafter sometimes called "present ester")

(1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, can be prepared by esterifying a) an acid component and b) an alcohol component in the conventional manner, preferably in an atmosphere of inert gas such as nitrogen in the absence of a catalyst or in the presence of a sulfur-free and phosphorus-free catalyst with stirring and heating.

The acid component as component a) for use in the esterification includes the alicyclic dicarboxylic acid represented by the formula (2) or an anhydride thereof, or an alicyclic dicarboxylic acid $C_{1-4}$ lower alkyl diester represented by the formula (3).

The alcohol component as component b) for use in the esterification includes an aliphatic monohydric alcohol having 1 to 18 carbon atoms or an alicyclic monohydric alcohol having 3 to 10 carbon atoms, each having a peroxide value of 1.0 meq/kg or less, and is represented by the formula $R^1$—OH or $R^2$—OH wherein $R^1$ and $R^2$ are as define above.

Especially, 1) when the alicyclic dicarboxylic acid represented by the formula (2) or an acid anhydride thereof is used as the acid component, it is preferable to use an aliphatic monohydric alcohol having 1 to 18 carbon atoms or an alicyclic monohydric alcohol having 3 to 10 carbon atoms, each having a peroxide value of 1.0 meq/kg or less, and 2) when the alicyclic dicarboxylic acid di($C_1$-$C_4$) lower alkyl diester represented by the formula (3) is used as the acid component, it is preferable to use an aliphatic monohydric alcohol having 5 to 18 carbon atoms or an alicyclic monohydric alcohol having 3 to 10 carbon atoms, each having a peroxide value of 1.0 meq/kg or less.

The symbol $A^1$ in the invention represents a cyclohexane ring or a cyclohexene ring. When $A^1$ is a cyclohexene ring, the position of double bond may be any position relative to the ester groups, and is not limited. X is a hydrogen atom or methyl. When X is methyl, the substitution position on the cyclohexane ring or cyclohexene ring of methyl is not limited. There is also no restriction on the substitution positions of two ester groups bonded to the cyclohexane ring or cyclohexene ring represented by $A^1$.

Among the diesters represented by the formula (1), preferred are those wherein $A^1$ is a cyclohexane ring and X is hydrogen, those wherein $A^1$ is a cyclohexene ring and X is hydrogen, those wherein $A^1$ is a cyclohexene ring and X is methyl. Further, while the positions of the two ester groups may be any of 1,2-positions, 1,3-positions and 1,4-positions of cyclohexane ring or cyclohexene ring, 1,2-position is preferred in view of hydrolysis stability of the diester of the formula (1).

Especially, cyclohexane-1,2-diesters, 3-cyclohexene-1,2-diesters, 4-cyclohexene-1,2-diesters and the like are recommended.

In the present invention, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms.

Examples of the branched-chain alkyl group having 3 to 18 carbon atoms are isopropyl, isobutyl, sec-butyl, isopentyl, isohexyl, 2-methylhexyl, 2-methylheptyl, isoheptyl, 2-ethylhexyl, 2-octyl, isooctyl, isononyl, 3,5,5-trimethylhexyl, 2,6-dimethyl-4-heptyl, isodecyl, isoundecyl, isododecyl, isotridecyl, isotetradecyl, isopentadecyl, isohexadecyl, isoheptadecyl, isooctadecyl, etc.

Examples of the straight-chain alkyl group having 1 to 18 carbon atoms are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, etc.

Examples of the straight-chain alkenyl group having 2 to 18 carbon atoms are 2-hexenyl, 5-hexenyl, 2-heptenyl, 6-heptenyl, 2-octenyl, 8-nonenyl, 2-decenyl, 2-undecenyl, 10-undecenyl, 11-dodecenyl, 12-tridecenyl, 2-tetradecenyl, 2-pentadecenyl, 2-hexadecenyl, 15-hexadecenyl, 2-heptadecenyl, 2-octadecenyl, 9-octadecenyl, etc.

Examples of the cycloalkyl group having 3 to 10 carbon atoms are cyclopentyl, cyclohexyl, methylcyclohexyl, dimethylcyclohexyl, cycloheptyl, cyclooctyl, etc.

Examples of the alicyclic dicarboxylic acid diester represented by the formula (1) obtained in the present invention are dimethyl 1,2-cyclo-hexanedicarboxylate, diethyl 1,2-cyclohexanedicarboxylate, di(n-propyl) 1,2-cyclohexanedicarboxylate, di(n-butyl) 1,2-cyclohexanedicarboxylate, di(n-pentyl) 1,2-cyclohexanedicarboxylate, di(n-hexyl) 1,2-cyclohexanedicarboxylate, di(n-heptyl) 1,2-cyclohexanedicarboxylate, di(n-octyl) 1,2-cyclohexanedicarboxylate, di(n-nonyl) 1,2-cyclohexanedicarboxylate, di(n-decyl) 1,2-cyclohexanedicarboxylate, di(n-undecyl) 1,2-cyclohexanedicarboxylate, di(n-dodecyl) 1,2-cyclohexanedicarboxylate, di(n-tridecyl) 1,2-cyclohexanedicarboxylate, di(n-tetradecyl) 1,2-cyclohexanedicarboxylate, di(n-pentadecyl) 1,2-cyclohexanedicarboxylate, di(n-hexadecyl) 1,2-cyclohexanedicarboxylate, di(n-octadecyl) 1,2-cyclohexanedicarboxylate, dimethyl 4-cyclohexene-1,2-dicarboxylate, diethyl 4-cyclohexene-1,2-dicarboxylate, di(n-propyl)4-cyclohexene-1,2-dicarboxylate, di(n-butyl) 4-cyclohexene-1,2-dicarboxylate, di(n-pentyl) 4-cyclohexene-1,2-dicarboxylate, di(n-hexyl) 4-cyclohexene-1,2-dicarboxylate, di(n-heptyl) 4-cyclohexene-1,2-dicarboxylate, di(n-octyl) 4-cyclohexene-1,2-dicarboxylate, di(n-nonyl) 4-cyclohexene-1,2-dicarboxylate, di(n-decyl) 4-cyclohexene-1,2-dicarboxylate, di(n-undecyl) 4-cyclohexene-1,2-dicarboxylate, di(n-dodecyl) 4-cyclohexene-1,2-dicarboxylate, di(n-tridecyl) 4-cyclohexene-1,2-dicarboxylate, di(n-tetradecyl) 4-cyclohexene-1,2-dicarboxylate, di(n-pentadecyl) 4-cyclohexene-1,2-dicarboxylate, di(n-hexadecyl) 4-cyclohexene-1,2-dicarboxylate, di(n-octadecyl) 4-cyclohexene-1,2-dicarboxylate, dimethyl 3-methyl-1,2-cyclohexanedicarboxylate, diethyl 3-methyl-1,2-cyclohexanedicarboxylate, di(n-propyl) 3-methyl-1,2-cyclohexanedicarboxylate, di(n-butyl) 3-methyl-1,2-cyclohexanedicarboxylate, di(n-pentyl) 3-methyl-1,2-cyclohexanedicarboxylate, di(n-hexyl) 3-methyl-,2-cyclohexanedicarboxylate, di(n-heptyl) 3-methyl-1,2-cyclohexanedicarboxylate, di(n-octyl) 3-methyl-1,2-cyclohexanedicarboxylate, di(n-nonyl) 3-methyl-1,2-cyclohexanedicarboxylate, di(n-decyl) 3-methyl-1,2-cyclohexanedicarboxylate, di(n-undecyl) 3-methyl-1,2-cyclohexanedicarboxylate, di(n-dodecyl) 3-methyl-1,2-cyclohexanedicarboxylate, di(n-tridecyl) 3-methyl-1,2-cyclohexanedicarboxylate, di(n-tetradecyl) 3-methyl-1,2-cyclohexanedicarboxylate, di(n-pentadecyl) 3-methyl-1,2-cyclohexanedicarboxylate, di(n-hexadecyl) 3-methyl-1,2-cyclohexanedicarboxylate, di(n-octadecyl) 3-methyl-1,2-cyclohexanedicarboxylate, dimethyl 4-methyl-1,2-cyclohexanedicarboxylate, diethyl 4-methyl-1,2-cyclohexanedicarboxylate, di(n-propyl) 4-methyl-1,2-cyclohexanedicarboxylate, di(n-butyl) 4-methyl-1,2-cyclohexanedicarboxylate, di(n-pentyl) 4-methyl-1,2-cyclohexanedicarboxylate, di(n-hexyl) 4-methyl-1,2-cyclohexanedicarboxylate, di(n-heptyl) 4-methyl-1,2-cyclohexanedicarboxylate, di(n-octyl) 4-methyl-1,2-cyclohexanedicarboxylate, di(n-nonyl) 4-methyl-1,2-cyclohexanedicarboxylate, di(n-decyl) 4-methyl-1,2-cyclohexanedicarboxylate, di(n-undecyl) 4-methyl-1,2-cyclohexanedicarboxylate, di(n-dodecyl) 4-methyl-1,2- cyclohexanedicarboxylate, di(n-tridecyl) 4-methyl-1,2-cyclohexanedicarboxylate, di(n-tetradecyl) 4-methyl-1,2-cyclohexanedicarboxylate, di(n-pentadecyl) 4-methyl-1,2-cyclohexanedicarboxylate, di(n-hexadecyl) 4-methyl-1,2-cyclohexanedicarboxylate, di(n-octadecyl) 4-methyl-1,2-cyclohexanedicarboxylate, dimethyl 3-methyl-4-cyclohexene-1,2-dicarboxylate, diethyl 3-methyl-4-cyclohexene-1,2-dicarboxylate, di(n-propyl) 3-methyl-4-cyclohexene-1,2-dicarboxylate, di(n-butyl) 3-methyl-4-cyclohexene-1,2-dicarboxylate, di(n-pentyl) 3-methyl-4-cyclohexene-1,2-dicarboxylate, di(n-hexyl) 3-methyl-4-cyclohexene-1,2-dicarboxylate, di(n-heptyl) 3-methyl-4-cyclohexene-1,2-dicarboxylate, di(n-octyl) 3-methyl-4-cyclohexene-1,2-dicarboxylate, di(n-nonyl) 3-methyl-4-cyclohexene-1,2-dicarboxylate, di(n-decyl) 3-methyl-4-cyclohexene-1,2-dicarboxylate, di(n-undecyl) 3-methyl-4-cyclohexene-1,2-dicarboxylate, di(n-dodecyl) 3-methyl-4-cyclohexene-1,2-dicarboxylate, di(n-tridecyl) 3-methyl-4-cyclohexene-1,2-dicarboxylate, di(n-tetradecyl) 3-methyl-4-cyclohexene-1,2-dicarboxylate, di(n-pentadecyl) 3-methyl-4-cyclohexene-1,2-dicarboxylate, di(n-hexadecyl) 3-methyl-4-cyclohexene-1,2-dicarboxylate, di(n-octadecyl) 3-methyl-4-cyclohexene-1,2-dicarboxylate, dimethyl 4-methyl-4-cyclohexene-1,2-dicarboxylate, diethyl 4-methyl-4-cyclohexene-1,2-dicarboxylate, di(n-propyl) 4-methyl-4-cyclohexene-1,2-dicarboxylate, di(n-butyl) 4-methyl-4-cyclohexene-1,2-dicarboxylate, di(n-pentyl) 4-methyl-4-cyclohexene-1,2-dicarboxylate, di(n-hexyl) 4-methyl-4-cyclohexene-1,2-dicarboxylate, di(n-heptyl) 4-methyl-4-cyclohexene-1,2-dicarboxylate, di(n-octyl) 4-methyl-4-cyclohexene-1,2-dicarboxylate, di(n-nonyl) 4-methyl-4-cyclohexene-1,2-dicarboxylate, di(n-decyl) 4-methyl-4-cyclohexene-1,2-dicarboxylate, di(n-undecyl) 4-methyl-4-cyclohexene-1,2-dicarboxylate, di(n-dodecyl) 4-methyl-4-cyclohexene-1,2-dicarboxylate, di(n-tridecyl) 4-methyl-4-cyclohexene-1,2-dicarboxylate, di-(n-tetradecyl) 4-methyl-4-cyclohexene-1,2-dicarboxylate, di(n-pentadecyl) 4-methyl-4-cyclohexene-1,2-dicarboxylate, di(n-hexadecyl) 4-methyl-4-cyclohexene-1,2-dicarboxylate, di(n-octadecyl) 4-methyl-4-cyclohexene-1,2-dicarboxylate, diisopropyl 1,2-cyclohexanedicarboxylate, diisobutyl 1,2-cyclohexanedicarboxylate, di(sec-butyl) 1,2-cyclohexanedicarboxylate, dicyclohexyl 1,2-cyclohexanedicarboxylate, diisoheptyl 1,2-cyclohexanedicarboxylate, di(2-ethylhexyl) 1,2-cyclohexanedicarboxylate, diisononyl 1,2-cyclohexanedicarboxylate, di(3,5,5-trimethylhexyl) 1,2-cyclohexanedicarboxylate, di(2,6-dimethyl-4-heptyl) 1,2-cyclohexanedicarboxylate, diisodecyl 1,2-cyclohexanedicarboxylate, diisoundecyl 1,2-cyclohexanedicarboxylate, diisotridecyl 1,2-cyclohexanedicarboxylate, diisopentadecyl 1,2-cyclohexanedicarboxylate, diisooctadecyl 1,2-cyclohexanedicarboxylate, diisopropyl 4-cyclohexene-1,2-dicarboxylate, diisobutyl 4-cyclohexene-1,2-dicarboxylate, di(sec-butyl) 4-cyclohexene-1,2-dicarboxylate, dicyclohexyl 4-cyclohexene-1,2-dicarboxylate, diisoheptyl 4-cyclohexene-1,2-dicarboxylate, di(2-ethylhexyl) 4-cyclohexene-1,2-dicarboxylate, diisononyl 4-cyclohexene-1,2-dicarboxylate, di(3,5,5-trimethylhexyl) 4-cyclohexene-1,2-dicarboxylate, di(2,6-dimethyl-4-heptyl) 4-cyclohexene-1,2-dicarboxylate, diisodecyl 4-cyclohexene-1,2-dicarboxylate, diisoundecyl 4-cyclohexene-1,2-dicarboxylate, diisotridecyl 4-cyclohexene-1,2-dicarboxylate, diisopentadecyl 4-cyclohexene-1,2-dicarboxylate, diisooctadecyl 4-cyclohexene-1,2-dicarboxylate, diisopropyl 3-methyl-1,2-cyclohexanedicarboxylate, diisobutyl 3-methyl-1,2-cyclohexanedicarboxylate, di(sec-butyl) 3-methyl-1,2-cyclohexanedicarboxylate, dicyclohexyl 3-methyl-1,2-cyclohexanedicarboxylate, diisoheptyl 3-methyl-1,2-cyclohexanedicarboxylate, di(2-ethylhexyl) 3-methyl-1,2-cyclohexanedicarboxylate, diisononyl 3-methyl-1,2-cyclohexanedicarboxylate, di(3,5,5-trimethylhexyl) 3-methyl-1,2-cyclohexanedicarboxylate, di(2,6-dimethyl-4-heptyl) 3-methyl-1,2-cyclohexanedicarboxylate, diisodecyl 3-methyl-1,2-cyclohexanedicarboxylate, diisoundecyl 3-methyl-1,2-cyclohexanedicarboxylate, diisotridecyl 3-methyl-1,2-cyclohexanedicarboxylate, diisopentadecyl 3-methyl-1,2-cyclohexanedicarboxylate, diisooctadecyl 3-methyl-1,2-cyclohexanedicarboxylate, diisopropyl 4-methyl-1,2-cyclohexanedicarboxylate, diisobutyl 4-methyl-1,2-cyclohexanedicarboxylate, di(sec-butyl) 4-methyl-1,2-cyclohexanedicarboxylate, dicyclohexyl 4-methyl-1,2-cyclohexanedicarboxylate, diisoheptyl 4-methyl-1,2-cyclohexanedicarboxylate, di(2-ethylhexyl) 4-methyl-1,2-cyclohexanedicarboxylate, diisononyl 4-methyl-1,2-cyclohexanedicarboxylate, di(3,5,5-trimethylhexyl) 4-methyl-1,2-cyclohexanedicarboxylate, di(2,6-dimethyl-4-heptyl) 4-methyl-1,2-cyclohexanedicarboxylate, diisodecyl 4-methyl-1,2-cyclohexanedicarboxylate, diisoundecyl 4-methyl-1,2-cyclohexanedicarboxylate, diisotridecyl 4-methyl-1,2-cyclohexanedicarboxylate, diisopentadecyl 4-methyl-1,2-cyclohexanedicarboxylate, diisooctadecyl 4-methyl-1,2-cyclohexanedicarboxylate, diisopropyl 3-methyl-4-cyclohexene-1,2-dicarboxylate, diisobutyl 3-methyl-4-cyclohexene-1,2-dicarboxylate, di(sec-butyl) 3-methyl-4-cyclohexene-1,2-dicarboxylate, dicyclohexyl 3-methyl-4-cyclohexene-1,2-dicarboxylate, diisoheptyl 3-methyl-4-cyclohexene-1,2-dicarboxylate, di(2-ethylhexyl) 3-methyl-4-cyclohexene-1,2-dicarboxylate, diisononyl 3-methyl-4-cyclohexene-1,2-dicarboxylate, di(3,5,5-trimethylhexyl) 3-methyl-4-cyclohexene-1,2-dicarboxylate, di(2,6-dimethyl-4-heptyl) 3-methyl-4-cyclohexene-1,2-dicarboxylate, diisodecyl 3-methyl-4-cyclohexene-1,2-dicarboxylate, diisoundecyl 3-methyl-4-cyclohexene-1,2-dicarboxylate, diisotridecyl 3-methyl-4-cyclohexene-1,2-dicarboxylate, diisopentadecyl 3-methyl-4-cyclohexene-1,2-dicarboxylate, diisooctadecyl 3-methyl-4-cyclohexene-1,2-dicarboxylate, diisopropyl 4-methyl-4-cyclohexene-1,2-dicarboxylate, diisobutyl 4-methyl-4-cyclohexene-1,2-dicarboxylate, di(sec-butyl) 4-methyl-4-cyclohexene-1,2-dicarboxylate, dicyclohexyl 4-methyl-4-cyclohexene-1,2-dicarboxylate, diisoheptyl 4-methyl-4-cyclohexene-1,2-dicarboxylate, di(2-ethylhexyl) 4-methyl-4-cyclohexene-1,2-dicarboxylate, diisononyl 4-methyl-4-cyclohexene-1,2-dicarboxylate, di(3,5,5-trimethylhexyl) 4-methyl-4-cyclohexene-1,2-dicarboxylate, di(2,6-dimethyl-4-heptyl) 4-methyl-4-cyclohexene-1,2-dicarboxylate, diisodecyl 4-methyl-4-cyclohexene-1,2-dicarboxylate, diisoundecyl 4-methyl-4-cyclohexene-1,2-dicarboxylate, diisotridecyl 4-methyl-4-cyclohexene-1,2-dicarboxylate, diisopentadecyl 4-methyl-4-cyclohexene-1,2-dicarboxylate, diisooctadecyl 4-methyl-4-cyclohexene-1,2-dicarboxylate, etc.

Among the alicyclic dicarboxylic acid diesters represented by the formula (1), particularly preferred are those wherein $R^1$ and $R^2$ each represents a straight-chain or branched-chain alkyl group having 3 to 11 carbon atoms and $A^1$ represents a cyclohexane ring or a cyclohexene ring, and X is a hydrogen atom.

Preferred alicyclic dicarboxylic acid diesters include di(n-propyl) 1,2-cyclohexane-dicarboxylate, di(n-butyl) 1,2-cyclohexanedicarboxylate, di(n-pentyl) 1,2-cyclohexanedicarboxylate, di(n-hexyl) 1,2-cyclohexanedicarboxylate, di(n-heptyl) 1,2-cyclohexanedicarboxylate, di(n-octyl) 1,2- cyclohexanedicarboxylate, di(n-nonyl) 1,2-cyclohexanedicarboxylate, di(n-decyl) 1,2-cyclohexanedicarboxylate, di(n-undecyl) 1,2-cyclohexanedicarboxylate, diisopropyl 1,2-cyclohexanedicarboxylate, diisobutyl 1,2-cyclohexanedicarboxylate, di(sec-butyl) 1,2-cyclohexanedicarboxylate, dicyclohexyl 1,2-cyclohexanedicarboxylate, diisoheptyl 1,2-cyclohexanedicarboxylate, di(2-ethlyhexyl) 1,2-cyclohexanedicarboxylate, diisononyl 1,2-cyclohexanedicarboxylate, di(3,5,5-trimethylhexyl) 1,2-cyclohexanedicarboxylate, di(2,6-dimethyl-4-heptyl) 1,2-cyclohexanedicarboxylate, diisodecyl 1,2-cyclohexanedicarboxylate, diisoundecyl 1,2-cyclohexanedicarboxylate, di(n-propyl) 4-cyclohexene-1,2-dicarboxylate, di(n-butyl) 4-cyclohexene-1,2-dicarboxylate, di(n-pentyl) 4-cyclohexene-1,2-dicarboxylate, di(n-hexyl) 4-cyclohexene-1,2-dicarboxylate, di(n-heptyl) 4-cyclohexene-1,2-dicarboxylate, di(n-octyl) 4-cyclohexene-1,2-dicarboxylate, di(n-nonyl) 4-cyclohexene-1,2-dicarboxylate, di(n-decyl) 4-cyclohexene-1,2-dicarboxylate, di(n-undecyl) 4-cyclohexene-1,2-dicarboxylate, diisopropyl 4-cyclohexene-1,2-dicarboxylate, diisobutyl 4-cyclohexene-1,2-dicarboxylate, di(sec-butyl) 4-cyclohexene-1,2-dicarboxylate, dicyclohexyl 4-cyclohexene-1,2-dicarboxylate, diisoheptyl 4-cyclohexene-1,2-dicarboxylate, di(2-ethylhexyl) 4-cyclohexene-1,2-dicarboxylate, diisononyl 4-cyclohexene-1,2-dicarboxylate, di(3,5,5-trimethylhexyl) 4-cyclohexene-1,2-dicarboxylate, di(2,6-dimethyl-4-heptyl) 4-cyclohexene-1,2-dicarboxylate, diisodecyl 4-cyclohexene-1,2-dicarboxylate, diisoundecyl 4-cyclohexene-1,2-dicarboxylate, etc.

The alicyclic dicarboxylic acid diesters represented by the formula (1) may include position isomers ascribed to ester groups. For example, 4-cyclohexene-1,2-dicarboxylic acid diester may be an isomer depending on whether two ester groups are present in equatorial or axial positions. Specifically, the diester is a cis isomer when one of its two ester groups is in the equatorial position and the other is present in the axial position. The diester is a trans isomer when both of its two ester groups are present in the equatorial position or in the axial position. Both isomers can be used for use in a refrigerator oil.

When esterification temperature is set to higher than 210° C. and up to about 230° C. in the preparation of the alicyclic dicarboxylic acid diester, the esterification tends to predominantly give a trans isomer, whereas when esterification temperature is set at about 100 to about 210° C., the esterification tends to predominantly give a cis isomer.

A cis-form ester can be isomerized to a trans-form ester. Isomerization can be performed according to the method disclosed, for example, in U.S. Pat. No. 5,231,218.

Process for Preparing an Ester of Embodiment I

In esterification of the alicyclic dicarboxylic acid of the formula (2) as component a) in item 2 and in ester interchange reaction of the alicyclic dicarboxylic acid diester of the formula (3) as component a') in item 2, the same alcohol component is used as component b), b') under the same reaction conditions. In the following description, therefore, the esterification and the ester interchange reaction are collectively referred to as "esterification" and the reaction conditions thereof are described.

Alicyclic Dicarboxylic Acid of the Formula (2)

Examples of the alicyclic dicarboxylic acid of the formula (2) are cyclohexanedicarboxylic acid, cyclohexenedicarboxylic acid, methyl-substituted cyclohexanedicarboxylic acid and methyl-substituted cyclohexenedicarboxylic acid. Further, anhydrides thereof can be also used, and two or more species of such compounds can be used as mixed. The substitution positions of its carboxyl groups may be any positions on the cyclohexane ring or cyclohexene ring without specific limitation. The position of the double bond in cyclohexenedicarboxylic acid may be any position relative to the carboxyl groups without specific limitation.

However, with a view to prepare a diester of the formula (1) excellent in hydrolysis stability, it is preferable that the dicarboxylic acid is one having carboxyl groups in 1,2-positions of the cyclohexane or cyclohexene ring. In the case of cyclohexene ring, preferably the double bond exists between the 4-position and 5-position relative to the carboxyl groups at 1,2-positions.

More specific examples of the alicyclic dicarboxylic acid of the formula (2) are 1,2-cyclohexanedicarboxylic acid, 4-cyclohexene-1,2-dicarboxylic acid, 1-cyclohexene-1,2-dicarboxylic acid, 1,3-cyclohexanedicarboxylic acid, 1,4-cyclohexanedicarboxylic acid, 3-methyl-1,2-cyclohexanedicarboxylic acid, 4-methyl-1,2-cyclohexanedicarboxylic acid, 3-methyl-4-cyclohexene-1,2-dicarboxylic acid and 4-methyl-4-cyclohexene-1,2-dicarboxylic acid, and the anhydrides thereof are also usable.

Of these, 1,2-cyclohexanedicarboxylic acid, 4-cyclohexene-1,2-dicarboxylic acid, 1-cyclohexene-1,2-dicarboxylic acid, 3-methyl-1,2-cyclohexanedicarboxylic acid, 4-methyl-1,2-cyclohexanedicarboxylic acid, 3-methyl-4-cyclohexene-1,2-dicarboxylic acid and 4-methyl-4-cyclohexene-1,2-dicarboxylic acid are preferably recommended.

It is recommended that the alicyclic dicarboxylic acid of the formula (2) and its anhydride preferably have a peroxide value of 1.0 meq/kg or less. However, the alicyclic dicarboxylic acids are usually solid at room temperature, and therefore increase in peroxide value thereof is relatively small and would affect the performance of the present ester to a lesser degree, when used as a refrigerator lubricating oil, compared with increase in peroxide value of the alcohol of component b) used in the present invention.

The alicyclic dicarboxylic acids of the formula (2) and anhydrides thereof are known or can be prepared by known processes.

Alicyclic Dicarboxylic Acid Diester Represented by the Formula (3)

In the alicyclic dicarboxylic acid diester of the formula (3), $R^3$ and $R^4$ are the same or different and each is a branched-chain alkyl group having 3 or 4 carbon atoms or a straight-chain alkyl group having 1 to 4 carbon atoms.

Specific examples of the alicyclic dicarboxylic acid diester of the formula (3) are dimethyl 1,2-cyclohexanedicarboxylate, diethyl 1,2-cyclohexanedicarboxylate, di(n-propyl) 1,2-cyclohexanedicarboxylate, di(n-butyl) 1,2-cyclohexanedicarboxylate, diisobutyl 1,2-cyclohexanedicarboxylate, diisopropyl 1,2-cyclohexanedicarboxylate, etc.

The alicyclic dicarboxylic acid diester of the formula (3) can be produced by the process for preparing an alicyclic dicarboxylic acid diester according to the invention. The lower alcohol of 1 to 4 carbon atoms to be used as the raw material is preferably one having a peroxide value of 1.0 meq/kg or less. Furthermore, the alicyclic dicarboxylic acid diesters of the formula (3) preferably have a peroxide value of 1.0 meq/kg or less.

The alicyclic dicarboxylic acid diesters of the formula (3) are known or can be easily prepared by known processes.

Component b) (Aliphatic Monohydric Alcohol)

As the aliphatic monohydric alcohol of 1 to 18 carbon atoms or the alicyclic monohydric alcohol of 3 to 10 carbon atoms to be used as component b) in this esterification, recommended is, more specifically, a monohydric alcohol comprising a branched-chain alkyl group having 3 to 18 carbon atoms, preferably 3 to 11 carbon atoms, a straight-chain alkyl group having 1 to 18 carbon atoms, preferably 3 to 11 carbon atoms, a straight-chain alkenyl group having 2 to 18 carbon atoms or a cycloalkyl group having 3 to 10 carbon atoms, and a hydroxyl group, the alcohol having a peroxide value of 1.0 meq/kg or less, preferably 0.5 meq/kg or less.

It is recommended in the ester interchange reaction to use as component b) an aliphatic monohydric alcohol having 5 to 18 carbon atoms (especially, one made of a branched-chain alkyl group having 5 to 18 carbon atoms or a straight-chain alkyl group having 5 to 18 carbon atoms and a hydroxyl group). More desirably usable is an aliphatic monohydric alcohol having 5 to 11 carbon atoms (especially, one made of a branched-chain alkyl group having 5 to 11 carbon atoms, a straight-chain alkyl group having 5 to 11 carbon atoms and a hydroxyl group).

As the alcohols of component b) used in the esterification reaction and also of component b') used in the ester interchange reaction, recommended are those having a carbonyl value of preferably 15 or less, more preferably 5 or less, and most preferably 1 or less.

When the contemplated ester of the formula (1) is prepared using an alcohol having a peroxide value of 1.0 meq/kg or less and a carbonyl value of 5 or less, the obtained ester shows well balanced properties when used as a refrigerator oil. When the contemplated ester of the formula (1) is prepared using an alcohol having a peroxide value of 1.0 meq/kg or less and a carbonyl value of 1 or less, the obtained ester shows very well balanced properties when used as a refrigerator oil.

The term "peroxide value" used herein is described in 2.5.2-1996 of Standard Methods for the Analysis of Fats, Oil and Related Materials (Japan Oil Chemists' Society), and refers to an amount of iodine released by addition of potassium iodide to a sample and expressed in milliequivalent per kilogram of the sample, according to the method described therein.

The term "carbonyl value" used herein is described in 2.5.4-1996 of Standard Methods for the Analysis of Fats, Oil and Related Materials (Japan Oil Chemists' Society), and refers to a value obtained by causing 2,4-dinitrophenylhydrazine to act on a sample and converting the value of its absorbance at 440 nm to a value per gram of the sample, according to the method described therein.

When an alcohol having a peroxide value of more than 1.0 meq/kg is used, the obtained alicyclic dicarboxylic acid diester is adversely affected in the properties such as hue and peroxide value and involve problems in the properties such as electrical insulating property, heat stability and hydrolysis stability.

An alcohol having a peroxide value of 1.0 meq/kg or less can be prepared by purifying an alcohol having a peroxide value of more than 1.0 meq/kg through distillation or through a treatment with a reducing agent to thereby decrease the peroxide value.

Generally an alcohol immediately after distillation has a peroxide value of 1.0 meq/kg or less. However, such alcohol may show a peroxide value of more than 1.0 meq/kg due to oxidation during a long-term storage (e.g. storage for 6 months or longer) depending on the storage conditions. Therefore, it is necessary to confirm a peroxide value of the alcohol before esterification.

The purification by distillation can be performed, e.g. by distilling an alcohol having a peroxide value exceeding 1.0 meq/kg at 50-300° C. in the presence of an alkali compound under reduced pressure. Useful alkali compounds include, for example, NaOH, KOH, LiOH, etc. It is recommendable to use the alkali compound in an amount of 0.001 to 0.5 wt. % based on the alcohol.

The purification by reduction can be conducted, e.g. by stirring an alcohol having a peroxide value exceeding 1.0 meq/kg at 30-150° C. in the presence of a reducing agent for 30 minutes to 5 hours, preferably 1 to 2 hours. Useful reducing agents include, for example, sodium borohydride, potassium borohydride, lithium borohydride, lithium aluminum hydride, etc. It is recommendable to use the reducing agent in an amount of 30 to 10,000 ppm based on the alcohol.

When an alicyclic dicarboxylic acid diester is prepared using an alcohol having a carbonyl value of 15 or less, preferably 5 or less, more preferably 1 or less, the obtained ester has excellent hue and reduced peroxide value.

In the case of an alcohol having a carbonyl value of more than 15 as well, its carbonyl value can be decreased to 15 or less by purification through distillation or by purification through reduction, which may be carried out following the procedure of the foregoing method for lowering the peroxide value.

Specific examples of the aliphatic monohydric alcohol to be used as component b) in esterification are branched-chain alcohols of 3 to 18 carbon atoms and straight-chain alcohols of 1 to 18 carbon atoms. Examples of the alicyclic monohydric alcohol include cycloalcohol of 3 to 10 carbon atoms.

Especially, 1) when the alicyclic dicarboxylic acid represented by the formula (2) or an anhydride thereof is used as the acid component, it is preferable to use an aliphatic monohydric alcohol having 1 to 18 carbon atoms or an alicyclic monohydric alcohol having 3 to 10 carbon atoms, each having a peroxide value of 1.0 meq/kg or less, and 2) when the alicyclic dicarboxylic acid di($C_1$-$C_4$) lower alkyl diester represented by the formula (3) is used as the acid component, it is preferable to use an aliphatic monohydric alcohol having 5 to 18 carbon atoms or an alicyclic monohydric alcohol having 3 to 10 carbon atoms, each having a peroxide value of 1.0 meq/kg or less.

More specific examples of the aliphatic monohydric branched-chain alcohol are isopropanol, isobutanol, sec-butanol, isopentanol, isohexanol, 2-methylhexanol, 1-methylheptanol, 2-methylheptanol, isoheptanol, 2-ethylhexanol, 2-octanol, isooctanol, isononanol, 3,5,5-trimethylhexanol, 2,6-dimethyl-4-heptanol, isodecanol, isoundecanol, isododecanol, isotridecanol, isotetradecanol, isopentadecanol, isohexadecanol, isoheptadecanol, isooctadecanol, etc.

More specific examples of the aliphatic monohydric straight-chain alcohol are methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, n-pentadecanol, n-hexadecanol, n-heptadecanol, n-octadecanol, 2-hexenol, 5-hexenol, 2-heptenol, 6-heptenol, 2-octenol, 8-nonenol, 2-decenol, 2-undecenol, 10-undecenol, 11-dodecenol, 12-tridecenol, 2-tetradecenol, 2-pentadecenol, 2-hexadecenol, 15-hexadecenol, 2-heptadecenol, 2-octadecenol, 9-octadecenol, etc.

More specific examples of the alicyclic monohydric cycloalcohol include cyclohexanol, methylcyclohexanol, dimethylcyclohexanol, etc.

Among the foregoing alcohols, saturated alcohols of 1 to 18 carbon atoms are preferable to achieve good heat stability. Alcohols of 1 to 11 carbon atoms are desirable to achieve better miscibility with a refrigerant.

The above alcohols can be esterified alone as an alcohol component, or two or more species of alcohol can be used as mixed.

When a mixture of two or more species of the alcohol is used for esterification, the obtained alicyclic dicarboxylic acid diester of the formula (1) is a mixed diester wherein $R^1$ and $R^2$ are different. Such mixed diester is suitably used as well.

In esterification, the alcohol component is used in an amount of about 1 to about 1.5 equivalents, preferably about 1.05 to about 1.2 equivalents, per equivalent of carboxylic acid group of component a), i.e., an alicyclic dicarboxylic acid of the formula (2) or an anhydride thereof or an alicyclic dicarboxylic acid diester of the formula (3).

It is preferred that neither the acid component nor the alcohol component to be used in esterification contain a sulfur element or a phosphorus element as impurities.

Catalyst

In the present invention, the esterification reaction is carried out in the absence of a catalyst or in the presence of a sulfur-free and phosphorus-free catalyst. It is particularly recommended to carry out the esterification in the presence of a sulfur-free and phosphorus-free catalyst.

The sulfur-free and phosphorus-free catalyst for use in the esterification of the invention is a catalyst which does not contain a sulfur element or a phosphorus element in the constituent elements of the catalyst. Specifically, examples of useful catalysts are Lewis acids and alkali metal compounds which contain neither a sulfur element nor a phosphorus element. More specifically, examples of Lewis acids are aluminum derivatives, tin derivatives, titanium derivatives, lead derivatives and zinc derivatives. Examples of alkali metal compounds are sodium alkoxide, potassium alkoxide, sodium hydroxide, potassium hydroxide, etc. These catalysts can be used either alone or in combination. Preferred catalysts are those containing no sulfur element or phosphorus element as impurities.

Of such catalysts, particularly preferred are tetra($C_3$-$C_8$ alkyl) titanate, titanium oxide, titanium hydroxide, sodium alkoxide of 1 to 4 carbon atoms, sodium hydroxide, $C_3$-$C_{12}$ fatty acid tin salt, tin oxide, tin hydroxide, zinc oxide, zinc hydroxide, lead oxide, lead hydroxide, aluminum oxide and aluminum hydroxide. The amount of the catalyst to be used is, for example, about 0.05 to about 1 wt. % based on the total amount of the acid component (component a) above) and the alcohol component (component b) above) used as the raw materials for synthesis of the ester.

Reaction Conditions

The esterification temperature is, for example, in the range of 100 to 230° C. Usually the reaction is completed in 3 to 30 hours.

To accelerate the distillation of water formed by the reaction, a water-entraining agent such as benzene, toluene, xylene, cyclohexane or the like may be used in the esterification.

The esterification reaction may be carried out under atmospheric pressure or under reduced pressure (e.g., 133 to 66500 Pa). However, from a viewpoint of accelerating the esterification reaction, it is preferable to combine esterification reaction under atmospheric pressure and esterification reaction under reduced pressure. Particularly, it is recommended to carry out the esterification reaction under reduced pressure in a later stage of the reaction (such as the stage in which the total acid number of the reaction mixture becomes about 10 mgKOH/g or less) when the esterification reaction velocity becomes low.

When oxides, peroxides, carbonyl compounds and like oxygen-containing organic compound are produced in esterification reaction due to oxidative deterioration of the raw material, the obtained ester and the organic solvent (water-entraining agent), the hygroscopicity, hydrolysis stability and electrical insulating property would be adversely affected. Consequently, the esterification reaction is preferably carried out in an atmosphere or stream of inert gas such as nitrogen gas.

In the process of the invention for preparing an alicyclic dicarboxylic acid diester for use as a lubricating oil for refrigerators, a preferable combinations of properties of the aliphatic monohydric alcohol of 1 to 18 carbon atoms or alicyclic monohydric alcohol of 3 to 10 carbon atoms constituting the ester are, for example, as follows:

1) an aliphatic monohydric alcohol having a peroxide value of 1.0 meq/kg or less,
2) an aliphatic monohydric alcohol having a peroxide value of 1.0 meq/kg or less and a carbonyl value of 15 or less,
3) an aliphatic monohydric alcohol having a peroxide value of 1.0 meq/kg or less and a carbonyl value of 5 or less,
4) an aliphatic monohydric alcohol having a peroxide value of 0.5 meq/kg or less and a carbonyl value of 5 or less, and
5) an aliphatic monohydric alcohol having a peroxide value of 0.5 meq/kg or less and a carbonyl value of 1 or less.

Esters of Embodiment II and Process for Preparation Thereof

Alicyclic or Aromatic Adjacent Dicarboxylic Acid Mixed Diester Useful for a Refrigerator Oil According to the present invention, by carrying out two-step esterification comprising the steps of (a) reacting an alicyclic or aromatic adjacent dicarboxylic anhydride represented by the formula (5s)

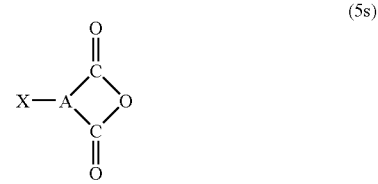

wherein A and X are as defined above, with "alcohol component 1" to be described later to produce an alicyclic or aromatic adjacent dicarboxylic acid monoester represented by the formula (5)

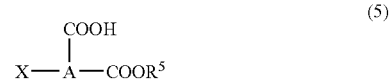

wherein A represents a cyclohexane ring, a cyclohexene ring or a benzene ring, X is a hydrogen atom or methyl group, and $R^5$ is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms and the groups —COOR$^5$ and —COOH are attached to two adjacent carbon atoms of the cyclohexane, cyclohexene or benzene ring represented by A ("step (a)" or first stage), and (b) esterifying the alicyclic or aromatic adjacent dicarboxylic acid monoester of the formula (5) with "alcohol component 2" ("step (b)" or second stage), the foregoing alicyclic or aromatic adjacent dicarboxylic acid mixed diester represented by the formula (4)

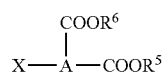
(4)

wherein A and X are as defined above, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, and the groups —COOR$^5$ and —COOR$^6$ are attached to two adjacent carbon atoms of the cyclohexane, cyclohexene or benzene ring represented by A is obtained, and this mixed diester is used as a refrigerator oil, wherein said "alcohol component 1" comprises a monohydric alcohol of 1 to 5 carbon atoms (P) and optionally a monohydric alcohol of 6 to 18 carbon atoms (Q) (wherein (P):(Q)=0.1:99.9 to 100:0 (molar ratio)), and said "alcohol component 2" comprises a monohydric alcohol of 6 to 18 carbon atoms (T) and optionally a monohydric alcohol of 1 to 5 carbon atoms (S) (wherein (S):(T)=0:100 to 99.9:0.1 (molar ratio)).

The monohydric alcohol of 1 to 5 carbon atoms (P) constituting said "alcohol component 1" is, more specifically, an alcohol composed of a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and a hydroxyl group. The monohydric alcohol of 6 to 18 carbon atoms (Q) is an alcohol composed of a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and a hydroxyl group.

Preferably, said alcohol component 1 is an alcohol selected from monohydric alcohols (P) of 1 to 5 carbon atoms.

The monohydric alcohol of 1 to 5 carbon atoms (S) constituting said "alcohol component 2" is, more specifically, an alcohol composed of a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and a hydroxyl group. The monohydric alcohol of 6 to 18 carbon atoms (T) is an alcohol composed of a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and a hydroxyl group.

Preferably the alcohol component 2 is an alcohol selected from the monohydric alcohols (T) of 6 to 18 carbon atoms.

In the alicyclic or aromatic adjacent dicarboxylic acid mixed diester of the invention represented by the formula (4), $R^5$ and $R^6$ are different from each other.

When, for example, an alcohol ($R^5$OH) selected from the monohydric alcohols of 1 to 5 carbon atoms (P) is used as alcohol component 1, and an alcohol ($R^6$OH) selected from the monohydric alcohols (T) of 6 to 18 carbon atoms is used as alcohol component 2, in the resulting alicyclic or aromatic adjacent dicarboxylic acid mixed diester of the invention represented by the formula (4), $R^5$ is a group resulting from elimination of the hydroxyl group from said monohydric alcohol of 1 to 5 carbon atoms (S), i.e. a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and $R^6$ is a group resulting from elimination of the hydroxyl group from the monohydric alcohols of 6 to 18 carbon atoms (T), i.e. a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms.

In the present invention, A represents a cyclohexane ring, a cyclohexene ring or a benzene ring, X is a hydrogen atom or methyl, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 0.18 carbon atoms or a cycloalkyl group having 3 to 10 carbon atoms.

The group —COOR$^5$ is present in a position adjacent to the substitution position of the group —COOR$^6$ on the cyclohexane ring, cyclohexene ring or benzene ring represented by A.

Further, in the cyclohexane ring or in the cyclohexene ring, when the group —COOR$^5$ is present in the 1-position, the group —COOR$^6$ is present in the 2-position, and when the group —COOR$^5$ is present in the 2-position, the group —COOR$^6$ is present in the 1-position.

Specific examples of the alicyclic dicarboxylic acid mixed diester represented by the formula (4) are (methyl)(cyclohexyl) 1,2-cyclohexanedicarboxylate, (methyl) (n-heptyl) 1,2-cyclohexanedicarboxylate, (methyl)(isoheptyl) 1,2-cyclohexanedicarboxylate, (methyl)(n-octyl) 1,2-cyclohexanedicarboxylate, (methyl)(2-ethylhexyl) 1,2-cyclohexanedicarboxylate, (methyl) (isooctyl) 1,2-cyclohexanedicarboxylate, (methyl)(2-octyl) 1,2-cyclohexanedicarboxylate, (methyl)(n-nonyl) 1,2-cyclohexanedicarboxylate, (methyl)(isononyl) 1,2-cyclohexanedicarboxylate, (methyl) (3,5,5-trimethylhexyl) 1,2-cyclohexanedicarboxylate, (methyl)(n-decyl) 1,2-cyclohexanedicarboxylate, (methyl)(isodecyl) 1,2-cyclohexanedicarboxylate, (methyl)(n-undecyl) 1,2-cyclohexanedicarboxylate, (methyl)(isoundecyl) 1,2-cyclohexanedicarboxylate, (methyl)(n-dodecyl) 1,2-cyclohexanedicarboxylate, (methyl)(isododecyl) 1,2-cyclohexanedicarboxylate, (methyl)(n-tridecyl) 1,2-cyclohexanedicarboxylate, (methyl)(isotridecyl) 1,2-cyclohexanedicarboxylate, (methyl)(n-tetradecyl) 1,2-cyclohexanedicarboxylate, (methyl)(isotetradecyl) 1,2-cyclohexanedicarboxylate, (methyl)(n-pentadecyl) 1,2-cyclohexanedicarboxylate, (methyl)(isopentadecyl) 1,2-cyclohexanedicarboxylate, (methyl)(n-hexadecyl) 1,2-cyclohexanedicarboxylate, (methyl)(isohexadecyl) 1,2-cyclohexanedicarboxylate, (methyl)(n-heptadecyl) 1,2-cyclohexanedicarboxylate, (methyl)(isoheptadecyl) 1,2- cyclohexanedicarboxylate, (methyl)(n-octadecyl) 1,2-cyclohexanedicarboxylate, (methyl)(isooctadecyl) 1,2-cyclohexanedicarboxylate, (ethyl)(cyclohexyl) 1,2-cyclohexanedicarboxylate, (ethyl)(n-heptyl) 1,2-cyclohexanedicarboxylate, (ethyl)(isoheptyl) 1,2-cyclohexanedicarboxylate, (ethyl)(n-octyl) 1,2-cyclohexanedicarboxylate, (ethyl)(2-ethylhexyl) 1,2-cyclohexanedicarboxylate, (ethyl)(isooctyl) 1,2-cyclohexanedicarboxylate, (ethyl)(2-octyl) 1,2-cyclohexanedicarboxylate, (ethyl)(n-nonyl) 1,2-cyclohexanedicarboxylate, (ethyl)(isononyl) 1,2-cyclohexanedicarboxylate, (ethyl)(3,5,5-trimethylhexyl) 1,2-cyclohexanedicarboxylate, (ethyl)(n-decyl) 1,2-cyclohexanedicarboxylate, (ethyl)(isodecyl) 1,2-cyclohexanedicarboxylate, (ethyl)(n-undecyl) 1,2-cyclohexanedicarboxylate, (ethyl)(isoundecyl) 1,2-cyclohexanedicarboxylate, (ethyl)(n-dodecyl) 1,2-cyclohexanedicarboxylate, (ethyl)(isododecyl) 1,2-cyclohexanedicarboxylate, (ethyl)(n-tridecyl) 1,2-cyclohexanedicarboxylate, (ethyl)(isotridecyl) 1,2-cyclohexanedicarboxylate, (ethyl)(n-tetradecyl) 1,2-cyclohexanedicarboxylate, (ethyl)(isotetradecyl) 1,2-cyclohexanedicarboxylate, (ethyl)(n-pentadecyl) 1,2-cyclohexanedicarboxylate, (ethyl)(isopentadecyl) 1,2-cyclohexanedicarboxylate, (ethyl)(n-hexadecyl) 1,2-cyclohexanedicarboxylate, (ethyl)(isohexadecyl) 1,2-cyclohexanedicarboxylate, (ethyl)(n-heptadecyl) 1,2-cyclohexanedicarboxylate, (ethyl)(isoheptadecyl) 1,2-cyclohexanedicarboxylate, (ethyl)(n-octadecyl) 1,2-cyclohexanedicarboxylate, (ethyl)(isooctadecyl) 1,2-cyclohexanedicarboxylate, (n-propyl)(cyclohexyl) 1,2-cyclohexanedicarboxylate, (n-propyl)(n-heptyl) 1,2-cyclohexanedicarboxylate, (n-propyl)(isoheptyl) 1,2-cyclohexanedicarboxylate, (n-propyl)(n-octyl) 1,2-cyclohexanedicarboxylate, (n-propyl)(2-ethylhexyl) 1,2-cyclohexanedicarboxylate, (n-propyl)(isooctyl) 1,2-cyclohexanedicarboxylate, (n-propyl)(2-octyl) 1,2-cyclohexanedicarboxylate, (n-propyl)(n-nonyl) 1,2-cyclohexanedicarboxylate, (n-propyl)(isononyl) 1,2-cyclohexanedicarboxylate, (n-propyl)(3,5,5-trimethylhexyl) 1,2-cyclohexanedicarboxylate, (n-propyl)(n-decyl) 1,2-cyclohexanedicarboxylate, (n-propyl)(isodecyl) 1,2-cyclohexanedicarboxylate, (n-propyl)(n-undecyl) 1,2-cyclohexanedicarboxylate, (n-propyl)(isoundecyl) 1,2-cyclohexanedicarboxylate, (n-propyl)(n-dodecyl) 1,2-cyclohexanedicarboxylate, (n-propyl)(isododecyl) 1,2-cyclohexanedicarboxylate, (n-propyl)(n-tridecyl) 1,2-cyclohexanedicarboxylate, (n-propyl)(isotridecyl) 1,2-cyclohexanedicarboxylate, (n-propyl)(n-tetradecyl) 1,2-cyclohexanedicarboxylate, (n-propyl)(isotetradecyl) 1,2-cyclohexanedicarboxylate, (n-propyl)(n-pentadecyl) 1,2-cyclohexanedicarboxylate, (n-propyl) (isopentadecyl) 1,2-cyclohexanedicarboxylate, (n-propyl) (n-hexadecyl) 1,2-cyclohexanedicarboxylate, (n-propyl)(isohexadecyl) 1,2-cyclohexanedicarboxylate, (n-propyl)(n-heptadecyl) 1,2-cyclohexanedicarboxylate, (n-propyl)(isoheptadecyl) 1,2-cyclohexanedicarboxylate, (n-propyl)(n-octadecyl) 1,2-cyclohexanedicarboxylate, (n-propyl)(isooctadecyl) 1,2-cyclohexanedicarboxylate, (isopropyl) (cyclohexyl) 1,2-cyclohexanedicarboxylate, (isopropyl)(n-heptyl) 1,2-cyclohexanedicarboxylate, (isopropyl)(isoheptyl) 1,2-cyclohexanedicarboxylate, (isopropyl)(n-octyl) 1,2-cyclohexanedicarboxylate, (isopropyl)(2-ethylhexyl) 1,2-cyclohexanedicarboxylate, (isopropyl)(isooctyl) 1,2-cyclohexanedicarboxylate, (isopropyl)(2-octyl) 1,2-cyclohexanedicarboxylate, (isopropyl)(n-nonyl) 1,2-cyclohexanedicarboxylate, (isopropyl)(isononyl) 1,2-cyclohexanedicarboxylate, (isopropyl)(3,5,5-trimethylhexyl) 1,2-cyclohexanedicarboxylate, (isopropyl)(n-decyl) 1,2-cyclohexanedicarboxylate, (isopropyl)(isodecyl) 1,2-cyclohexanedicarboxylate, (isopropyl)(n-undecyl) 1,2-cyclohexanedicarboxylate, (isopropyl)(isoundecyl) 1,2-cyclohexanedicarboxylate, (isopropyl)(n-dodecyl) 1,2-cyclohexanedicarboxylate, (isopropyl)(isododecyl) 1,2-cyclohexanedicarboxylate, (isopropyl)(n-tridecyl) 1,2-cyclohexanedicarboxylate, (isopropyl)(isotridecyl) 1,2-cyclohexanedicarboxylate, (isopropyl)(n-tetradecyl) 1,2-cyclohexanedicarboxylate, (isopropyl)(isotetradecyl) 1,2-cyclohexanedicarboxylate, (isopropyl)(n-pentadecyl) 1,2-cyclohexanedicarboxylate, (isopropyl)(isopentadecyl) 1,2-cyclohexanedicarboxylate, (isopropyl)(n-hexadecyl) 1,2-cyclohexanedicarboxylate, (isopropyl)(isohexadecyl) 1,2-cyclohexanedicarboxylate, (isopropyl)(n-heptadecyl) 1,2-cyclohexanedicarboxylate, (isopropyl)(isoheptadecyl) 1,2-cyclohexanedicarboxylate, (isopropyl)(n-octadecyl) 1,2-cyclohexanedicarboxylate, (isopropyl)(isooctadecyl) 1,2-cyclohexanedicarboxylate, (n-butyl)(cyclohexyl) 1,2-cyclohexanedicarboxylate, (n-butyl)(n-heptyl) 1,2-cyclohexanedicarboxylate, (n-butyl)(isoheptyl) 1,2-cyclohexanedicarboxylate, (n-butyl)(n-octyl) 1,2-cyclohexanedicarboxylate, (n-butyl)(2-ethylhexyl) 1,2-cyclohexanedicarboxylate, (n-butyl)(isooctyl) 1,2-cyclohexanedicarboxylate, (n-butyl)(2-octyl) 1,2-cyclohexanedicarboxylate, (n-butyl)(n-nonyl) 1,2-cyclohexanedicarboxylate, (n-butyl)(isononyl) 1,2-cyclohexanedicarboxylate, (n-butyl)(3,5,5-trimethylhexyl) 1,2-cyclohexanedicarboxylate, (n-butyl)(n-decyl) 1,2-cyclohexanedicarboxylate, (n-butyl)(isodecyl) 1,2-cyclohexanedicarboxylate, (n-butyl)(n-undecyl) 1,2-cyclohexanedicarboxylate, (n-butyl)(isoundecyl) 1,2-cyclohexanedicarboxylate, (n-butyl)(n-dodecyl) 1,2-cyclohexanedicarboxylate, (n-butyl)(isododecyl) 1,2-cyclohexanedicarboxylate, (n-butyl)(n-tridecyl) 1,2-cyclohexanedicarboxylate, (n-butyl)(isotridecyl) 1,2-cyclohexanedicarboxylate, (n-butyl)(n-tetradecyl) 1,2-cyclohexanedicarboxylate, (n-butyl)(isotetradecyl) 1,2-cyclohexanedicarboxylate, (n-butyl)(n-pentadecyl) 1,2-cyclohexanedicarboxylate, (n-butyl)(isopentadecyl) 1,2-cyclohexanedicarboxylate, (n-butyl)(n-hexadecyl) 1,2-cyclohexanedicarboxylate, (n-butyl)(isohexadecyl) 1,2-cyclohexanedicarboxylate, (n-butyl)(n-heptadecyl) 1,2-cyclohexanedicarboxylate, (n-butyl)(isoheptadecyl) 1,2-cyclohexanedicarboxylate, (n-butyl)(n-octadecyl) 1,2-cyclohexanedicarboxylate, (n-butyl)(isooctadecyl) 1,2-cyclohexanedicarboxylate, (isobutyl)(cyclohexyl) 1,2-cyclohexanedicarboxylate, (isobutyl)(n-heptyl) 1,2-cyclohexanedicarboxylate, (isobutyl)(isoheptyl) 1,2-cyclohexanedicarboxylate, (isobutyl) (n-octyl) 1,2-cyclohexanedicarboxylate, (isobutyl)(2-ethylhexyl) 1,2-cyclohexanedicarboxylate, (isobutyl)(isooctyl) 1,2-cyclohexanedicarboxylate, (isobutyl)(2-octyl) 1,2-cyclohexanedicarboxylate, (isobutyl)(n-nonyl) 1,2-cyclohexanedicarboxylate, (isobutyl)(isononyl) 1,2-cyclohexanedicarboxylate, (isobutyl)(3,5,5-trimethylhexyl) 1,2-cyclohexanedicarboxylate, (isobutyl)(n-decyl) 1,2-cyclohexanedicarboxylate, (isobutyl)(isodecyl) 1,2-cyclohexanedicarboxylate, (isobutyl)(n-undecyl) 1,2-cyclohexanedicarboxylate, (isobutyl)(isoundecyl) 1,2-cyclohexanedicarboxylate, (isobutyl)(n-dodecyl) 1,2-cyclohexanedicarboxylate, (isobutyl)(isododecyl) 1,2-cyclohexanedicarboxylate, (isobutyl)(n-tridecyl) 1,2-cyclohexanedicarboxylate, (isobutyl)(isotridecyl) 1,2-cyclohexanedicarboxylate, (isobutyl)(n-tetradecyl) 1,2-cyclohexanedicarboxylate, (isobutyl)(isotetradecyl) 1,2-cyclohexanedicarboxylate, (isobutyl)(n-pentadecyl) 1,2-cyclohexanedicarboxylate, (isobutyl)(isopentadecyl) 1,2- cyclohexanedicarboxylate, (isobutyl)(n-hexadecyl) 1,2-cyclohexanedicarboxylate, (isobutyl)(isohexadecyl) 1,2-cyclohexanedicarboxylate, (isobutyl)(n-heptadecyl) 1,2-cyclohexanedicarboxylate, (isobutyl)(isoheptadecyl) 1,2-cyclohexanedicarboxylate, (isobutyl)(n-octadecyl) 1,2-cyclohexanedicarboxylate, (isobutyl)(isooctadecyl) 1,2-cyclohexanedicarboxylate, (sec-butyl)(cyclohexyl) 1,2-cyclohexanedicarboxylate, (sec-butyl)(n-heptyl) 1,2-cyclohexanedicarboxylate, (sec-butyl)(isoheptyl) 1,2-cyclohexanedicarboxylate, (sec-butyl)(n-octyl) 1,2-cyclohexanedicarboxylate, (sec-butyl)(2-ethylhexyl) 1,2-cyclohexanedicarboxylate, (sec-butyl)(isooctyl) 1,2-cyclohexanedicarboxylate, (sec-butyl)(2-octyl) 1,2-cyclohexanedicarboxylate, (sec-butyl)(n-nonyl) 1,2-cyclohexanedicarboxylate, (sec-butyl)(isononyl) 1,2-cyclohexanedicarboxylate, (sec-butyl)(3,5,5-trimethylhexyl) 1,2-cyclohexanedicarboxylate, (sec-butyl) (n-decyl) 1,2-cyclohexanedicarboxylate, (sec-butyl) (isodecyl) 1,2-cyclohexanedicarboxylate, (sec-butyl)(n-undecyl) 1,2-cyclohexanedicarboxylate, (sec-butyl) (isoundecyl) 1,2-cyclohexanedicarboxylate, (sec-butyl)(n-dodecyl) 1,2-cyclohexanedicarboxylate, (sec-butyl) (isododecyl) 1,2-cyclohexanedicarboxylate, (sec-butyl)(n-tridecyl) 1,2-cyclohexanedicarboxylate, (sec-butyl) (isotridecyl) 1,2-cyclohexanedicarboxylate, (sec-butyl)(n-tetradecyl) 1,2-cyclohexanedicarboxylate, (sec-butyl) (isotetradecyl) 1,2-cyclohexanedicarboxylate, (sec-butyl)(n-pentadecyl) 1,2-cyclohexanedicarboxylate, (sec-butyl) (isopentadecyl) 1,2-cyclohexanedicarboxylate, (sec-butyl) (n-hexadecyl) 1,2-cyclohexanedicarboxylate, (sec-butyl) (isohexadecyl) 1,2-cyclohexanedicarboxylate, (sec-butyl) (n-heptadecyl) 1,2-cyclohexanedicarboxylate, (sec-butyl) (isoheptadecyl) 1,2-cyclohexanedicarboxylate, (sec-butyl) (n-octadecyl) 1,2-cyclohexanedicarboxylate, (sec-butyl) (isooctadecyl) 1,2-cyclohexanedicarboxylate, (methyl) (cyclohexyl) 4-cyclohexene-1,2-dicarboxylate, (methyl)(n-heptyl) 4-cyclohexene-1,2-dicarboxylate, (methyl) (isoheptyl) 4-cyclohexene-1,2-dicarboxylate, (methyl)(n-octyl) 4-cyclohexene-1,2-dicarboxylate, (methyl)(2-ethylhexyl) 4-cyclohexene-1,2-dicarboxylate, (methyl) (isooctyl) 4-cyclohexene-1,2-dicarboxylate, (methyl)(2-octyl) 4-cyclohexene-1,2-dicarboxylate, (methyl)(n-nonyl) 4-cyclohexene-1,2-dicarboxylate, (methyl)(isononyl) 4-cyclohexene-1,2-dicarboxylate, (methyl) (3,5,5-trimethylhexyl) 4-cyclohexene-1,2-dicarboxylate, (methyl)(n-decyl) 4-cyclohexene-1,2-dicarboxylate, (methyl)(isodecyl) 4-cyclohexene-1,2-dicarboxylate, (methyl)(n-undecyl) 4-cyclohexene-1,2-dicarboxylate, (methyl)(isoundecyl) 4-cyclohexene-1,2-dicarboxylate, (methyl)(n-dodecyl) 4-cyclohexene-1,2-dicarboxylate, (methyl)(isododecyl) 4-cyclohexene-1,2-dicarboxylate, (methyl)(n-tridecyl) 4-cyclohexene-1,2-dicarboxylate, (methyl)(isotridecyl) 4-cyclohexene-1,2-dicarboxylate, (methyl)(n-tetradecyl) 4-cyclohexene-1,2-dicarboxylate, (methyl)(isotetradecyl) 4-cyclohexene-1,2-dicarboxylate, (methyl)(n-pentadecyl) 4-cyclohexene-1,2-dicarboxylate, (methyl)(isopentadecyl) 4-cyclohexene-1,2-dicarboxylate, (methyl)(n-hexadecyl) 4-cyclohexene-1,2-dicarboxylate, (methyl)(isohexadecyl) 4-cyclohexene-1,2-dicarboxylate, (methyl)(n-heptadecyl) 4-cyclohexene-1,2-dicarboxylate, (methyl)(isoheptadecyl) 4-cyclohexene-1,2-dicarboxylate, (methyl)(n-octadecyl) 4-cyclohexene-1,2-dicarboxylate, (methyl)(isooctadecyl) 4-cyclohexene-1,2-dicarboxylate, (ethyl)(cyclohexyl) 4-cyclohexene-1,2-dicarboxylate, (ethyl)(n-heptyl) 4-cyclohexene-1,2-dicarboxylate, (ethyl)(isoheptyl) 4-cyclohexene-1,2-dicarboxylate, (ethyl)(n-octyl) 4-cyclohexene-1,2-dicarboxylate, (ethyl)(2-ethylhexyl) 4-cyclohexene-1,2-dicarboxylate, (ethyl)(isooctyl) 4-cyclohexene-1,2-dicarboxylate, (ethyl)(2-octyl) 4-cyclohexene-1,2-dicarboxylate, (ethyl)(n-nonyl) 4-cyclohexene-1,2-dicarboxylate, (ethyl)(isononyl) 4-cyclohexene-1,2-dicarboxylate, (ethyl)(3,5,5-trimethylhexyl) 4-cyclohexene-1,2-dicarboxylate, (ethyl)(n-decyl) 4-cyclohexene-1,2-dicarboxylate, (ethyl)(isodecyl) 4-cyclohexene-1,2-dicarboxylate, (ethyl)(n-undecyl) 4-cyclohexene-1,2-dicarboxylate, (ethyl)(isoundecyl) 4-cyclohexene-1,2-dicarboxylate, (ethyl)(n-dodecyl) 4-cyclohexene-1,2-dicarboxylate, (ethyl)(isododecyl) 4-cyclohexene-1,2-dicarboxylate, (ethyl)(n-tridecyl) 4-cyclohexene-1,2-dicarboxylate, (ethyl)(isotridecyl) 4-cyclohexene-1,2-dicarboxylate, (ethyl)(n-tetradecyl) 4-cyclohexene-1,2-dicarboxylate, (ethyl)(isotetradecyl) 4-cyclohexene-1,2-dicarboxylate, (ethyl)(n-pentadecyl) 4-cyclohexene-1,2-dicarboxylate, (ethyl)(isopentadecyl) 4-cyclohexene-1,2-dicarboxylate, (ethyl)(n-hexadecyl) 4-cyclohexene-1,2-dicarboxylate, (ethyl)(isohexadecyl) 4-cyclohexene-1,2-dicarboxylate, (ethyl)(n-heptadecyl) 4-cyclohexene-1,2-dicarboxylate, (ethyl)(isoheptadecyl) 4-cyclohexene-1,2-dicarboxylate, (ethyl)(n-octadecyl) 4-cyclohexene-1,2-dicarboxylate, (ethyl)(isooctadecyl) 4-cyclohexene-1,2-dicarboxylate, (n-propyl)(cyclohexyl) 4-cyclohexene-1,2-dicarboxylate, (n-propyl)(n-heptyl) 4-cyclohexene-1,2-dicarboxylate, (n-propyl)(isoheptyl) 4-cyclohexene-1,2-dicarboxylate, (n-propyl)(n-octyl) 4-cyclohexene-1,2-dicarboxylate, (n-propyl)(2-ethylhexyl) 4-cyclohexene-1,2-dicarboxylate, (n-propyl)(isooctyl) 4-cyclohexene-1,2-dicarboxylate, (n-propyl)(2-octyl) 4-cyclohexene-1,2-dicarboxylate, (n-propyl)(n-nonyl) 4-cyclohexene-1,2-dicarboxylate, (n-propyl)(isononyl) 4-cyclohexene-1,2-dicarboxylate, (n-propyl)(3,5,5-trimethylhexyl) 4-cyclohexene-1,2-dicarboxylate, (n-propyl)(n-decyl) 4-cyclohexene-1,2-dicarboxylate, (n-propyl)(isodecyl) 4-cyclohexene-1,2-dicarboxylate, (n-propyl)(n-undecyl) 4-cyclohexene-1,2-dicarboxylate, (n-propyl)(isoundecyl) 4-cyclohexene-1,2-dicarboxylate, (n-propyl)(n-dodecyl) 4-cyclohexene-1,2-dicarboxylate, (n-propyl)(isododecyl) 4-cyclohexene-1,2-dicarboxylate, (n-propyl)(n-tridecyl) 4-cyclohexene-1,2-dicarboxylate, (n-propyl)(isotridecyl) 4-cyclohexene-1,2-dicarboxylate, (n-propyl)(n-tetradecyl) 4-cyclohexene-1,2-dicarboxylate, (n-propyl)(isotetradecyl) 4-cyclohexene-1,2-dicarboxylate, (n-propyl)(n-pentadecyl) 4-cyclohexene-1,2-dicarboxylate, (n-propyl)(isopentadecyl) 4-cyclohexene-1,2-dicarboxylate, (n-propyl)(n-hexadecyl) 4-cyclohexene-1,2-dicarboxylate, (n-propyl)(isohexadecyl) 4-cyclohexene-1,2-dicarboxylate, (n-propyl)(n-heptadecyl) 4-cyclohexene-1,2-dicarboxylate, (n-propyl)(isoheptadecyl) 4-cyclohexene-1,2-dicarboxylate, (n-propyl)(n-octadecyl) 4-cyclohexene-1,2-dicarboxylate, (n-propyl)(isooctadecyl) 4-cyclohexene-1,2-dicarboxylate, (isopropyl)(cyclohexyl) 4-cyclohexene-1,2-dicarboxylate, (isopropyl)(n-heptyl) 4-cyclohexene-1,2-dicarboxylate, (isopropyl)(isoheptyl) 4-cyclohexene-1,2-dicarboxylate, (isopropyl)(n-octyl) 4-cyclohexene-1,2-dicarboxylate, (isopropyl)(2-ethylhexyl) 4-cyclohexene-1,2-dicarboxylate, (isopropyl)(isooctyl) 4-cyclohexene-1,2-dicarboxylate, (isopropyl)(2-octyl) 4-cyclohexene-1,2-dicarboxylate, (isopropyl)(n-nonyl) 4-cyclohexene-1,2-dicarboxylate, (isopropyl)(isononyl) 4-cyclohexene-1,2-dicarboxylate, (isopropyl)(3,5,5-trimethylhexyl) 4-cyclohexene-1,2-dicarboxylate, (isopropyl)(n-decyl) 4-cyclohexene-1,2-dicarboxylate, (isopropyl)(isodecyl) 4-cyclohexene-1,2-dicarboxylate, (isopropyl)(n-undecyl) 4-cyclohexene-1,2-dicarboxylate, (isopropyl)(isoundecyl) 4-cyclohexene-1,2-dicarboxylate, (isopropyl)(n-dodecyl) 4-cyclohexene-1,2-dicarboxylate, (isopropyl)(isododecyl)

4-cyclohexene-1,2-dicarboxylate, (isopropyl)(n-tridecyl) 4-cyclohexene-1,2-dicarboxylate, (isopropyl)(isotridecyl) 4-cyclohexene-1,2-dicarboxylate, (isopropyl)(n-tetradecyl) 4-cyclohexene-1,2-dicarboxylate, (isopropyl)(isotetradecyl) 4-cyclohexene-1,2-dicarboxylate, (isopropyl)(n-pentadecyl) 4-cyclohexene-1,2-dicarboxylate, (isopropyl)(isopentadecyl) 4-cyclohexene-1,2-dicarboxylate, (isopropyl)(n-hexadecyl) 4-cyclohexene-1,2-dicarboxylate, (isopropyl)(isohexadecyl) 4-cyclohexene-1,2-dicarboxylate, (isopropyl)(n-heptadecyl) 4-cyclohexene-1,2-dicarboxylate, (isopropyl)(isoheptadecyl) 4-cyclohexene-1,2-dicarboxylate, (isopropyl)(n-octadecyl) 4-cyclohexene-1,2-dicarboxylate, (isopropyl)(isooctadecyl) 4-cyclohexene-1,2-dicarboxylate, (n-butyl)(cyclohexyl) 4-cyclohexene-1,2-dicarboxylate, (n-butyl)(n-heptyl) 4-cyclohexene-1,2-dicarboxylate, (n-butyl)(isoheptyl) 4-cyclohexene-1,2-dicarboxylate, (n-butyl)(n-octyl) 4-cyclohexene-1,2-dicarboxylate, (n-butyl)(2-ethylhexyl) 4-cyclohexene-1,2-dicarboxylate, (n-butyl)(isooctyl) 4-cyclohexene-1,2-dicarboxylate, (n-butyl)(2-octyl) 4-cyclohexene-1,2-dicarboxylate, (n-butyl)(n-nonyl) 4-cyclohexene-1,2-dicarboxylate, (n-butyl)(isononyl) 4-cyclohexene-1,2-dicarboxylate, (n-butyl) (3,5,5-trimethylhexyl) 4-cyclohexene-1,2-dicarboxylate, (n-butyl)(n-decyl) 4-cyclohexene-1,2-dicarboxylate, (n-butyl)(isodecyl) 4-cyclohexene-1,2-dicarboxylate, (n-butyl)(n-undecyl) 4-cyclohexene-1,2-dicarboxylate, (n-butyl)(isoundecyl) 4-cyclohexene-1,2-dicarboxylate, (n-butyl)(n-dodecyl) 4-cyclohexene-1,2-dicarboxylate, (n-butyl)(isododecyl) 4-cyclohexene-1,2-dicarboxylate, (n-butyl)(n-tridecyl) 4-cyclohexene-1,2-dicarboxylate, (n-butyl)(isotridecyl) 4-cyclohexene-1,2-dicarboxylate, (n-butyl)(n-tetradecyl) 4-cyclohexene-1,2-dicarboxylate, (n-butyl)(isotetradecyl) 4-cyclohexene-1,2-dicarboxylate, (n-butyl)(n-pentadecyl) 4-cyclohexene-1,2-dicarboxylate, (n-butyl)(isopentadecyl) 4-cyclohexene-1,2-dicarboxylate, (n-butyl)(n-hexadecyl) 4-cyclohexene-1,2-dicarboxylate, (n-butyl)(isohexadecyl) 4-cyclohexene-1,2-dicarboxylate, (n-butyl)(n-heptadecyl) 4-cyclohexene-1,2-dicarboxylate, (n-butyl)(isoheptadecyl) 4-cyclohexene-1,2-dicarboxylate, (n-butyl)(n-octadecyl) 4-cyclohexene-1,2-dicarboxylate, (n-butyl)(isooctadecyl) 4-cyclohexene-1,2-dicarboxylate, (isobutyl)(cyclohexyl) 4-cyclohexene-1,2-dicarboxylate, (isobutyl)(n-heptyl) 4-cyclohexene-1,2-dicarboxylate, (isobutyl)(isoheptyl) 4-cyclohexene-1,2-dicarboxylate, (isobutyl)(n-octyl) 4-cyclohexene-1,2-dicarboxylate, (isobutyl)(2-ethylhexyl) 4-cyclohexene-1,2-dicarboxylate, (isobutyl)(isooctyl) 4-cyclohexene-1,2-dicarboxylate, (isobutyl)(2-octyl) 4-cyclohexene-1,2-dicarboxylate, (isobutyl)(n-nonyl) 4-cyclohexene-1,2-dicarboxylate, (isobutyl)(isononyl) 4-cyclohexene-1,2-dicarboxylate, (isobutyl)(3,5,5-trimethylhexyl) 4-cyclohexene-1,2-dicarboxylate, (isobutyl)(n-decyl) 4-cyclohexene-1,2-dicarboxylate, (isobutyl)(isodecyl) 4-cyclohexene-1,2-dicarboxylate, (isobutyl)(n-undecyl) 4-cyclohexene-1,2-dicarboxylate, (isobutyl)(isoundecyl) 4-cyclohexene-1,2-dicarboxylate, (isobutyl)(n-dodecyl) 4-cyclohexene-1,2-dicarboxylate, (isobutyl)(isododecyl) 4-cyclohexene-1,2-dicarboxylate, (isobutyl)(n-tridecyl) 4-cyclohexene-1,2-dicarboxylate, (isobutyl)(isotridecyl) 4-cyclohexene-1,2-dicarboxylate, (isobutyl)(n-tetradecyl) 4-cyclohexene-1,2-dicarboxylate, (isobutyl)(isotetradecyl) 4-cyclohexene-1,2-dicarboxylate, (isobutyl)(n-pentadecyl) 4-cyclohexene-1,2-dicarboxylate, (isobutyl)(isopentadecyl) 4-cyclohexene-1,2-dicarboxylate, (isobutyl)(n-hexadecyl) 4-cyclohexene-1,2-dicarboxylate, (isobutyl)(isohexadecyl) 4-cyclohexene-1,2-dicarboxylate, (isobutyl)(n-heptadecyl) 4-cyclohexene-1,2-dicarboxylate, (isobutyl)(isoheptadecyl) 4-cyclohexene-1,2-dicarboxylate, (isobutyl)(n-octadecyl) 4-cyclohexene-1,2-dicarboxylate, (isobutyl)(isooctadecyl) 4-cyclohexene-1,2-dicarboxylate, (sec-butyl)(cyclohexyl) 4-cyclohexene-1,2-dicarboxylate, (sec-butyl)(n-heptyl) 4-cyclohexene-1,2-dicarboxylate, (sec-butyl)(isoheptyl) 4-cyclohexene-1,2-dicarboxylate, (sec-butyl)(n-octyl) 4-cyclohexene-1,2-dicarboxylate, (sec-butyl)(2-ethylhexyl) 4-cyclohexene-1,2-dicarboxylate, (sec-butyl)(isooctyl) 4-cyclohexene-1,2-dicarboxylate, (sec-butyl)(2-octyl) 4-cyclohexene-1,2-dicarboxylate, (sec-butyl)(n-nonyl) 4-cyclohexene-1,2-dicarboxylate, (sec-butyl)(isononyl) 4-cyclohexene-1,2-dicarboxylate, (sec-butyl)(3,5,5-trimethylhexyl) 4-cyclohexene-1,2-dicarboxylate, (sec-butyl)(n-decyl) 4-cyclohexene-1,2-dicarboxylate, (sec-butyl)(isodecyl) 4-cyclohexene-1,2-dicarboxylate, (sec-butyl)(n-undecyl) 4-cyclohexene-1,2-dicarboxylate, (sec-butyl)(isoundecyl) 4-cyclohexene-1,2-dicarboxylate, (sec-butyl)(n-dodecyl) 4-cyclohexene-1,2-dicarboxylate, (sec-butyl)(isododecyl) 4-cyclohexene-1,2-dicarboxylate, (sec-butyl)(n-tridecyl) 4-cyclohexene-1,2-dicarboxylate, (sec-butyl)(isotridecyl) 4-cyclohexene-1,2-dicarboxylate, (sec-butyl)(n-tetradecyl) 4-cyclohexene-1,2-dicarboxy late, (sec-butyl)(isotetradecyl) 4-cyclohexene-1,2-dicarboxylate, (sec-butyl)(n-pentadecyl) 4-cyclohexene-1,2-dicarboxylate, (sec-butyl)(isopentadecyl) 4-cyclohexene-1,2-dicarboxylate, (sec-butyl)(n-hexadecyl) 4-cyclohexene-1,2-dicarboxylate, (sec-butyl)(isohexadecyl) 4-cyclohexene-1,2-dicarboxylate, (sec-butyl)(n-heptadecyl) 4-cyclohexene-1,2-dicarboxylate, (sec-butyl)(isoheptadecyl) 4-cyclohexene-1,2-dicarboxylate, (sec-butyl)(n-octadecyl) 4-cyclohexene-1,2-dicarboxylate, (sec-butyl)(isooctadecyl) 4-cyclohexene-1,2-dicarboxylate.

Recommendable are preferably (n-propyl) (cyclohexyl) 1,2-cyclohexanedicarboxylate, (n-propyl)(isoheptyl) 1,2-cyclohexanedicarboxylate, (n-propyl)(2-ethylhexyl) 1,2-cyclohexanedicarboxylate, (n-propyl)(isooctyl) 1,2-cyclohexanedicarboxylate, (n-propyl)(2-octyl) 1,2-cyclohexanedicarboxylate, (n-propyl)(isononyl) 1,2-cyclohexanedicarboxylate, (n-propyl) (3,5,5-trimethylhexyl) 1,2-cyclohexanedicarboxylate, (n-propyl) (isodecyl) 1,2-cyclohexanedicarboxylate, (n-propyl) (isoundecyl) 1,2-cyclohexanedicarboxylate, (n-propyl) (isododecyl) 1,2-cyclohexanedicarboxylate, (n-propyl) (isotridecyl) 1,2-cyclohexanedicarboxylate, (n-propyl) (isotetradecyl) 1,2-cyclohexanedicarboxylate, (n-propyl) (isopentadecyl) 1,2-cyclohexanedicarboxylate, (n-propyl) (isohexadecyl) 1,2-cyclohexanedicarboxylate, (n-propyl) (isoheptadecyl) 1,2-cyclohexanedicarboxylate, (n-propyl) (isooctadecyl) 1,2-cyclohexanedicarboxylate, (isopropyl) (cyclohexyl) 1,2-cyclohexanedicarboxylate, (isopropyl) (isoheptyl) 1,2-cyclohexanedicarboxylate, (isopropyl)(2-ethylhexyl) 1,2-cyclohexanedicarboxylate, (isopropyl) (isooctyl) 1,2-cyclohexanedicarboxylate, (isopropyl)(2-octyl) 1,2-cyclohexanedicarboxylate, (isopropyl)(isononyl) 1,2-cyclohexanedicarboxylate, (isopropyl)(3,5,5-trimethylhexyl) 1,2-cyclohexanedicarboxylate, (isopropyl)(isodecyl) 1,2-cyclohexanedicarboxylate, (isopropyl)(isoundecyl) 1,2-cyclohexanedicarboxylate, (isopropyl)(isododecyl) 1,2-cyclohexanedicarboxylate, (isopropyl)(isotridecyl) 1,2-cyclohexanedicarboxylate, (isopropyl)(isotetradecyl) 1,2-cyclohexanedicarboxylate, (isopropyl)(isopentadecyl) 1,2-cyclohexanedicarboxylate, (isopropyl)(isohexadecyl) 1,2-cyclohexanedicarboxylate, (isopropyl)(isoheptadecyl) 1,2-cyclohexanedicarboxylate, (isopropyl)(isooctadecyl) 1,2-cyclohexanedicarboxylate, (n-butyl)(cyclohexyl) 1,2-cyclohexanedicarboxylate, (n-butyl)(isoheptyl) 1,2-cyclohexanedicarboxylate, (n-butyl)(2-ethylhexyl) 1,2-cyclohexanedicarboxylate, (n-butyl)(isooctyl) 1,2-cyclohexanedicarboxylate, (n-butyl)(2-octyl) 1,2- cyclohexanedicarboxylate, (n-butyl)(isononyl) 1,2-cyclohexanedicarboxylate, (n-butyl)(3,5,5-trimethylhexyl) 1,2-cyclohexanedicarboxylate, (n-butyl)(isodecyl) 1,2-cyclohexanedicarboxylate, (n-butyl)(isoundecyl) 1,2-cyclohexanedicarboxylate, (n-butyl)(isododecyl) 1,2-cyclohexanedicarboxylate, (n-butyl)(isotridecyl) 1,2-cyclohexanedicarboxylate, (n-butyl)(isotetradecyl) 1,2-cyclohexanedicarboxylate, (n-butyl)(isopentadecyl) 1,2-cyclohexanedicarboxylate, (n-butyl)(isohexadecyl) 1,2-cyclohexanedicarboxylate, (n-butyl)(isoheptadecyl) 1,2-cyclohexanedicarboxylate, (n-butyl)(isooctadecyl) 1,2-cyclohexanedicarboxylate, (isobutyl)(cyclohexyl) 1,2-cyclohexanedicarboxylate, (isobutyl)(isoheptyl) 1,2-cyclohexanedicarboxylate, (isobutyl)(2-ethylhexyl) 1,2-cyclohexanedicarboxylate, (isobutyl)(isooctyl) 1,2-cyclohexanedicarboxylate, (isobutyl)(2-octyl) 1,2-cyclohexanedicarboxylate, (isobutyl)(isononyl) 1,2-cyclohexanedicarboxylate, (isobutyl)(3,5,5-trimethylhexyl) 1,2-cyclohexanedicarboxylate, (isobutyl)(isodecyl) 1,2-cyclohexanedicarboxylate, (isobutyl)(isoundecyl) 1,2-cyclohexanedicarboxylate, (isobutyl)(isododecyl) 1,2-cyclohexanedicarboxylate, (isobutyl)(isotridecyl) 1,2-cyclohexanedicarboxylate, (isobutyl)(isotetradecyl) 1,2-cyclohexanedicarboxylate, (isobutyl)(isopentadecyl) 1,2-cyclohexanedicarboxylate, (isobutyl)(isohexadecyl) 1,2-cyclohexanedicarboxylate, (isobutyl)(isoheptadecyl) 1,2-cyclohexanedicarboxylate, (isobutyl)(isooctadecyl) 1,2-cyclohexanedicarboxylate, (sec-butyl)(cyclohexyl) 1,2-cyclohexanedicarboxylate, (sec-butyl)(isoheptyl) 1,2-cyclohexanedicarboxylate, (sec-butyl)(2-ethylhexyl) 1,2-cyclohexanedicarboxylate, (sec-butyl)(isooctyl) 1,2-cyclohexanedicarboxylate, (sec-butyl)(2-octyl) 1,2-cyclohexanedicarboxylate, (sec-butyl)(isononyl) 1,2-cyclohexanedicarboxylate, (sec-butyl)(3,5,5-trimethylhexyl) 1,2-cyclohexanedicarboxylate, (sec-butyl)(isodecyl) 1,2-cyclohexanedicarboxylate, (sec-butyl)(isoundecyl) 1,2-cyclohexanedicarboxylate, (sec-butyl)(isododecyl) 1,2-cyclohexanedicarboxylate, (sec-butyl)(isotridecyl) 1,2-cyclohexanedicarboxylate, (sec-butyl)(isotetradecyl) 1,2-cyclohexanedicarboxylate, (sec-butyl)(isopentadecyl) 1,2-cyclohexanedicarboxylate, (sec-butyl)(isohexadecyl) 1,2-cyclohexanedicarboxylate, (sec-butyl)(isoheptadecyl) 1,2-cyclohexanedicarboxylate, (sec-butyl)(isooctadecyl) 1,2-cyclohexanedicarboxylate, (n-propyl)(cyclohexyl) 4-cyclohexene-1,2-dicarboxylate, (n-propyl)(isoheptyl) 4-cyclohexene-1,2-dicarboxylate, (n-propyl)(2-ethylhexyl) 4-cyclohexene-1,2-dicarboxylate, (n-propyl)(isooctyl) 4-cyclohexene-1,2-dicarboxylate, (n-propyl)(2-octyl) 4-cyclohexene-1,2-dicarboxylate, (n-propyl)(isononyl) 4-cyclohexene-1,2-dicarboxylate, (n-propyl)(3,5,5-trimethylhexyl) 4-cyclohexene-1,2-dicarboxylate, (n-propyl)(isodecyl) 4-cyclohexene-1,2-dicarboxylate, (n-propyl)(isoundecyl) 4-cyclohexene-1,2-dicarboxylate, (n-propyl)(isododecyl) 4-cyclohexene-1,2-dicarboxylate, (n-propyl)(isotridecyl) 4-cyclohexene-1,2-dicarboxylate, (n-propyl)(isotetradecyl) 4-cyclohexene-1,2-dicarboxylate, (n-propyl)(isopentadecyl) 4-cyclohexene-1,2-dicarboxylate, (n-propyl)(isohexadecyl) 4-cyclohexene-1,2-dicarboxylate, (n-propyl)(isoheptadecyl) 4-cyclohexene-1,2-dicarboxylate, (n-propyl)(isooctadecyl) 4-cyclohexene-1,2-dicarboxylate, (isopropyl)(cyclohexyl) 4-cyclohexene-1,2-dicarboxylate, (isopropyl)(isoheptyl) 4-cyclohexene-1,2-dicarboxylate, (isopropyl)(2-ethylhexyl) 4-cyclohexene-1,2-dicarboxylate, (isopropyl)(isooctyl) 4-cyclohexene-1,2-dicarboxylate, (isopropyl)(2-octyl) 4-cyclohexene-1,2-dicarboxylate, (isopropyl)(isononyl) 4-cyclohexene-1,2-dicarboxylate, (isopropyl)(3,5,5-trimethylhexyl) 4-cyclohexene-1,2-dicarboxylate, (isopropyl)(isodecyl) 4-cyclohexene-1,2-dicarboxylate, (isopropyl)(isoundecyl) 4-cyclohexene-1,2-dicarboxylate, (isopropyl)(isododecyl) 4-cyclohexene-1,2-dicarboxylate, (isopropyl)(isotridecyl) 4-cyclohexene-1,2-dicarboxylate, (isopropyl)(isotetradecyl) 4-cyclohexene-1,2-dicarboxylate, (isopropyl)(isopentadecyl) 4-cyclohexene-1,2-dicarboxylate, (isopropyl)(isohexadecyl) 4-cyclohexene-1,2-dicarboxylate, (isopropyl)(isoheptadecyl) 4-cyclohexene-1,2-dicarboxylate, (isopropyl)(isooctadecyl) 4-cyclohexene-1,2-dicarboxylate, (n-butyl)(cyclohexyl) 4-cyclohexene-1,2-dicarboxylate, (n-butyl)(isoheptyl) 4-cyclohexene-1,2-dicarboxylate, (n-butyl)(2-ethylhexyl) 4-cyclohexene-1,2-dicarboxylate, (n-butyl)(isooctyl) 4-cyclohexene-1,2-dicarboxylate, (n-butyl)(2-octyl) 4-cyclohexene-1,2-dicarboxylate, (n-butyl)(isononyl) 4-cyclohexene-1,2-dicarboxylate, (n-butyl)(3,5,5-trimethylhexyl) 4-cyclohexene-1,2-dicarboxylate, (n-butyl)(isodecyl) 4-cyclohexene-1,2-dicarboxylate, (n-butyl)(isoundecyl) 4-cyclohexene-1,2-dicarboxylate, (n-butyl)(isododecyl) 4-cyclohexene-1,2-dicarboxylate, (n-butyl)(isotridecyl) 4-cyclohexene-1,2-dicarboxylate, (n-butyl)(isotetradecyl) 4-cyclohexene-1,2-dicarboxylate, (n-butyl)(isopentadecyl) 4-cyclohexene-1,2-dicarboxylate, (n-butyl)(isohexadecyl) 4-cyclohexene-1,2-dicarboxylate, (n-butyl)(isoheptadecyl) 4-cyclohexene-1,2-dicarboxylate, (n-butyl)(isooctadecyl) 4-cyclohexene-1,2-dicarboxylate, (isobutyl)(cyclohexyl) 4-cyclohexene-1,2-dicarboxylate, (isobutyl)(isoheptyl) 4-cyclohexene-1,2-dicarboxylate, (isobutyl)(2-ethylhexyl) 4-cyclohexene-1,2-dicarboxylate, (isobutyl)(isooctyl) 4-cyclohexene-1,2-dicarboxylate, (isobutyl)(2-octyl) 4-cyclohexene-1,2-dicarboxylate, (isobutyl)(isononyl) 4-cyclohexene-1,2-dicarboxylate, (isobutyl)(3,5,5-trimethylhexyl) 4-cyclohexene-1,2-dicarboxylate, (isobutyl)(isodecyl) 4-cyclohexene-1,2-dicarboxylate, (isobutyl)(isoundecyl) 4-cyclohexene-1,2-dicarboxylate, (isobutyl)(isododecyl) 4-cyclohexene-1,2-dicarboxylate, (isobutyl)(isotridecyl) 4-cyclohexene-1,2-dicarboxylate, (isobutyl)(isotetradecyl) 4-cyclohexene-1,2-dicarboxylate, (isobutyl)(isopentadecyl) 4-cyclohexene-1,2-dicarboxylate, (isobutyl)(isohexadecyl) 4-cyclohexene-1,2-dicarboxylate, (isobutyl)(isoheptadecyl) 4-cyclohexene-0,1,2-dicarboxylate, (isobutyl)(isooctadecyl) 4-cyclohexene-1,2-dicarboxylate, (sec-butyl)(cyclohexyl) 4-cyclohexene-1,2-dicarboxylate, (sec-butyl)(isoheptyl) 4-cyclohexene-1,2-dicarboxylate, (sec-butyl)(2-ethylhexyl) 4-cyclohexene-1,2-dicarboxylate, (sec-butyl)(isooctyl) 4-cyclohexene-1,2-dicarboxylate, (sec-butyl)(2-octyl) 4-cyclohexene-1,2-dicarboxylate, (sec-butyl)(isononyl) 4-cyclohexene-1,2-dicarboxylate, (sec-butyl)(3,5,5-trimethylhexyl) 4-cyclohexene-1,2-dicarboxylate, (sec-butyl)(isodecyl) 4-cyclohexene-1,2-dicarboxylate, (sec-butyl)(isoundecyl) 4-cyclohexene-1,2-dicarboxylate, (sec-butyl)(isododecyl) 4-cyclohexene-1,2-dicarboxylate, (sec-butyl)(isotridecyl) 4-cyclohexene-1,2-dicarboxylate, (sec-butyl)(isotetradecyl) 4-cyclohexene-1,2-dicarboxylate, (sec-butyl)(isopentadecyl) 4-cyclohexene-1,2-dicarboxylate, (sec-butyl)(isohexadecyl) 4-cyclohexene-1,2-dicarboxylate, (sec-butyl)(isoheptadecyl) 4-cyclohexene-1,2-dicarboxylate, (sec-butyl)(isooctadecyl) 4-cyclohexene-1,2-dicarboxylate.

Specific examples of the aromatic adjacent dicarboxylic acid mixed diester of the formula (4) are (methyl)(cyclohexyl)phthalate, (methyl)(n-heptyl)phthalate, (methyl)(isoheptyl)phthalate, (methyl)(n-octyl)phthalate, (methyl)(2-ethylhexyl)phthalate, (methyl)(isooctyl)phthalate, (methyl)(2-octyl)phthalate, (methyl)(n-nonyl)phthalate, (methyl)(isononyl)phthalate, (methyl)(3,5,5-trimethylhexyl)phthalate, (methyl)(n-decyl)phthalate, (methyl)(isodecyl)phthalate, (methyl)(n-undecyl)phthalate, (methyl)

(isoundecyl)phthalate, (methyl)(n-dodecyl)phthalate, (methyl)(isododecyl)phthalate, (methyl)(n-tridecyl)phthalate, (methyl) (isotridecyl)phthalate, (methyl)(n-tetradecyl)phthalate, (methyl)(isotetradecyl)phthalate, (methyl)(n-pentadecyl)phthalate, (methyl)(isopentadecyl)phthalate, (methyl) (n-hexadecyl)phthalate, (methyl)(isohexadecyl)phthalate, (methyl)(n-heptadecyl)phthalate, (methyl)(isoheptadecyl)phthalate, (methyl)(n-octadecyl)phthalate, (methyl) (isooctadecyl)phthalate, (ethyl)(cyclohexyl)phthalate, (ethyl)(n-heptyl)phthalate, (ethyl)(isoheptyl)phthalate, (ethyl)(n-octyl)phthalate, (ethyl)(2-ethylhexyl)phthalate, (ethyl) (isooctyl)phthalate, (ethyl)(2-octyl)phthalate, (ethyl)(n-nonyl)phthalate, (ethyl)(isononyl)phthalate, (ethyl)(3,5,5-trimethylhexyl)phthalate, (ethyl)(n-decyl)phthalate, (ethyl) (isodecyl)phthalate, (ethyl)(n-undecyl)phthalate, (ethyl) (isoundecyl)phthalate, (ethyl)(n-dodecyl)phthalate, (ethyl) (isododecyl)phthalate, (ethyl)(n-tridecyl)phthalate, (ethyl) (isotridecyl)phthalate, (ethyl)(n-tetradecyl)phthalate, (ethyl) (isotetradecyl)phthalate, (ethyl)(n-pentadecyl)phthalate, (ethyl)(isopentadecyl)phthalate, (ethyl)(n-hexadecyl)phthalate, (ethyl)(isohexadecyl)phthalate, (ethyl)(n-heptadecyl) phthalate, (ethyl)(isoheptadecyl)phthalate, (ethyl)(n-octadecyl)phthalate, (ethyl)(isooctadecyl)phthalate, (n-propyl) (cyclohexyl)phthalate, (n-propyl)(n-heptyl)phthalate, (n-propyl) (isoheptyl)phthalate, (n-propyl)(n-octyl)phthalate, (n-propyl)(2-ethylhexyl)phthalate, (n-propyl) (isooctyl) phthalate, (n-propyl)(2-octyl)phthalate, (n-propyl) (n-nonyl) phthalate, (n-propyl)(isononyl)phthalate, (n-propyl)(3,5,5-trimethylhexyl)phthalate, (n-propyl) (n-decyl)phthalate, (n-propyl)(isodecyl)phthalate, (n-propyl)(n-undecyl)phthalate, (n-propyl)(isoundecyl)phthalate, (n-propyl)(n-dodecyl) phthalate, (n-propyl) (isododecyl)phthalate, (n-propyl)(n-tridecyl)phthalate, (n-propyl)(isotridecyl)phthalate, (n-propyl)(n-tetradecyl)phthalate, (n-propyl)(isotetradecyl) phthalate, (n-propyl) (n-pentadecyl)phthalate, (n-propyl) (isopentadecyl)phthalate, (n-propyl)(n-hexadecyl)phthalate, (n-propyl) (isohexadecyl)phthalate, (n-propyl)(n-heptadecyl)phthalate, (n-propyl)(isoheptadecyl)phthalate, (n-propyl) (n-octadecyl)phthalate, (n-propyl)(isooctadecyl)phthalate, (isopropyl)(cyclohexyl)phthalate, (isopropyl)(n-heptyl) phthalate, (isopropyl)(isoheptyl)phthalate, (isopropyl) (n-octyl)phthalate, (isopropyl)(2-ethylhexyl)phthalate, (isopropyl)(isooctyl)phthalate, (isopropyl)(2-octyl)phthalate, (isopropyl)(n-nonyl)phthalate, (isopropyl) (isononyl)phthalate, (isopropyl)(3,5,5-trimethylhexyl)phthalate, (isopropyl) (n-decyl)phthalate, (isopropyl) (isodecyl)phthalate, (isopropyl)(n-undecyl)phthalate, (isopropyl)(isoundecyl)phthalate, (isopropyl)(n-dodecyl)phthalate, (isopropyl)(isododecyl)phthalate, (isopropyl) (n-tridecyl)phthalate, (isopropyl)(isotridecyl)phthalate, (isopropyl)(n-tetradecyl)phthalate, (isopropyl) (isotetradecyl)phthalate, (isopropyl)(n-pentadecyl) phthalate, (isopropyl)(isopentadecyl)phthalate, (isopropyl) (n-hexadecyl)phthalate, (isopropyl) (isohexadecyl) phthalate, (isopropyl)(n-heptadecyl)phthalate, (isopropyl) (isoheptadecyl)phthalate, (isopropyl)(n-octadecyl)phthalate, (isopropyl) (isooctadecyl)phthalate, (n-butyl)(cyclohexyl) phthalate, (n-butyl)(n-heptyl)phthalate, (n-butyl)(isoheptyl) phthalate, (n-butyl)(n-octyl)phthalate, (n-butyl)(2-ethylhexyl)phthalate, (n-butyl)(isooctyl)phthalate, (n-butyl)(2-octyl)phthalate, (n-butyl)(n-nonyl)phthalate, (n-butyl) (isononyl)phthalate, (n-butyl)(3,5,5-trimethylhexyl) phthalate, (n-butyl)(n-decyl)phthalate, (n-butyl)(isodecyl) phthalate, (n-butyl)(n-undecyl)phthalate, (n-butyl) (isoundecyl)phthalate, (n-butyl)(n-dodecyl)phthalate, (n-butyl)(isododecyl)phthalate, (n-butyl)(n-tridecyl)phthalate, (n-butyl)(isotridecyl)phthalate, (n-butyl)(n-tetradecyl) phthalate, (n-butyl)(isotetradecyl)phthalate, (n-butyl)(n-pentadecyl)phthalate, (n-butyl)(isopentadecyl)phthalate, (n-butyl)(n-hexadecyl)phthalate, (n-butyl)(isohexadecyl)phthalate, (n-butyl)(n-heptadecyl)phthalate, (n-butyl)(isoheptadecyl)phthalate, (n-butyl)(n-octadecyl)phthalate, (n-butyl) (isooctadecyl)phthalate, (isobutyl)(cyclohexyl)phthalate, (isobutyl)(n-heptyl)phthalate, (isobutyl)(isoheptyl)phthalate, (isobutyl)(n-octyl)phthalate, (isobutyl)(2-ethylhexyl) phthalate, (isobutyl)(isooctyl)phthalate, (isobutyl)(2-octyl) phthalate, (isobutyl)(n-nonyl)phthalate, (isobutyl)(isononyl) phthalate, (isobutyl)(3,5,5-trimethylhexyl)phthalate, (isobutyl)(n-decyl)phthalate, (isobutyl)(isodecyl)phthalate, (isobutyl)(n-undecyl)phthalate, (isobutyl)(isoundecyl)phthalate, (isobutyl)(n-dodecyl)phthalate, (isobutyl)(isododecyl)phthalate, (isobutyl)(n-tridecyl)phthalate, (isobutyl) (isotridecyl)phthalate, (isobutyl)(n-tetradecyl)phthalate, (isobutyl)(isotetradecyl)phthalate, (isobutyl)(n-pentadecyl) phthalate, (isobutyl)(isopentadecyl)phthalate, (isobutyl)(n-hexadecyl)phthalate, (isobutyl)(isohexadecyl)phthalate, (isobutyl)(n-heptadecyl)phthalate, (isobutyl)(isoheptadecyl) phthalate, (isobutyl)(n-octadecyl)phthalate, (isobutyl) (isooctadecyl)phthalate, (sec-butyl)(cyclohexyl)phthalate, (sec-butyl)(n-heptyl)phthalate, (sec-butyl)(isoheptyl)phthalate, (sec-butyl)(n-octyl)phthalate, (sec-butyl)(2-ethylhexyl) phthalate, (sec-butyl)(isooctyl)phthalate, (sec-butyl)(2-octyl) phthalate, (sec-butyl)(n-nonyl)phthalate, (sec-butyl) (isononyl)phthalate, (sec-butyl)(3,5,5-trimethylhexyl) phthalate, (sec-butyl)(n-decyl)phthalate, (sec-butyl) (isodecyl)phthalate, (sec-butyl)(n-undecyl)phthalate, (sec-butyl)(isoundecyl)phthalate, (sec-butyl)(n-dodecyl) phthalate, (sec-butyl)(isododecyl)phthalate, (sec-butyl)(n-tridecyl)phthalate, (sec-butyl)(isotridecyl)phthalate, (sec-butyl)(n-tetradecyl)phthalate, (sec-butyl)(isotetradecyl) phthalate, (sec-butyl)(n-pentadecyl)phthalate, (sec-butyl) (isopentadecyl)phthalate, (sec-butyl)(n-hexadecyl) phthalate, (sec-butyl)(isohexadecyl)phthalate, (sec-butyl)(n-heptadecyl)phthalate, (sec-butyl)(isoheptadecyl)phthalate, (sec-butyl)(n-octadecyl)phthalate, (sec-butyl)(isooctadecyl) phthalate, and recommended are preferably (n-propyl)(cyclohexyl)phthalate, (n-propyl)(isoheptyl)phthalate, (n-propyl)(2-ethylhexyl)phthalate, (n-propyl)(isooctyl)phthalate, (n-propyl)(2-octyl)phthalate, (n-propyl)(isononyl)phthalate, (n-propyl)(3,5,5-trimethylhexyl)phthalate, (n-propyl)(isodecyl)phthalate, (n-propyl)(isoundecyl)phthalate, (n-propyl) (isododecyl)phthalate, (n-propyl)(isotridecyl)phthalate, (n-propyl)(isotetradecyl)phthalate, (n-propyl)(isopentadecyl)phthalate, (n-propyl)(isohexadecyl)phthalate, (n-propyl) (isoheptadecyl)phthalate, (n-propyl)(isooctadecyl)phthalate, (isopropyl)(cyclohexyl)phthalate, (isopropyl)(isoheptyl)phthalate, (isopropyl)(2-ethylhexyl)phthalate, (isopropyl) (isooctyl)phthalate, (isopropyl)(2-octyl)phthalate, (isopropyl)(isononyl)phthalate, (isopropyl)(3,5,5-trimethylhexyl) phthalate, (isopropyl)(isodecyl)phthalate, (isopropyl) (isoundecyl)phthalate, (isopropyl)(isododecyl)phthalate, (isopropyl)(isotridecyl)phthalate, (isopropyl)(isotetradecyl) phthalate, (isopropyl)(isopentadecyl)phthalate, (isopropyl) (isohexadecyl)phthalate, (isopropyl)(isoheptadecyl)phthalate, (isopropyl)(isooctadecyl)phthalate, (n-butyl) (cyclohexyl)phthalate, (n-butyl)(isoheptyl)phthalate, (n-butyl)(2-ethylhexyl)phthalate, (n-butyl)(isooctyl)phthalate, (n-butyl)(2-octyl)phthalate, (n-butyl)(isononyl)phthalate, (n-butyl)(3,5,5-trimethylhexyl)phthalate, (n-butyl)(isodecyl)phthalate, (n-butyl)(isoundecyl)phthalate, (n-butyl) (isododecyl)phthalate, (n-butyl)(isotridecyl)phthalate, (n-butyl)(isotetradecyl)phthalate, (n-butyl) (isopentadecyl) phthalate, (n-butyl) (isohexadecyl)phthalate, (n-butyl)(isoheptadecyl)phthalate, (n-butyl)(isooctadecyl)phthalate, (isobutyl)(cyclohexyl)phthalate, (isobutyl)(isoheptyl)phthalate, (isobutyl)(2-ethylhexyl)phthalate, (isobutyl) (isooctyl) phthalate, (isobutyl)(2-octyl)phthalate, (isobutyl)(isononyl) phthalate, (isobutyl)(3,5,5-trimethylhexyl)phthalate, (isobutyl)(isodecyl)phthalate, (isobutyl)(isoundecyl)phthalate, (isobutyl)(isododecyl)phthalate, (isobutyl)(isotridecyl) phthalate, (isobutyl)(isotetradecyl)phthalate, (isobutyl)(isopentadecyl)phthalate, (isobutyl)(isohexadecyl)phthalate, (isobutyl)(isoheptadecyl)phthalate, (isobutyl)(isooctadecyl) phthalate, (sec-butyl)(cyclohexyl)phthalate, (sec-butyl)(isoheptyl)phthalate, (sec-butyl)(2-ethylhexyl)phthalate, (sec-butyl)(isooctyl)phthalate, (sec-butyl)(2-octyl)phthalate, (sec-butyl)(isononyl)phthalate, (sec-butyl)(3,5,5-trimethylhexyl)phthalate, (sec-butyl)(isodecyl)phthalate, (sec-butyl) (isoundecyl)phthalate, (sec-butyl)(isododecyl)phthalate, (sec-butyl)(isotridecyl)phthalate, (sec-butyl)(isotetradecyl) phthalate, (sec-butyl) (isopentadecyl)phthalate, (sec-butyl) (isohexadecyl)phthalate, (sec-butyl)(isoheptadecyl)phthalate, (sec-butyl)(isooctadecyl)phthalate.

Among the foregoing alicyclic or aromatic adjacent dicarboxylic acid mixed diesters, the alicyclic adjacent dicarboxylic mixed diesters represented by the formula (4) wherein A is a cyclohexane ring or a cyclohexene ring has a high hydrolysis stability and is preferred. Among such alicyclic adjacent dicarboxylic acid mixed diesters represented by the formula (4), preferable are those wherein $R^5$ is a straight-chain alkyl group having 1 to 5 carbon atoms or a branched-chain alkyl group having 3 to 5 carbon atoms, and $R^6$ is a straight-chain or branched chain alkyl group having 6 to 11 carbon atoms. Particularly preferable are alicyclic adjacent dicarboxylic acid mixed diesters represented by the formula (4) wherein A is a cyclohexane ring or cyclohexene ring, X is a hydrogen atom, $R^5$ is a straight-chain alkyl group having 1 to 5 carbon atoms or a branched-chain alkyl group having 3 to 5 carbon atoms, and $R^6$ is a straight-chain or branched chain alkyl group having 6 to 11 carbon atoms.

When A is a cyclohexene ring, the group —$COOR^5$ and the group —$COOR^6$ are preferably present at the 1- and 2-positions and the double bond is present between the 4- and 5-positions.

Among them, more preferred in view of hydrolysis stability, heat stability, miscibility with a refrigerant, electrical insulating property and lubricity are (isopropyl) (2-ethylhexyl) 1,2-cyclohexanedicarboxylate, (isopropyl) (isononyl) 1,2-cyclohexanedicarboxylate, (isopropyl) (3,5,5-trimethylhexyl) 1,2-cyclohexanedicarboxylate, (isobutyl) (2-ethylhexyl) 1,2-cyclohexanedicarboxylate, (isobutyl) (isononyl) 1,2-cyclohexanedicarboxylate, (isobutyl) (3,5,5-trimethylhexyl) 1,2-cyclohexanedicarboxylate, (isopropyl) (2-ethylhexyl) 4-cylochexene-1,2-dicarboxylate, (isopropyl) (isononyl) 4-cyclohexene-1,2-dicarboxylate, (isopropyl) (3,5,5-trimethylhexyl) 4-cyclohexene-1,2-dicarboxylate, (isobutyl) (2-ethylhexyl) 4-cyclohexene-1,2-dicarboxylate, (isobutyl) (isononyl) 4-cyclohexene-1,2-dicarboxylate, and (isobutyl) (3,5,5-trimethylhexyl) 4-cyclohexene-1,2-dicarboxylate.

The cyclohexane adjacent dicarboxylic acid mixed diester can also be prepared by completely hydrogenating the aromatic ring of the aromatic adjacent dicarboxylic acid mixed diester of the invention (hydrogenation of nucleus). The cyclohexene adjacent dicarboxylic acid mixed diester can be prepared by partly hydrogenating the aromatic ring of the aromatic adjacent dicarboxylic acid mixed diester.

The alicyclic adjacent dicarboxylic acid mixed diesters of the invention include position isomers ascribed to ester groups. For example, 4-cyclohexene-1,2-dicarboxylic acid diester may be an isomer depending on whether two ester groups are present in equatorial or axial positions. Specifically, the diester is a cis isomer when one of its two ester groups is in the equatorial position and the other is present in the axial position. The diester is a trans isomer when both of its two ester groups are present in the equatorial position or in the axial position. All of these isomers can be used for use in a refrigerator oil.

When esterification temperature is set to higher than 210° C. and up to about 230° C. in the second stage esterification for the preparation of the alicyclic adjacent dicarboxylic acid mixed diester, the esterification tends to predominantly give a trans isomer, whereas when esterification temperature is set at about 160 to about 210° C., the esterification tends to predominantly give a cis isomer.

A cis-form ester can be isomerized to a trans-form ester. Isomerization can be performed according to the method disclosed, for example, in U.S. Pat. No. 5,231,218.

As to the ratio of the isomers, it is desirable that trans isomer/cis isomer ratio is 0/100 to 80/20 (by area % as determined by gas chromatography). More preferably, the trans isomer/cis isomer ratio is 20/80 to 80/20 (by area % as determined by gas chromatography) in view of hydrolysis stability, electrical insulating property and miscibility with a refrigerant. The conditions under which gas chromatography is conducted will be described in Examples.

Process for Preparing an Ester of Embodiment II

Step (a): First-stage Esterification Reaction

The alicyclic or aromatic adjacent dicarboxylic anhydride to be used as the raw material (hereinafter referred to as "acid component 1") is represented by the formula (5s)

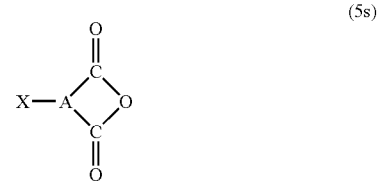

(5s)

wherein A and X are as defined above, and examples thereof are 1,2-cyclohexanedicarboxylic anhydride, cyclohexene-1,2-dicarboxylic anhydride, methyl-substituted 1,2-cyclohexanedicarboxylic anhydride, methyl-substituted cyclohexene-1,2-dicarboxylic anhydride and phthalic anhydride.

While the position of double bond in cyclohexenedicarboxylic annhydride may be any position relative to its acid anhydride group (—CO—O—CO—) without specific limitation, from the standpoint of hydrolysis stability, one wherein the acid anhydride group (—CO—O—CO—) is attached to the 1,2-positions and the double bond is present between 4- and 5-positions is preferable.

Specific examples of the alicyclic or aromatic adjacent dicarboxylic anhydride to be used herein are 1,2-cyclohexanedicarboxylic anhydride, 4-cyclohexene-1,2-dicarboxylic anhydride, 1-cyclohexene-1,2-dicarboxylic anhydride, 3-methyl-1,2-cyclohexanedicarboxylic anhydride, 4-methyl-1,2-cyclohexanedicarboxylic anhydride, 3-methyl-4-cyclohexene-1,2-dicarboxylic anhydride, 4-methyl-4-cyclohexene-1,2-dicarboxylic anhydride and phthalic anhyride.

In esterification, the above alicyclic or aromatic adjacent dicarboxylic anhydrides can be used either alone or in combination.

In carrying out the first-stage esterification reaction, "alcohol component 1" is used in an amount of 0.5 to 1.5 moles, preferably 0.8 to 1.2 moles, per mole of acid component 1. "Alcohol component 1" may be a single alcohol or an alcohol mixture. "Alcohol component 1" comprises a monohydric alcohol of 1 to 5 carbon atoms (P) and optionally a monohydric alcohol of 6 to 18 carbon atoms (Q) wherein (P):(Q) mole ratio is 0.1:99.9 to 100:0 (mole ratio). It is recommended that the mole ratio of the monohydric alcohol of 1 to 5 carbon atoms (P):the monohydric alcohol of 6 to 18 carbon atoms (Q) is preferably (P):(Q)=5:95 to 100:0 (mole ratio), in particular (P):(Q)=40:60 to 100:0.

The first-stage esterification reaction can be effected in the absence of a catalyst or in the presence of a sulfur-free and phosphorus-free catalyst, preferably in the absence of a catalyst.

The sulfur-free and phosphorus-free catalyst for use is a catalyst which do not contain a sulfur element and a phosphorus element in the elements constituting the catalyst. Specifically, examples of the catalyst are Lewis acids and alkali metals, etc. which do not contain a sulfur element or a phosphorus element. More specifically, examples of Lewis acids are aluminum derivatives, tin derivatives, titanium derivatives, lead derivatives and zinc derivatives. Examples of alkali metals are sodium alkoxide, potassium alkoxide, sodium hydroxide, potassium hydroxide, etc. These catalysts can be used either alone or in combination. Preferred catalysts are those which also do not contain a sulfur element and phosphorus element as impurities.

Among such catalysts, it is particularly preferable to use tetra($C_3$-$C_8$ alkyl) titanate, titanium oxide, titanium hydroxide, sodium alkoxide of 1 to 4 carbon atoms, sodium hydroxide, $C_3$-$C_{12}$ fatty acid tin salt, tin oxide, tin hydroxide, zinc oxide, zinc hydroxide, lead oxide, lead hydroxide, aluminum oxide and aluminum hydroxide. The amount of the catalyst to be used is, for example, about 0.05 to about 1 wt. % based on the total amount of acid component 1 and alcohol component 1 used as the raw materials for synthesis of the ester.

The reaction temperature for the first-stage esterification is, for example, 110 to 150° C. and the reaction is usually carried out for 0.5 to 3 hours.

In the first-stage esterification reaction, theoretically 1 mole of the acid anhydride can react with 1 mole of "alcohol component 1" to give the alicyclic or aromatic adjacent dicarboxylic acid monoester of the formula (5). In the course of the reaction, there is produced a small amount of a diester such as alicyclic or aromatic adjacent dicarboxylic acid mixed diester. In other words, actually the reaction product of first-stage esterification reaction may contain a diester in addition to the monoester of the formula (5). Possibly the reaction product further contains the acid anhydride, dicarboxylic acid, and alcohol used as the raw materials. In the specification, the term "a first reaction mixture" is used to include the above reaction product possibly containing these substances. The composition thereof can be analyzed by gas chromatography.

The reaction pressure in the esterification reaction is not particularly limited, and may be atmospheric pressure or reduced pressure (e.g., 133 to 66500 Pa). However, it is recommended to carry out the esterification reaction under atmospheric pressure from the standpoint of giving the alicyclic or aromatic adjacent dicarboxylic acid monoester represented by the formula (5) with high selectivity.

When an oxide, peroxide, carbonyl compound and like oxygen-containing organic compounds are produced in the exterification reaction due to oxidative deterioration of the raw materials, the obtained ester and the organic solvent (water-entraining agent), the hygroscopicity, hydrolysis stability and electrical insulating property would be adversely affected. Consequently, the reaction is preferably carried out in an atmosphere or stream of inert gas such as nitrogen gas.

Step (b): Second-stage Esterification Reaction

The first reaction mixture containing the alicyclic or aromatic adjacent dicarboxylic acid monoester of the formula (5) prepared in the first-stage is esterified with "alcohol component 2" to produce a reaction mixture (hereinafter referred to as "a second reaction mixture") containing an alicyclic or aromatic adjacent dicarboxylic acid mixed diester of the formula (4).

The second-stage esterification reaction can be conducted after the alicyclic or aromatic adjacent dicarboxylic acid monoester of the formula (5) is isolated from the reaction product. The isolation can be performed by conventional methods such as distillation, liquid-liquid extraction, column chromatography or the like. However, in view of economy, it is desirable to continuously conduct the first-stage and second-stage esterification reactions without isolation of the alicyclic or aromatic adjacent dicarboxylic acid monoester of the formula (5).

Specific examples of the alicyclic or aromatic adjacent dicarboxylic acid monoester of the formula (5) are monomethyl 1,2-cyclohexanedicarboxylate, monoethyl 1,2-cyclohexanedicarboxylate, mono(n-propyl) 1,2-cyclohexanedicarboxylate, monoisopropyl 1,2-cyclohexanedicarboxylate, mono(n-butyl) 1,2-cyclohexanedicarboxylate, monoisobutyl 1,2-cyclohexanedicarboxylate, mono(sec-butyl) 1,2-cyclohexanedicarboxylate, mono(n-heptyl) 1,2-cyclohexanedicarboxylate, monoisoheptyl 1,2-cyclohexanedicarboxylate, mono(n-octyl) 1,2-cyclohexanedicarboxylate, mono(2-ethylhexyl) 1,2-cyclohexanedicarboxylate, mono(2-octyl) 1,2-cyclohexanedicarboxylate, monoisooctyl 1,2-cyclohexanedicarboxylate, mono(n-nonyl) 1,2-cyclohexanedicarboxylate, monoisononyl 1,2-cyclohexanedicarboxylate, mono(3,5,5-trimethylhexyl) 1,2-cyclohexanedicarboxylate, mono(n-decyl) 1,2-cyclohexanedicarboxylate, monoisodecyl 1,2-cyclohexanedicarboxylate, mono(n-undecyl) 1,2-cyclohexanedicarboxylate, monoisoundecyl 1,2-cyclohexanedicarboxylate, mono(n-dodecyl) 1,2-cyclohexanedicarboxylate, monoisododecyl 1,2-cyclohexanedicarboxylate, mono(n-tridecyl) 1,2-cyclohexanedicarboxylate, monoisotridecyl 1,2-cyclohexanedicarboxylate, mono(n-tetradecyl) 1,2-cyclohexanedicarboxylate, monoisotetradecyl 1,2-cyclohexanedicarboxylate, mono(n-pentadecyl) 1,2-cyclohexanedicarboxylate, monoisopentadecyl 1,2-cyclohexanedicarboxylate, mono(n-hexadecyl) 1,2-cyclohexanedicarboxylate, monoisohexadecyl 1,2-cyclohexanedicarboxylate, mono(n-heptadecyl) 1,2-cyclohexanedicarboxylate, monoisoheptadecyl 1,2-cyclohexanedicarboxylate, mono(n-octadecyl) 1,2-cyclohexanedicarboxylate, monoisooctadecyl 1,2-cyclohexanedicarboxylate, monocyclohexyl 1,2-cyclohexanedicarboxylate, monomethyl 4-cyclohexene-1,2-dicarboxylate, monoethyl 4-cyclohexene-1,2-dicarboxylate, mono(n-propyl) 4-cyclohexene-1,2-dicarboxylate, monoisopropyl 4-cyclohexene-1,2-dicarboxylate, mono(n-butyl) 4-cyclohexene-1,2-dicarboxylate, monoisobutyl 4-cyclohexene-1,2-dicarboxylate, mono(sec-butyl) 4-cyclohexene-1,2-dicarbosylate, mono(n-heptyl) 4-cyclohexene-1,2-dicarboxylate, monoisoheptyl 4-cyclohexene-1,2-dicarboxylate, mono(n-octyl) 4-cyclohexene-1,2-dicarboxylate, mono(2-ethylhexyl) 4-cyclohexene-1,2-dicarboxylate, mono(2-octyl) 4-cyclohexene-1,2-dicarboxylate, monoisooctyl 4-cyclohexene-1,2-dicarboxylate, mono(n-nonyl) 4-cyclohexene-1,2-dicarboxylate, monoisononyl 4-cyclohexene-1,2-dicarboxylate, mono(3,5,5-trimethylhexyl) 4-cyclohexene-1,2-dicarboxylate, mono(n-decyl) 4-cyclohexene-1,2-dicarboxylate, monoisodecyl 4-cyclohexene-1,2-dicarboxylate, mono(n-undecyl) 4-cyclohexene-1,2-dicarboxylate, monoisoundecyl 4-cyclohexene-1,2-dicarboxylate, mono(n-dodecyl) 4-cyclohexene-1,2-dicarboxylate, monoisododecyl 4-cyclohexene-1,2-dicarboxylate, mono(n-tridecyl) 4-cyclohexene-1,2-dicarboxylate, monoisotridecyl 4-cyclohexene-1,2-dicarboxylate, mono(n-tetradecyl) 4-cyclohexene-1,2-dicarboxylate, monoisotetradecyl 4-cyclohexene-1,2-dicarboxylate, mono(n-pentadecyl) 4-cyclohexene-1,2-dicarboxylate, monoisopentadecyl 4-cyclohexene-1,2-dicarboxylate, mono(n-hexadecyl) 4-cyclohexene-1,2-dicarboxylate, monoisohexadecyl 4-cyclohexene-1,2-dicarboxylate, mono(n-heptadecyl) 4-cyclohexene-1,2-dicarboxylate, monoisoheptadecyl 4-cyclohexene-1,2-dicarboxylate, mono(n-octadecyl) 4-cyclohexene-1,2-dicarboxylate, monoisooctadecyl 4-cyclohexene-1,2-dicarboxylate, monocyclohexyl-4-cyclohexene-1,2-dicarboxylate, monomethyl phthalate, monoethyl phthalate, mono(n-propyl)phthale, monoisopropyl phthalate, mono(n-butyl)phthalate, monoisobutyl phthalate, mono(sec-butyl) phthalate, mono(n-heptyl)phthalate, monoisoheptyl phthalate, mono(n-octyl)phthalate, mono(2-ethylhexyl)phthalate, mono(2-octyl)phthalate, monoisooctyl phthalate, mono(n-nonyl)phthalate, monoisononyl phthalate, mono(3,5,5-trimethylhexyl)phthalate, mono(n-decyl)phthalate, monoisodecyl phthalate, mono(n-undecyl)phthalate, monoisoundecyl phthalate, mono(n-dodecyl)phthalate, monoisododecyl phthalate, mono(n-tridecyl)phthalate, monoisotridecyl phthalate, mono(n-tetradecyl)phthalate, monoisotetradecyl phthalate, mono(n-pentadecyl)phthalate, monoisopentadecyl phthalate, mono(n-hexadecyl)phthalate, monoisohexadecyl phthalate, mono(n-heptadecyl)phthalate, monoisoheptadecyl phthalate, mono(n-octadecyl)phthalate, monoisooctadecyl phthalate, monocyclohexyl phthalate, etc.

In the alicyclic or aromatic adjacent dicarboxylic acid monoester of the formula (5), the positions of the ester group and free carboxylic acid group are not limited. Thus, for example, when the ester group is present at the 1-position, the free carboxylic acid group is present in the 2-position, and when the ester group is present at the 2-position, the free carboxylic acid group is present in the 1-position.

The first reaction mixture containing the alicyclic or aromatic adjacent dicarboxylic acid monoester of the formula (5) further contains, for example in the case of isobutyl ester, monoisobutyl 1,2-cyclohexanedicarboxylate, diisobutyl 1,2-cyclohexanedicarboxylate, isobutanol, 1,2-cyclohexanedicarboxlic anhydride, 1,2-cyclohexanedicarboxylic acid, etc.

In the second stage esterification reaction, "alcohol component 2" is used. "Alcohol component 2" may be a single alcohol or a mixture of alcohols, and comprises a monohydric alcohol of 6 to 18 carbon atoms (T) and optionally a monohydric alcohol of 1 to 5 carbon atoms (S) wherein (S):(T) mole ratio is 0:100 to 99.9:0.1 (mole ratio). It is recommended that the mole ratio of the monohydric alcohol of 1 to 5 carbon atoms (S): the monohydric alcohol of 6 to 18 carbon atoms (T) is (S):(T)=0:100 to 95:5 (mole ratio), especially (S):(T)=0:100 to 40:60 (mole ratio).

Examples of the monohydric alcohol of 1 to 5 carbon atoms (S) are methanol, ethanol, n-propanol, isopropanol, n-butanol, isobutanol, sec-butanol, n-pentanol, isopentanol and like aliphatic monohydric alcohols of 1 to 5 carbon atoms, cyclopropanol, cyclobutanol, cyclopentanol and like alicyclic monohydric alcohols of 3 to 5 carbon atoms and the like. These alcohols can be used either alone or in combination. Among them, monohydric alcohols of 3 to 5 carbon atoms are preferable to improve the lubricity.

Examples of the monohydric alcohol of 6 to 18 carbon atoms (T) to be used herein are n-hexanol, isohexanol, n-heptanol, 2-methylhexanol, isoheptanol, n-octanol, 2-ethylhexanol, 2-octanol, isooctanol, 2-methylheptanol, n-nonanol, isononanol, 3,5,5-trimethylhexanol, 2,6-dimethyl-4-heptanol, n-decanol, isodecanol, n-undecanol, isoundecanol, n-dodecanol, isododecanol, n-tridecanol, isotridecanol, n-tetradecanol, isotetradecanol, n-pentadecanol, isopentadecanol, n-hexadecanol, isohexadecanol, n-heptadecanol, isoheptadecanol, n-octadecanol, isooctadecanol, hexenol, 5-hexenol, 2-heptenol, 6-heptenol, 2-octenol, 8-nonenol, 2-decenol, 2-undecenol, 10-undecenol, 11-dodecenol, 12-tridecenol, 2-tetradecenol, 2-pentadecenol, 2-hexadecenol, 15-hexadecenol, 2-heptadecenol, 2-octadecenol, 9-octadecenol and like aliphatic monohydric alcohols of 6 to 18 carbon atoms, cyclohexanol, methylcyclohexanol, dimethyl-cyclohexanol and like alicyclic monohydric alcohols of 6 to 10 carbon atoms. These alcohols can be used either alone or in combination. Among them, to improve miscibility with a refrigerant, saturated aliphatic monohydric alcohols of 6 to 11 carbon atoms are preferably used and branched-chain saturated aliphatic monohydric alcohols of 6 to 11 carbon atoms are more preferably used.

The amount of "alcohol component 2" to be used in the second-stage esterification reaction can not be particularly limited because it is variable depending on the amount of free carboxylic acid group in the first reaction mixture containing alicyclic or aromatic adjacent dicarboxylic acid monoester of the formula (5). The amount thereof is proper if it is sufficient to quantitatively give the contemplated mixed diester. For example, "alcohol component 2" may be used in an amount of 1 to 1.5 moles per mole of the monoester of the formula (5) in the first reaction mixture. The amount of the monoester in the first reaction mixture can be calculated by measuring the total acid number of the first reaction mixture.

Alternatively, when the first-stage reaction and the second-stage reaction are consecutively carried out without isolating the monoester of the formula (5) obtained in the first-stage, "alcohol component 2" may be used in an amount such that the total amount of "alcohol component 1" and "alcohol component 2" is 2.0 to 2.5 moles, preferably 2.0 to 2.1 moles, per mole of "acid component 1". For example, when the amount of "alcohol component 1" to be used is 0.5 to 1.5 moles, the amount of "alcohol component 2" is 0.5 to 1.0 mole.

In order to avoid decrease in the reaction velocity due to a sudden decrease in the reaction temperature, it is preferable to gradually add alcohol component 2.

The reaction temperature for the second-stage esterification reaction is, e.g., 160 to 230° C. Usually the reaction is completed in 2 to 20 hours.

It is recommended that alcohol component 1 and alcohol component 2 to be used in esterification preferably have a peroxide value of preferably 1.0 meq/kg or less, more preferably 0.5 meg/kg or less. Furthermore, it is recommended that these alcohol components have a carbonyl value of preferably 15 or less, more preferably 5 or less, most preferably 1 or less.

When the ester is prepared using an alcohol having a peroxide value of 1.0 meq/kg or less and a carbonyl value of 5 or less, the obtained ester shows excellent properties as a refrigerator oil. When the ester is prepared using alcohols having a peroxide value of 1.0 meq/kg or less and a carbonyl value of 1 or less, the obtained ester shows markedly superior properties as a refrigerator oil.

The term "peroxide value" used herein is described in 2.5.2-1996 of Standard Methods for the Analysis of Fats, Oil and Related Materials (Japan Oil Chemists' Society), and refers to an amount of iodine released by addition of potassium iodide to a sample and expressed in milliequivalent per kilogram of the sample, according to the method described therein.

The term "carbonyl value" used herein is described in 2.5.4-1996 of Standard Methods for the Analysis of Fats, Oil and Related Materials (Japan Oil Chemists' Society), and refers to a value obtained by causing 2,4-dinitrophenylhydrazine to act on a sample and converting the value of its absorbance at 440 nm to a value per gram of the sample, according to the method described therein.

When an alcohol having a peroxide value of 1.0 meq/kg or less is used, the obtained alicyclic or aromatic dicarboxylic acid mixed diester is less adversely affected in properties such as hue, total acid number and peroxide value and is excellent in the properties such as electrical insulating property, heat stability and hydrolysis stability.

An alcohol having a peroxide value of 1.0 meq/kg or less can be prepared by purifying an alcohol having a peroxide value of more than 1.0 meq/kg through distillation or through a treatment with a reducing agent to thereby decrease the peroxide value.

Generally an alcohol immediately after distillation has a peroxide value of 1.0 meq/kg or less. However, such alcohol may show a peroxide value of more than 1.0 meq/kg due to oxidation during a long-term storage (e.g. storage for 6 months or longer) depending on the storage conditions. Therefore, it is necessary to confirm a peroxide value of the alcohol before esterification.

The purification by distillation can be performed, e.g. by distilling an alcohol having a peroxide value exceeding 1.0 meq/kg at 50-300° C. in the presence of an alkali compound under reduced pressure. Useful alkali compounds include, for example, NaOH, KOH, LiOH, etc. It is recommendable to use the alkali compound in an amount of 0.001 to 0.5 wt. % based on the alcohol.

The purification by reduction can be conducted, e.g. by stirring an alcohol having a peroxide value exceeding 1.0 meq/kg at 30-150° C. in the presence of a reducing agent for 30 minutes to 5 hours, preferably 1 to 2 hours. Useful reducing agents include, for example, sodium borohydride, potassium borohydride, lithium borohydride, lithium aluminum hydride, etc. It is recommendable to use the reducing agent in an amount of 30 to 10,000 ppm based on the alcohol.

When an alicyclic dicarboxylic acid diester is prepared using an alcohol having a carbonyl value of 15 or less, preferably 5 or less, more preferably 1 or less, the obtained ester has excellent hue and reduced peroxide value.

In the case of an alcohol having a carbonyl value of more than 15 as well, its carbonyl value can be decreased to 15 or less by purification through distillation or by purification through reduction, which may be carried out following the procedure of the foregoing method for lowering the peroxide value.

The second-stage esterification reaction may be carried out in the absence of a catalyst or in the presence of a sulfur-free and phosphorus-free catalyst. However, it is recommended to carry out the esterification reaction in the presence of a sulfur-free and phosphorus-free catalyst.

The sulfur-free and phosphorus-free catalyst is a catalyst which does not contain a sulfur element or a phosphorus element in the elements constituting the catalyst. Specifically, examples of the catalyst are Lewis acids and alkali metals, etc. which contain neither a sulfur element nor a phosphorus element. More specifically, examples of Lewis acids are aluminum derivatives, tin derivatives, titanium derivatives, lead derivatives and zinc derivatives. Examples of alkali metals are sodium alkoxide, potassium alkoxide, sodium hydroxide, potassium hydroxide, etc. These catalysts can be used either alone or in combination. Preferred catalysts are those which do not contain a sulfur element and a phosphorus element as the impurities.

Among such catalysts, it is particularly preferable to use tetra($C_3$-$C_8$ alkyl) titanate, titanium oxide, titanium hydroxide, sodium alkoxide of 1 to 4 carbon atoms, sodium hydroxide, $C_3$-$C_{12}$ fatty acid tin salt, tin oxide, tin hydroxide, zinc oxide, zinc hydroxide, lead oxide, lead hydroxide, aluminum oxide and aluminum hydroxide. The amount of the catalyst to be used is, for example, about 0.05 to about 1 wt. % based on the total amount of the first reaction mixture and alcohol component 2.

To accelerate the distillation of water generated by the reaction in esterification, a water-entraining agent such as benzene, toluene, xylene, cyclohexane or the like may be used in esterification.

The esterification reaction may be carried out under atmospheric pressure or under reduced pressure (e.g., 133 to 66500 Pa). However, from a viewpoint of accelerating the esterification reaction, it is preferable to combine esterification reaction under atmospheric pressure and esterification reaction under reduced pressure. Particularly, it is recommended to carry out the esterification reaction under reduced pressure in a later stage of the reaction (such as the stage in which the total acid number of the reaction mixture becomes about 10 mgKOH/g or less) when the esterification reaction velocity becomes low.

When an oxide, peroxide, carbonyl compound and like oxygen-containing organic compounds are produced due to oxidative deterioration of the raw materials, the obtained ester and the organic solvent (water-entraining agent) in the esterification reaction, the hygroscopicity, hydrolysis stability and electrical insulating property would be adversely affected. Consequently, the esterification reaction is preferably carried out in an atmosphere or stream of inert gas such as nitrogen gas.

In the preparation of the alicyclic or aromatic dicarboxylic acid mixed diester represented by the formula (4) of the present invention, when the proportion of an monohydric alcohol of 1 to 5 carbon atoms [(P)+(S)] is 10 to 90 mole %, relative to the total amount [(P)+(Q)+(S)+(T)] of alcohol component 1 [(P)+(Q)] used in the first-stage esterification reaction and alcohol component 2 [(S)+(T)] used in the second-stage esterification reaction, it is recommended, from the standpoint of reducing the reaction time, 1) to use the whole amount of the monohydric alcohol of 1 to 5 carbon atoms as (P) in the first-stage esterification reaction and to use 0 mole % of said alcohol in the second-stage esterification reaction, when said proportion of the monohydric alcohol of 1 to 5 carbon atoms [(P)+(S)] is not less than 10 mole % and not greater than 50 mole %, and 2) to use the monohydric alcohol of 1 to 5 carbon atoms as (P) in an amount of 50 mole % relative to the total alcohol amount [(P)+(Q)+(S)+(T)] in the first-stage esterification reaction and to use the rest of said monohydric alcohol of 1 to 5 carbon atoms as (S) in the second-stage esterification reaction, when said proportion of the monohydric alcohol of 1 to 5 carbon atoms [(P)+(S)] is more than 50 mole % and not more than 90 mole %.

When the alicyclic or aromatic adjacent dicarboxylic acid mixed diester represented by the formula (4) is prepared by the process of the present invention, two species of esters represented by the formula (6) are concurrently produced as by-products, but no problem arises even if the reaction product contains such ester compounds.

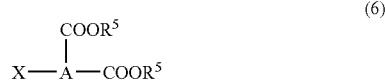

(6)

wherein X, A and $R^5$ are as defined above, two $R^5$ are the same, and the two —$COOR^5$ groups are attached to two adjacent carbon atoms of a cyclohexane ring, a cyclohexene ring or a benzene ring;

When using, e.g. a monohydric alcohol of 1 to 5 carbon atoms ($R^{5a}OH$) as alcohol component 1 and a monohydric alcohol of 6 to 18 carbon atoms ($R^{6a}OH$) as alcohol component 2, or when using a single alcohol or an alcohol mixture comprising a monohydric alcohol of 1 to 5 carbon atoms ($R^{5a}OH$) (P) and a monohydric alcohols of 6 to 18 carbon atoms ($R^{6a}OH$) (Q) (wherein (P): (O) is 0.1:99.9 to 100:0 (molar ratio)) as alcohol component 1 and a single alcohol or an alcohol mixture in which the constituent alcohols are the same as those of alcohol component 1 and which comprises a monohydric alcohol of 1 to 5 carbon atoms ($R^{5a}OH$) (S) and a monohydric alcohols of 6 to 18 carbon atoms ($R^{6a}OH$) (T) (wherein (S):(T) is 0:100 to 99.9:0.1 (molar ratio)) as alcohol component 2, esters represented by the formulas (7) and (8) given below are produced as by-products, in addition to the mixed diester represented by the formula (4a) according to the present invention, but the diesters represented by the formulas (7) and (8) can be used as a refrigerator oil as admixed with the mixed diester of the formula (4a) according to the invention:

1) the alicyclic or aromatic adjacent dicarboxylic acid mixed di(lower alkyl)ester of the formula (7)

(7)

wherein A and X are as defined above, and two R s are the same and $R^{5a}$ is a group resulting from elimination of hydroxyl group from the monohydric alcohol of 1 to 5 carbon atoms, i.e. a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and the two —$COOR^{5a}$ groups are attached to two adjacent carbon atoms of a cyclohexane ring, a cyclohexene ring or a benzene ring;

2) an alicyclic or aromatic adjacent dicarboxylic acid mixed diester of the formula (4a)

(4a)

wherein A and X are as defined above, $R^{5a}$ and $R^{6a}$ are different from each other, and $R^{5a}$ is as defined above, and $R^{6a}$ is a group resulting from elimination of hydroxyl group from the monohydric alcohol of 6 to 18 carbon atoms, i.e. a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and the group —$COOR^{5a}$ and the —$COOR^{6a}$ group are attached to two adjacent carbon atoms of a cyclohexane ring, a cyclohexene ring or a benzene ring represented by A; and 3) an alicyclic or aromatic adjacent dicarboxylic acid mixed di(higher alkyl)ester of the formula (8)

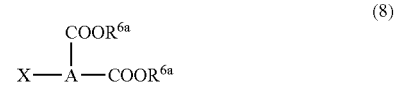

(8)

wherein A and X are as defined above and two $R^{6a}$s are the same and $R^{6a}$ is a group resulting from elimination of a hydroxyl group from the monohydric alcohol of 6 to 18 carbon atoms, i.e. a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms; and the two —$COOR^{6a}$ groups are attached to two adjacent carbon atoms of a cyclohexane ring, a cyclohexene ring or a benzene ring represented by A.

After completion of the esterification reaction, the excess starting materials are distilled off under reduced pressure or under atmospheric pressure. When the process is intended to prepare only the alicyclic or aromatic adjacent dicarboxylic acid mixed diester of the formula (4) (e.g. the ester of the formula (4a)), the ester mixture (e.g. an ester mixture of an ester of the formula (7), an ester of the formula (4a) and an ester of the formula (8)) prepared by the foregoing process may be purified by distillation to remove the ester of the formula (6) (e.g. the esters of the formulas (7) and (8)). In this case, it is preferable to purify the ester mixture by the method to be described below and then separate the ester of the formula (4a) by a known method such as distillation.

In a preferred aspect of the invention, however, it has been found that an ester mixture of 1) an ester of the formula (7), 2) a mixed diester of the formula (4a) and 3) an ester of the formula (8) is useful as a refrigerator oil.

Thus, the present invention also provides a lubricating oil for a refrigerator (refrigerator oil) comprising a mixture of:

1) an ester of the formula (7), 2) a mixed diester of the formula (4a) and 3) an ester of the formula (8).

A wider range of the proportions of esters 1), 2) and 3) in the above mixture is made available by changing the ratio of alcohol component 1 and alcohol component 2 to be used or can vary by changing the reaction temperature and reaction time in step (b). Generally, it is preferable that mixed diester 2) is present in a proportion of 100, ester 1) is present in a proportion of about 5 to 300, particularly 7 to 100 and ester 3) is present in a proportion of 7 to 500, preferably 10 to 350. Herein, the proportions are expressed by area ratio as determined on a gas chromatogram of a mixture of esters 1), 2) and 3). The conditions under which gas chromatography is conducted will be described in Examples.

Purification of Ester of the Invention

In embodiment I and in embodiment II as well, after the esterification reaction, the step of evaporating the excess starting materials (especially alcohols) from a reaction mixture under reduced pressure (at 133 to 66500 Pa) or under atmospheric pressure at 100 to 230° C., and the neutralization and water-washing step of the obtained crude ester are carried out.

The order of carrying out the excess starting material evaporation step and the neutralization and water-washing step is not particularly limited, but it is preferable to conduct the excess starting material evaporation step first, followed by the neutralization and water-washing step.

Neutralization can be carried out by various methods. For example, neutralization step is preferably carried out as follows: First, a 0.1 to 10 wt. % aqueous solution of alkali (an alkali metal hydroxide such as sodium hydroxide and potassium hydroxide, an alkali metal carbonate such as sodium carbonate and potassium carbonate) is added to an esterification reaction product obtained by evaporation of excess alcohol(s) after the esterification reaction or acid component and alcohol component used as the starting materials in the esterification reaction. The amount of the aqueous solution of alkali is preferably 2 to 20 parts by weight, per 100 parts by weight of said esterification reaction product or per 100 parts by weight of a total weight of the acid component and alcohol. Then, the resulting mixture is stirred at room temperature to 90° C. for 10 minutes to 5 hours, preferably 30 minutes to 2 hours. By this neutralization, unreacted carboxylic acid(s) can be removed and the catalyst used in the reaction and organometallic compounds derived from the catalyst are decomposed.

The step of washing the crude product with water after the neutralization is carried out until the washings (=water used for this washing step) are neutral, and the method of washing is not particularly limited. For example, the water-washing step can be carried out at room temperature to 90° C. by using water in a total amount of 10 to 1000 parts by weight per 100 parts by weight of said crude product until the washings are neutral.

Whether the neutralization is complete or not can be confirmed by measuring the total acid number of the esterification reaction product (crude ester) after being washed with water. For example, the neutralization may be carried out until the total acid number of the esterification reaction product (crude ester) becomes 0.05 mgKOH/g or less, preferably about 0.02 mgKOH/g. When the esterification reaction product (crude ester) has a total acid number of higher than 0.05 mgKOH/g, it is preferable to carry out the neutralization and washing with water again until the total acid number of the esterification reaction product (crude ester) becomes 0.05 mgKOH/g or less.

Then, purification step is carried out using liquid-liquid extraction or distillation under reduced pressure or purification by adsorbents or the like to purify the ester. In the purification step, it is recommended to use a procedure which do not allow incorporation of a sulfur element and/or phosphorus element into the ester.

The obtained ester contains various impurities depending on the producing process. Examples of such impurities are acidic compounds, metal compounds, hetero atom-containing compounds, oxygen-containing organic compounds and the like. The acidic compounds include inorganic and organic acid components. The metal compounds include metals in general derived from the raw materials and the catalyst. The hetero atom-containing compounds include sulfur-containing compounds, phosphorus-containing compounds, etc. The oxygen-containing organic compounds include peroxides, carbonyl compounds and the like which would particularly affect the ester. These impurities may deteriorate the hydrolysis stability, electrical insulating property and heat stability and may lead to corrosion of metal parts and to generation of sludge. For this reason, it is desirable to sufficiently remove the impurities from the ester in the purification step.

Among the foregoing procedures for the purification step, distillation under reduced pressure, purification using adsorbents are particularly preferable, and the purification using adsorbents is more preferable.

Liquid-liquid extraction can be carried out by a conventional liquid-liquid extraction method using one or more organic solvents such as hexane, toluene, xylene, methanol and the like.

Distillation under reduced pressure can be carried out at a temperature of 100 to 300° C. at a reduced pressure of 13 to 13300 Pa.

The purification using adsorbents which is a more preferable procedure will be described below in detail.

Useful adsorbents include, for example, natural or synthetic adsorbents, specifically activated carbon, activated alumina, silica gel, silica-alumina, activated clay, zeolite, magnesia, calcia, diatomaceous earth, hydrotalcite, as well as synthetic adsorbents such as ion exchange resins of the non-sulfonic acid type, synthetic hydrotalcite and the like. The amount of the adsorbent(s) to be used may very depending on the kind thereof, but, it is recommendable to use the adsorbent(s) in an amount of 0.01 to 5 wt. %, preferably 0.05 to 5 wt. %, relative to the theoretical yield of the alicyclic or aromatic dicarboxylic acid diester of the formula (E) of the present invention.

In the purification with an adsorbent, it is advantageous to use, for example, 1 to 4 kinds of adsorbents, particularly 2 to 4 kinds of adsorbents in combination.

The shape of the adsorbent to be used in the present invention is not limited, and examples thereof are powders, molded products among which powders are preferred.

It is recommended that the particle size of the powdery adsorbents is, for example, 0.01 to 1000 μm, preferably 0.1 to 500 μm.

When at least 2 kinds of adsorbents are used, adsorption treatment may be performed using one adsorbent for one of operations (stepwise), or using said at least 2 kinds of adsorbents in admixture for a single adsorption procedure. It is recommended to use at least 2 kinds of adsorbents in admixture for a single adsorption procedure.

The combined use of at least 2 adsorbents different in adsorption mechanisms is more effective. For example, activated carbon effects physical adsorption of polar substances, and activated alumina brings about physical adsorption of acidic substances. Silica gel causes adsorption due to hydrogen bond between a polar substance and a silanol group existing on the surface of silica gel.

Examples of preferred combinations of adsorbents are as follows:

activated carbon+activated alumina,
activated carbon+silica gel,
activated carbon+magnesia,
activated carbon+activated clay,
activated carbon+silica-alumina,
activated alumina+activated clay,
activated carbon+zeolite,
activated carbon+hydrotalcite,
activated clay+zeolite.

To improve adsorption performance, the combined use of at least 3 adsorbents is also effective. Examples of such combinations are as follows.

Activated carbon+activated alumina+silica gel,
Activated carbon+silica gel+magnesia,
Activated carbon+activated clay+activated alumina,
Activated carbon+hydrotalcite+zeolite,
Activated carbon+activated clay+hydrotalcite.

When two adsorbents are used conjointly, the proportions of said two adsorbents are not particularly limited and are variable depending on the kind of adsorbents. Usually, it is recommended that they are used in a weight ratio of, for example, 1/100 to 100/1, preferably 1/9 to 9/1, more preferably 3/7 to 7/3.

When three or more adsorbents are used, the proportions of these adsorbents are as follows. For example, when 3 adsorbents are used, it is recommended to use the foregoing two adsorbents and a third adsorbent wherein the weight ratio of said two adsorbents/the third adsorbent is, for example, 1/100 to 100/1, preferably 1/9 to 9/1, more preferably 3/7 to 7/3.

When 4 adsorbents are used, it is recommended to use the foregoing three adsorbents and a fourth adsorbent wherein the weight ratio of said three adsorbents/the fourth adsorbent is, for example, 1/100 to 100/1, preferably 1/9 to 9/1, more preferably 3/7 to 7/3.

The adsorbents to be used in the invention may be dehydrated before use to enhance the adsorbing ability. For example, dehydration before use is conducted at 60° C. to 150° C. for 30 minutes to 10 hours under atmospheric pressure or under reduced pressure, preferably a reduced pressure of 133 to 66500 Pa (1-500 mmHg).

The purification method by adsorption is exemplified below.

1) 0.01 to 5 parts by weight, preferably 0.05 to 5 parts by weight of two or more adsorbents are added to 100 parts by weight of the dicarboxylic acid diester prepared by the foregoing process of embodiment I or embodiment II and subjected to the neutralization and water-washing steps. The mixture is stirred with heating at 70 to 120° C., preferably 80° C. to 110° C. for 10 minutes to 2 hours, preferably 30 minutes to 1 hour, under atmospheric pressure or reduced pressure (e.g. 133 to 66500 Pa (1-500 mmHg)). In this procedure, an adsorption column charged with adsorbents may be used, and the adsorption treatment is carried out by passing the ester through the column.

2) The ester prepared by the foregoing process is treated according to the above-mentioned method 1) using one adsorbent, followed by further adsorption treatment with another adsorbent. Optionally two or more adsorption columns may be set in series and individually charged with an adsorbent, and the alicyclic dicarboxylic acid diester is passed through the columns one by one for adsorption treatment.

Herein, it is recommended that an aqueous solution of an alkali, water, organic solvents, adsorbents and the like to be used in the water-washing step, neutralization step and purification step should be completely or substantially free of a sulfur element and/or a phosphorus element.

It is recommended that the alicyclic dicarboxylic acid diester represented by the formula (1) and the alicyclic or aromatic adjacent dicarboxylic acid mixed diester represented by the formula (4), as well as refrigerator lubricating oil comprising one or more of these esters have a water content of 100 ppm or less, preferably 50 ppm or less. Therefore, it is preferable to remove water by sufficiently carrying out dehydration treatment. The dehydration may be carried out, for example, under atmospheric or reduced pressure, preferably under a reduced pressure of 133 Pa to 66500 Pa, at a temperature ranging from room temperature to 150° C., preferably 50 to 140° C., for 0.1 hour to 10 hours. If the water content exceeds 100 ppm, hydrolysis might possibly take place, thereby affecting electrical insulation properties, heat stability and hydrolysis stability.

When the foregoing purification step and the dehydration step are carried out, the order thereof is not particularly limited. However, there is a possibility that the ester may absorb water during the purification step, and therefore it is preferable to carry out dehydration step after the purification step.

A preferred method for preparing the alicyclic or aromatic dicarboxylic acid diester represented by the formula (E) according to the present invention recommendably comprises the steps of (i) carrying out the esterification reactions by the method of embodiment I or II to obtain an ester mixture, (ii) removing excess starting materials (especially alcohol(s)) from the ester obtained in step (i), (iii) neutralizing the crude ester obtained in step (ii) and washing the neutralized crude ester with water, (iv) purifying the crude ester neutralized and washed with water in step (iii) by treatment with 1 to 4 kinds of adsorbents, (v) dehydrating the purified ester obtained in step (iv).

The alicyclic or aromatic dicarboxylic acid diesters represented by the formula (E), particularly, the alicyclic or aromatic dicarboxylic acid diesters represented by formula (4) or the ester mixture (such as a ester mixture of the ester represented by the formula (7), the ester represented by the formula (4a) and the ester represented by the formula (8)) prepared by the process of embodiment I or embodiment II and purified by the above purification method comprising the steps (i) to (v) above have the following properties and is suitable as a refrigerator oil:

1) a total acid number of 0.05 mgKOH/g or less, preferably 0.02 mgKOH/g or less. The term "total acid number" used herein refers to a value prescribed in JIS-K-2501, and more specifically means the number of milligrams of potassium hydroxide required to neutralize the total acid components contained in 1 g of the sample. The higher the number is, the more the amount of the acid components in the sample is, 2) a sulfated ash content of 10 ppm or less, preferably 5 ppm or less (as measured according to JIS-K-2272.5), 3) a sulfur content of 20 ppm or less, preferably 10 ppm or less. The sulfur content is measured by diluting 5.0 g of a sample ester with hexane to give a 10.0 ml dilution and the sulfur content of the ester is measured with a sulfur analyzer TS-03 (product of Mitsubishi Chemical Corp.)), 4) a phosphorus content of 20 ppm or less, preferably 10 ppm or less (as measured according to JIS-K-0102-1998), 5) a hydroxyl value of 3 mgKOH/g or less, preferably 2 mgKOH/g or less (as measured according to JIS-K-0070), 6) a peroxide value of 1.0 meq/kg or less, preferably 0.5 meq/kg or less (as measured according to 2.5.2-1996 of Standard Methods for the Analysis of Fats, Oil and Related Materials (Japan Oil Chemists' Society)), 7) a carbonyl value of 10 or less, preferably 5 or less (as measured according to 2.5.4-1996 of Standard Methods for the Analysis of Fats, Oil and Related Materials (Japan Oil Chemists' Society)), 8) a volume resistivity of $1\times10^{11}$ Ω·cm or more, preferably $1\times10^{12}$ Ω·cm or more (as measured at 25° C. according to JIS-C-2101), and
9) a water content of 100 ppm or less, preferably 50 ppm or less (as measured according to JIS-K-2275 using Karl Fischer's moisture meter).

The ester represented by the formula (1) according to embodiment I additionally has:
10) a hue of 50 or less, preferably 30 or less (Hasen color number as measured according to JIS-K-0071-1-1998).

When the alicyclic dicarboxylic acid diester has the above-mentioned properties outside of said respective ranges, the ester is inferior in electrical insulating property, heat stability and hydrolysis stability.

Specifically,
1) When the total acid number exceeds 0.05 mgKOH/g, the ester tends to be inferior in hydrolysis stability and becomes more corrosive to metals,
2) When sulfated ash content exceeds 10 ppm, the ester tends to be inferior in heat stability, electrical insulating property.
3) When sulfur content exceeds 20 ppm, the ester tends to be inferior in heat stability, hydrolysis stability and electrical insulating property.
4) When phosphorus content exceeds 20 ppm, the ester tends to be inferior in heat stability, hydrolysis stability and electrical insulating property.
5) When hydroxyl value exceeds 3 mgKOH/g, the ester is more hygroscopic and tends to be inferior in hydrolysis stability and electrical insulating property.
6) When peroxide value exceeds 1.0 meq/kg, the ester tends to be inferior in heat stability and electrical insulating property.
7) When carbonyl value exceeds 10, the ester tends to be inferior in heat stability and electrical insulating property.
8) When volume resistivity is less than $1\times10^{11}$ Ω·cm, the ester tends to be inferior in electrical insulating property.
9) When water content exceeds 100 ppm, the ester tends to be inferior in electrical insulating property, heat stability and hydrolysis stability.

Lubricating Oil for a Refrigerator

The lubricating oil for a refrigerator (refrigerator oil) according to the present invention contains either the alicyclic dicarboxylic acid diester of the formula (1) prepared by the process of embodiment I or the alicyclic or aromatic dicarboxylic acid mixed diester of the formula (4) prepared by the process of embodiment II.

In other words, the ester or a mixture of the esters according to embodiment I and II of the invention can be used as a refrigerator oil.

The amount of the alicyclic dicarboxylic acid diester of the formula (1) according to embodiment I in a refrigerator oil is not limited but is preferably 10 wt. % or more, more preferably 20 wt. % or more, based on the total amount of refrigerator oil.

The amount of the alicyclic or aromatic adjacent dicarboxylic acid mixed diester of the formula (4) in a refrigerator oil is not limited, but is preferably 10 wt. % or more, more preferably 20 wt. % or more, based on the total amount of refrigerator oil.

Particularly, the refrigerator oil of the invention preferably contains
1) an alicyclic or aromatic adjacent dicarboxylic acid mixed diester of the formula (4) and
2) an alicyclic or aromatic adjacent dicarboxylic acid diester of the formula (6).

The mixing ratio of the alicyclic or aromatic adjacent dicarboxylic acid mixed diester (A) of the formula (4) and the alicyclic or aromatic adjacent dicarboxylic acid diester (B) of the formula (6) is recommendably 10 to 800 parts by weight, preferably 17 to 450 parts by weight, of (B), per 100 parts by weight of (A).

Particularly, the present invention also provides a refrigerator lubricating oil (refrigerator oil) comprising an ester mixture of:
1) the ester of the formula (7),
2) the mixed diester of the formula (4a) and
3) the ester of the formula (8).

A wider range of the proportions of esters 1), 2) and 3) in the above mixture is made available by changing the ratio of alcohol component 1 and alcohol component 2 or can vary by changing the reaction temperature and reaction time in step (b). Generally, it is preferable that mixed diester 2) is present in a proportion of 100, ester 1) is present in a proportion of about 5 to 300, particularly about 7 to 100 and ester 3) is present in a proportion of about 7 to 500, preferably about 10 to 350. Herein, the proportions are expressed by area ratio as determined on a gas chromatogram of a mixture of esters 1), 2) and 3). The conditions under which gas chromatography is conducted will be described in Examples.

The refrigerator oil according to the invention may further contain one or more compounds selected from other lubricating oil base stock (hereinafter referred to as "concomitant base stock") within the range which does not affect the effects of the invention.

Examples of the concomitant base stock are one or more compounds selected from the group consisting of mineral oil (hydrocarbon oil obtained by petroleum refining), poly-α-olefins, polybutenes, alkylbenzenes, alkylnaphthalenes and like synthetic hydrocarbons, isomerized oil of synthetic hydrocarbon prepared by the Fischer-Tropsch process, organic acid esters, polyalkylene glycols, polyvinyl ethers, polyphenyl ethers, alkylphenyl ethers and silicone oils.

Examples of the mineral oil include solvent-refined mineral oils, hydrogenated refined mineral oils, wax-isomerized oils, etc. Usually it is recommended to use mineral oils having a kinematic viscosity of 1.0 to 40 mm²/s, preferably 2.0 to 30 mm²/s, at 100° C.

Examples of the poly-α-olefin include polymers or copolymers of alpha-olefin(s) of 2 to 16 carbon atoms (such as ethylene, propylene, 1-butene, 1-hexene, 1-octene, 1-decene, 1-dodecene, 1-tetradecene, 1-hexadecene, etc.) having a kinematic viscosity of 1.0 to 40 mm²/s at 100° C. and a viscosity index of 100 or more, among which recommendable are those having a kinematic viscosity of 2.0 to 30 mm²/s at 100° C. and a viscosity index of 120 or more.

Examples of the polybutene include polymers prepared by polymerization of isobutylene or by copolymerization of isobutylene and normal butylene and having a kinematic viscosity in a wide range of 2.0 to 6000 mm²/s at 100° C.

Examples of the alkylbenzene include monoalkyl-benzenes, dialkylbenzenes, trialkylbenzenes, tetraalkylbenzenes, etc. in which the alkyl substituent(s) is(are) a straight-chain or branched-chain alkyl group having 1 to 40 carbon atoms, and which have a molecular weight of 200 to 450.

Examples of the alkylnaphthalene include monoalkylnaphthalene, dialkylnaphthalene, etc. in which the alkyl substituent(s) is(are) a straight-chain or branched-chain alkyl group having 1 to 30 carbon atoms.

Examples of the organic acid ester other than the present ester include aliphatic dibasic acid esters, aromatic polycarboxylic acid esters (other than phthalic acid mixed diesters), polyol esters and other esters.

Examples of the aliphatic dibasic acid esters include aliphatic dibasic acid diesters prepared from an aliphatic dicarboxylic acid of 6 to 12 carbon atoms such as adipic acid, azelaic acid, sebacic acid, dodecane-diacid or the like with a straight-chain or branched-chain saturated or unsaturated aliphatic alcohol of 3 to 22 carbon atoms.

Examples of the aromatic polycarboxylic acid esters are esters of an aromatic polycarboxylic acid such as isophthalic acid, terephthalic acid, trimellitic acid, pyromellitic acid or the like or anhydride thereof with a straight-chain or branched-chain saturated or unsaturated aliphatic alcohol of 3 to 22 carbon atoms.

Examples of the polyol esters include esters of a polyol such as neopentyl glycol, trimethylolpropane, pentaerythritol, ditrimethylolpropane, dipentaerythritol or the like with a straight-chain and/or branched-chain saturated fatty acid of 3 to 22 carbon atoms.

Examples of other esters are carboxylic acid esters such as esters of dimer acid or a hydrogenation product thereof (saturated acid) with a straight-chain or branched-chain saturated or unsaturated aliphatic alcohol of 3 to 22 carbon atoms, aliphatic branched-chain carboxylic acid monoalkyl ester, aliphatic straight-chain carboxylic acid monoalkyl ester, etc.

Useful polyalkylene glycols include, for example, those prepared by ring opening polymerization of a straight-chain or branched-chain alkylene oxide of 2 to 4 carbon atoms with an alcohol. Examples of the alkylene oxide are ethylene oxide, propylene oxide, butylene oxide and the like. Polymers prepared from one of them, and copolymers prepared from a mixture of at least two of them can be used. Further it is possible to use compounds having a hydroxyl moiety etherified or esterified in one or both ends of the molecule. Useful polyalkylene glycols are recommendably those having a kinematic viscosity of preferably 5.0 to 1000 mm$^2$/s (40° C.), more preferably 5.0 to 500 mm$^2$/s (40° C.).

Examples of the polyvinyl ethers include compounds prepared by polymerization of vinyl ether monomer, and examples of the monomer are methyl vinyl ether, ethyl vinyl ether, isopropyl vinyl ether, n-butyl vinyl ether, isobutyl vinyl ether, sec-butyl vinyl ether, tert-butyl vinyl ether, n-pentyl vinyl ether, n-hexyl vinyl ether, 2-methoxyethyl vinyl ether, 2-ethoxyethyl vinyl ether and the like. Useful polyvinyl ethers are recommendably those having a kinematic viscosity of preferably 5.0 to 1000 mm$^2$/s (40° C.), more preferably 5.0 to 800 mm$^2$/s (40° C.).

Examples of the polyphenyl ether include compounds having a structure wherein at least 2 meta-positions on the aromatic ring are bonded by ether linkage or thioether linkage. More specific examples thereof are bis(m-phenoxyphenyl)ether, m-bis(m-phenoxyphenoxy)benzene and the like.

Useful alkyl phenyl ethers include, for example, compounds having a straight-chain or branched-chain alkyl group of 6 to 18 carbon atoms as substituent(s), and particularly preferred examples thereof include alkyldiphenyl ether having one or two alkyl groups as substituent(s).

Examples of silicone oils include dimethyl silicone, methylphenyl silicone, long chain alkyl silicone, fluorosilicone and like modified silicones.

When the concomitant base stock is used, the amount of the concomitant base stock in the refrigerator oil of the invention is 10 to 90 wt. %, recommendably 10 to 50 wt. %.

When the alicyclic dicarboxylic acid diester according to embodiment I or the alicyclic or aromatic adjacent dicarboxylic acid mixed diester according to embodiment II of the present invention is used in a refrigerator oil, one or more additives such as antioxidants, metal deactivator, defoaming agents, hydrolysis depressants and the like may optionally be added to improve the performance of esters. There is no limitation on such additives insofar as they can achieve the desired effects. Specific examples of such additives are described below.

Examples of useful antioxidants are 2,6-di-tert-butyl-p-cresol, 4,4'-methylenebis-2,6-di-tert-butylphenol and like phenols, N-phenyl-α-naphthylamine, p,p'-dioctyldiphenylamine and like amines. The antioxidant, if used, may be added usually in an amount of 0.01 to 5 wt. %, preferably 0.1 to 2 wt. %, based on the refrigerator oil.

Examples of metal deactivator are benzotriazole compounds and like compounds. The metal deactivator, if used, may be added in an amount of 0.01 to 0.4 wt. % based on the refrigerator oil.

A liquid silicone is suitable for use as a defoaming gent. The defoaming agent, if used, may be added in an amount of 0.0005 wt. % to 0.01 wt. % based on the refrigerator oil.

Examples of useful hydrolysis depressants are epoxy compounds such as alkyl glycidyl ethers, phenyl glycidyl ethers, alkyleneglycol glycidyl ethers, glycidyl esters, alicyclic epoxy compounds, epoxidized alkene and derivatives thereof. The hydrolysis depressant, if used, may be added in an amount of 0.05 wt. % to 2 wt. % based on the refrigerator oil.

Processes for preparing the refrigerator oil of the invention include, for example, a process comprising the steps of adding the alicyclic dicarboxylic acid diester of the formula (1) according to embodiment I or the alicyclic or aromatic adjacent dicarboxylic acid mixed diester of the formula (4) or the ester mixture containing the mixed diester (such as the ester mixture of the ester of the formula (7), the ester of the formula (4a) and the ester of the formula (8)) according to embodiment II and if desired said one or more concomitant base stocks and/or said one or more additives, and uniformly dissolving them. There is no limitation on the order of adding the concomitant base stock and additives. Dehydration may be conducted after uniform dissolution for control of water.

Depending on the kind of refrigerator to be used, the alicyclic dicarboxylic acid diester of the formula (1) according to embodiment I alone or the alicyclic or aromatic adjacent dicarboxylic acid mixed diester or an ester mixture containing the mixed diester according to embodiment II may be used as a refrigerator oil.

The refrigerator oil of the present invention can be used as a lubricating oil for a variety of refrigerators in which hydrofluorocarbon is used as a refrigerant. Examples of such hydrofluorocarbons are HFC-134a, HFC-134, HFC-125, HFC-32, HFC-143a, and mixed refrigerants thereof such as R404A, R407A, R407C, R407E, R410A, R507A, etc.

The following effects can be achieved by using, as a refrigerator oil, the alicyclic dicarboxylic acid diester of the formula (1) prepared according to embodiment I of the present invention.

1) The alicyclic dicarboxylic acid diester prepared using an aliphatic monohydric alcohol having a peroxide value adjusted to not more than 1.0 meq/kg is advantageous in respect of hue, peroxide value, etc. and excellent in electrical insulating property, heat stability, long-term hydrolysis stability, etc.

2) The alicyclic dicarboxylic acid diester prepared using an aliphatic monohydric alcohol having a peroxide value of not more than 1.0 meq/kg and having a carbonyl value of 15 or less can exhibit more improved properties in respect of hue, peroxide value, heat stability and long-term hydrolysis stability.

3) The alicyclic dicarboxylic acid diester prepared by esterification reaction in the absence of a catalyst or in the presence of a sulfur-free and phosphorus-free catalyst has a volume resistivity of $1.0 \times 10^{11}$ Ω·cm or more and involves only a small degree of increase in acid number by heating, and thus shows a high heat stability and also outstanding long-term hydrolysis stability.

The mixed diester prepared by the 2-step esterification process according to embodiment II of the invention, when used as a refrigerator oil, produces the following effects.

1) Said mixed diester can be prepared under milder conditions than the mixed diester prepared by the 1-step esterification process, and is of high quality. This ester, when used as a refrigerator oil, displays a high hydrolysis stability, a high heat stability and an excellent electrical insulating property. For example, the alicyclic adjacent dicarboxylic acid mixed diester prepared by the 1-step esterification process or the ester prepared by the 2-step esterification process in the presence of a sulfur-containing catalyst is insufficient in hydrolysis stability and heat stability, whereas the ester prepared by the 2-step esterification process according to the present invention is much improved in hydrolysis stability, heat stability and electrical insulating property.

2) By suitably changing the kinds and/or mixing ratio of alcohols in alcohol component 1 and alcohol component 2 used for esterification, the desired mixed diester can be prepared which can satisfy the need for various viscosity characteristics.

3) In preparing the mixed diester according to the 2-step esterification reaction, the use of aliphatic monohydric alcohol(s) having a peroxide value of 1.0 meq/kg or less and further having a carbonyl value of 15 or less gives the desired mixed diester which is still more advantageous with respect to peroxide value, heat stability and hydrolysis stability.

It is known that a refrigeration system is exposed to a pronouncedly high temperature due to friction during the operation of a compressor in a refrigerator. In view of this condition, it is important for the refrigerator oil to have a high heat stability and to exhibit a high stability during exposure to a high temperature. The electrical insulating property is also important to prevent an accident due to leakage during the operation of a refrigerator. After the ester is exposed to a high temperature, the smaller the increase of total acid number is, the higher the heat stability is. The higher the volume resistivity of the ester is, the higher the electrical insulating property is.

Examples of refrigerators for which the refrigerator oil of the invention can be used are compressors in automotive air conditioners, refrigerators, automatic vending machines, refrigeration-type display cases, room air conditioners or large-size refrigerators for industrial use or the like in which hydrofluorocarbon is used as a refrigerant.

EXAMPLES

Embodiment I of the present invention will be described in greater detail with reference to the following examples and comparative examples. The properties of lubricating oils prepared in these examples and the like were evaluated by the following methods.

Kinematic Viscosity
Measured according to JIS-K-2283 using Ubbellohde viscometer.

Total Acid Number
Measured according to JIS-K-2501.

Hue
Hazen color number was measured according to JIS-K-0071-1-1998.

Sulfated Ash Content
Measured according to JIS-K-2272.5

Sulfur Content
A sample ester (5.0 g) was diluted with hexane to give a 10.0 ml dilution, and the sulfur content of the ester was measured with a sulfur analyzer, TS-03 (product of Mitsubishi Chemical Corp.)

Phosphorus Content
Measured according to JIS-K-0102-1998.

Hydroxyl Value
Measured according to JIS-K-0070.

Peroxide Value
Measured according to 2.5.2-1996 of Standard Methods for the Analysis of Fats, Oil and Related Materials (Japan Oil Chemists' Society)

Carbonyl Value
Measured according to 2.5.4-1996 of Standard Methods for the Analysis of Fats, Oil and Related Materials (Japan Oil Chemists' Society)

Test for Electrical Insulating Property
The volume resistivity was measured at 25° C. according to JIS-C-2101. The higher the volume resistivity is, the more excellent the electrical insulating property is.

Test for Heat Stability
Iron wire, copper wire and aluminum wire, 1.6 mm in diameter and 40 mm in length, were placed in a beaker of 53 mm in inner diameter and 56 mm in height. 40 g of an ester sample was weighed out and introduced into the beaker. The beaker was placed in an oven and was heated at 175° C. for 15 hours. Then the ester sample was taken out to measure the total acid number. The smaller the increase in total acid number after the test as compared with that before the test is, the higher the heat stability is. The result obtained in this test is an index of resistance of the ester to oxidative deterioration.

Test for Hydrolysis Stability
Iron wire, copper wire and aluminum wire of 1.6 mm in diameter and 40 mm in length were placed in a glass test tube of 6.6 mm in inner diameter and 30 cm in height. Then, 2.0 g of an ester sample and 0.2 g of distilled water were weighed out and introduced into the test tube. The test tube was sealed while it was degassed by an aspirator. The test tube was placed into an oven and was heated at 175° C. for 80 hours. Then the ester sample was taken out to measure the total acid number. It is considered that the smaller the increase in total acid number is, the higher the hydrolysis stability is. The result obtained in this test is an index of hydrolysis resistance of the ester as heated in the presence of water.

Water Content

Measured according to JIS-K-2275 using Karl Fischer's moisture meter (MKC-510, product of Kyoto Denshi Kabushiki Kaisha)

Example I-1

A 4-necked flask equipped with a stirrer, a thermometer and a Dean-Stark water separator was charged with 152.1 g (1 mole) of 4-cyclohexene-1,2-dicarboxylic anhydride (prepared by usual Diels-Alder reaction of maleic anhydride with 1,3-butadiene), 162.8 g (2.2 moles) of isobutanol having a peroxide value of 0.2 meq/kg and a carbonyl value of 0.3 and xylene (5 wt. % relative to the starting materials fed). Then, the mixture was gradually heated to 220° C. in the presence of tin hydroxide catalyst (0.2 wt. % based on the starting materials fed) in a nitrogen atmosphere. While water generated during the reaction was removed by means of the water separator, the esterification reaction was conducted at 220° C. for 15 hours until the total acid number of the reaction mixture became 2 mgKOH/g or less. Thereafter, the reaction was continued at 220° C. under reduced pressure (20000 Pa) for about 6 hours.

After the reaction, the excess isobutanol was removed by distillation at 180° C. under a reduced pressure of 1330 Pa, and the obtained liquid residue was neutralized by adding 22 g of a 4% aqueous solution of sodium hydroxide and stirring the mixture at 80° C. for 2 hours, and then washed with water until the aqueous layer became neutral (total amount of water used: about 2000 ml) to thereby give a liquid crude ester. At this point, the crude ester had a total acid number of 0.02 mgKOH/g. Subsequently, to the ester was added activated alumina ("Tomita-AD 220P" manufactured by Tomita Pharmaceutical Co., Ltd.; 0.2 wt. % based on the starting materials fed, namely 0.22 wt. % relative to the theoretical yield of the ester), and the mixture was stirred at 90° C. and at 1330 Pa for 1 hour, and the activated alumina was filtered off, whereby 269 g of purified diisobutyl 4-cyclohexene-1,2-dicarboxylate was obtained. Dehydration was carried out at 100° C. under a reduced pressure of 1330 Pa for 6 hours.

The total acid number and kinematic viscosity of the obtained ester are shown in Table 1. The ester had a hue of 10 in terms of Hazen color number, a water content of 16 ppm, a sulfated ash content of 1 ppm, a sulfur content of less than 1 ppm, a phosphorus content of less than 1 ppm, a hydroxyl value of 0.2 mgKOH/g, a peroxide value of 0.3 meq/kg and a carbonyl value of 0.8.

Example I-2

The same procedure as in Example I-1 was carried out with the exception of using 286 g (2.2 moles) of 2-ethylhexanol having a peroxide value of 0.1 meq/kg and a carbonyl value of 0.2 and tin oxide as a catalyst (0.2 wt. % based on the starting materials fed) and conducting an esterification reaction at 230° C. for 4 hours and at 230° C. under reduced pressure (20000 Pa) for 1 hour.

Then the purification procedure of Example I-1 was followed with the exception of removing excess 2-ethylhexanol by distillation at 210° C. under a reduced pressure of 1330 Pa, whereby 376 g of purified di(2-ethylhexyl) 4-cyclohexene-1,2-dicarboxylate was produced. Dehydration was carried out at 130° C. under a reduced pressure of 1330 Pa for 5 hours.

The total acid number and kinematic viscosity of the obtained ester are shown in Table 1. The ester had a hue of 10 in terms of Hazen color number, a water content of 12 ppm, a sulfated ash content of less than 1 ppm, a sulfur content of less than 1 ppm, a phosphorus content of less than 1 ppm, a hydroxyl value of 0.8 mgKOH/g, a peroxide value of 0.2 meq/kg and a carbonyl value of 0.5.

Example I-3

Following the procedure of Example I-1, 152.1 g (1 mole) of 4-cyclohexene-1,2-dicarboxylic anhydride and 316.8 g (2.2 moles) of isononanol ("Oxocol 900", product of Kyowa Hakko Kogyo Co., Ltd.) having a peroxide value of 0.1 meq/kg and a carbonyl value of 3.0 were fed, and the mixture was gradually heated to 200° C. in the presence of tetraisopropyl titanate catalyst (0.2 wt. % based on the starting materials fed) under a nitrogen atmosphere. While the generated water was removed by water separator, esterification reaction was conducted at 200° C. for 7 hours, and at 200° C. under reduced pressure (20000 Pa) for 2 hours.

After the reaction, the excess isononanol was removed by distillation at 210° C. under a reduced pressure of 1330 Pa, and the obtained liquid residue was neutralized by adding thereto 33 g of a 4% aqueous solution of sodium hydroxide and stirring the mixture at 80° C. for 2 hours, and then washed with water until it became neutral. At this point, the crude ester had a total acid number of 0.02 mgKOH/g. Subsequently, to the ester was added activated clay ("Galleon-earth V$_1$" manufactured by Mizusawa Industrial Chemicals Ltd.; 0.2 wt. % based on the starting materials fed), and the mixture was stirred at 90° C. and at 1330 Pa for 1 hour and filtered, whereby 399 g of purified diisononyl 4-cyclohexene-1,2-dicarboxylate was obtained. Dehydration was carried out at 130° C. under a reduced pressure of 1330 Pa for 5 hours.

The total acid number and kinematic viscosity of the obtained ester are shown in Table 1. The ester had a hue of 10 in terms of Hazen color number, a water content of 20 ppm, a sulfated ash content of less than 1 ppm, a sulfur content of less than 1 ppm, a phosphorus content of less than 1 ppm, a hydroxyl value of 0.8 mgKOH/g, a peroxide value of 0.2 meq/kg and a carbonyl value of 1.2.

Example I-4

When 3,5,5-trimethylhexanol was stored at room temperature (for one year), it showed a peroxide value of 0.8 meq/kg and a carbonyl value of 17.2. To the 3,5,5-trimethylhexanol was added 70 ppm of sodium borohydride, and the mixture was stirred at 80° C. for 2 hours in a nitrogen atmosphere, followed by washing with water and dehydration. Filtration gave 3,5,5-trimethylhexanol having a peroxide value of 0.4 meq/kg and a carbonyl value of 0.3.

The same procedure as in Example I-3 was repeated with the exception of using the foregoing 3,5,5-trimethylhexanol and activated carbon (0.2 wt. % based on the starting materials used) after neutralization and washing with water, whereby purified di(3,5,5-trimethylhexyl) 4-cyclohexene-1,2-dicarboxylate was produced. Then dehydration was carried out at 130° C. under a reduced pressure of 1330 Pa for 5 hours.

The total acid number and kinematic viscosity of the obtained ester are shown in Table 1. The ester had a hue of 10 in terms of Hazen color number, a water content of 12 ppm, a sulfated ash content of 1 ppm, a sulfur content of less than 1 ppm, a phosphorus content of less than 1 ppm, a hydroxyl value of 1.1 mgKOH/g, a peroxide value of 0.6 meq/kg and a carbonyl value of 0.9.

Example I-5

When isodecanol was stored at room temperature for 8 months, it showed a peroxide value of 1.3 meq/kg and a carbonyl value of 10.7. To the isodecanol was added 70 ppm of sodium borohydride, and the mixture was stirred at 80° C. for 1 hour in a nitrogen atmosphere, followed by washing with water and dehydration. Filtration gave isodecanol having a peroxide value of 0.8 meq/kg and a carbonyl value of 0.5.

The same procedure as in Example I-2 was repeated with the exception of using the foregoing isodecanol, whereby purified diisodecyl 4-cyclohexene-1,2-dicarboxylate was produced. Then dehydration was carried out at 130° C. under a reduced pressure of 1330 Pa for 5 hours. The total acid number and kinematic viscosity of the obtained ester are shown in Table 1. The ester had a hue of 20 in terms of Hazen color number, a water content of 25 ppm, a sulfated ash content of 1 ppm, a sulfur content of less than 1 ppm, a phosphorus content of less than 1 ppm, a hydroxyl value of 0.2 mgKOH/g, a peroxide value of 0.6 meq/kg and a carbonyl value of 1.2.

Example I-6

Purified diisobutyl 1,2-cyclohexanedicarboxylate was produced following the procedure of Example I-1 with the exception of using isobutanol having a peroxide value of 0.2 meq/kg and a carbonyl value of 0.3 and 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene). Subsequently dehydration was carried out at 100° C. under a reduced pressure of 1330 Pa for 6 hours.

The total acid number and kinematic viscosity of the obtained ester are shown in Table 1. The ester had a hue of 10 in terms of Hazen color number, a water content of 23 ppm, a sulfated ash content of less than 1 ppm, a sulfur content of less than 1 ppm, a phosphorus content of less than 1 ppm, a hydroxyl value of 0.1 mgKOH/g, a peroxide value of 0.2 meq/kg and a carbonyl value of 0.1.

Example I-7

Purified di(2-ethylhexyl) 1,2-cyclohexanedicarboxylate was produced by the same procedure as in Example I-2 with the exception of using 2-ethylhexanol having a peroxide value of 0.1 meq/kg and a carbonyl value of 0.2 and 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene). Subsequently dehydration was carried out at 130° C. under a reduced pressure of 1330 Pa for 5 hours.

The total acid number and kinematic viscosity of the obtained ester are shown in Table 1. The ester had a hue of 10 in terms of Hazen color number, a water content of 10 ppm, a sulfated ash content of 1 ppm, a sulfur content of less than 1 ppm, a phosphorus content of less than 1 ppm, a hydroxyl value of 0.3 mgKOH/g, a peroxide value of 0.3 meq/kg and a carbonyl value of 0.6.

Example I-8

Purified di(3,5,5-trimethylhexyl) 1,2-cyclohexanedicarboxylate was produced by the same procedure as in Example I-7 with the exception of using 3,5,5-trimethylhexanol having a peroxide value of 0.4 meq/kg and a carbonyl value of 0.3 (the same as used in Example I-4). Subsequently dehydration was carried out at 130° C. under a reduced pressure of 1330 Pa for 5 hours.

The total acid number and kinematic viscosity of the obtained ester are shown in Table 1. The ester had a hue of 10 in terms of Hazen color number, a water content of 28 ppm, a sulfated ash content of less than 1 ppm, a sulfur content of less than 1 ppm, a phosphorus content of less than 1 ppm, a hydroxyl value of 0.9 mgKOH/g, a peroxide value of 0.5 meq/kg and a carbonyl value of 0.2.

Example I-9

When 3,5,5-trimethylhexanol was stored at room temperature for one year, it showed a peroxide value of 0.8 meq/kg and a carbonyl value of 17.2. The same procedure as in Example I-8 was performed with the exception of using said 3,5,5-trimethylhexanol, thereby producing purified di(3,5,5-trimethylhexyl) 1,2-cyclohexanedicarboxylate. Then dehydration was carried out at 130° C. under reduced pressure of 1330 Pa for 5 hours.

The total acid number and kinematic viscosity of the obtained ester are shown in Table 1. The ester had a hue of 30 in terms of Hazen color number, a water content of 23 ppm, a sulfated ash content of 4 ppm, a sulfur content of less than 1 ppm, a phosphorus content of less than 1 ppm, a hydroxyl value of 1.2 mgKOH/g, a peroxide value of 1.0 meq/kg and a carbonyl value of 9.8.

Example I-10

When 3,5,5-trimethylhexanol was stored at room temperature for one year, it showed a peroxide value of 0.8 meq/kg and a carbonyl value of 17.2. Following the procedure of Example I-8 and using the 3,5,5-trimethylhexanol, the starting materials were gradually heated to 225° C. in the presence of tin oxide catalyst (0.2 wt. % based on the starting materials fed) in a nitrogen atmosphere. While water generated during the reaction was removed by means of water separator, the esterification reaction was conducted for 6 hours and at 225° C. under reduced pressure (20000 Pa) for 2 hours.

After the reaction, excess 3,5,5-trimethylhexanol was removed by distillation at 210° C. under a reduced pressure of 1330 Pa, and the obtained liquid residue was neutralized by adding thereto 33 g of a 4% aqueous solution of sodium hydroxide and stirring the mixture at 80° C. for 2 hours, and then washed with water until the aqueous layer became neutral to thereby give a liquid crude ester. At this point, the crude ester had a total acid number of 0.01 mgKOH/g. Subsequently, to the ester was added activated alumina ("Tomita-AD 220P" manufactured by Tomita Pharmaceutical Co., Ltd.; 0.2 wt. % based on the starting materials fed) and activated clay ("Galleon-earth $V_1$" manufactured by Mizusawa Industrial Chemicals Ltd.; 0.2 wt. % based on the starting materials fed), and the mixture was stirred at 90° C. and at 1330 Pa for 1 hour and filtered, whereby 390 g of purified di(3,5,5-trimethylhexyl) 4-cyclohexene-1,2-dicarboxylate was obtained. Dehydration was carried out at 130° C. under a reduced pressure of 1330 Pa for 5 hours.

The total acid number and kinematic viscosity of the obtained ester are shown in Table 1. The ester had a hue of 30 in terms of Hazen color number, a water content of 16 ppm, a sulfated ash content of less than 1 ppm, a sulfur content of less than 1 ppm, a phosphorus content of less than 1 ppm, a hydroxyl value of 0.7 mgKOH/g, a peroxide value of 0.6 meq/kg and a carbonyl value of 4.8.

TABLE 1

Properties of esters

| Example | Ester name | Total acid number (mgKOH/g) | Kinematic viscosity (mm²/s) 40° C. | Kinematic viscosity (mm²/s) 100° C. |
|---|---|---|---|---|
| I-1 | Diisobutyl 4-cyclohexene-1,2-dicarboxylate | 0.01 | 8.2 | 2.0 |
| I-2 | Di(2-ethylhexyl) 4-cyclohexene-1,2-dicarboxylate | 0.01 | 17.4 | 3.3 |
| I-3 | Diisononyl 4-cyclohexene-1,2-dicarboxylate | 0.01 | 21.0 | 4.0 |
| I-4 | Di(3,5,5-trimethylhexyl) 4-cyclohexene-1,2-dicarboxylate | 0.01 | 29.2 | 4.8 |
| I-5 | Diisodecyl 4-cyclohexene-1,2-dicarboxylate | 0.01 | 29.4 | 4.7 |
| I-6 | Diisobutyl 1,2-cyclohexanedicarboxylate | 0.01 | 8.0 | 2.0 |
| I-7 | Di(2-ethylhexyl) 1,2-cyclohexane-dicarboxylate | 0.01 | 18.4 | 3.4 |
| I-8 | Di(3,5,5-trimethylhexyl) 1,2-cyclohexanedicarboxylate | 0.01 | 29.9 | 4.8 |
| I-9 | Di(3,5,5-trimethylhexyl) 1,2-cyclohexanedicarboxylate | 0.01 | 29.3 | 4.8 |
| I-10 | Di(3,5,5-trimethylhexyl) 1,2-cyclohexanedicarboxylate | 0.01 | 29.3 | 4.8 |

Comparative Example I-1

When isobutanol was stored at room temperature for 10 months, it showed a peroxide value of 1.3 meq/kg and a carbonyl value of 18.1. The same apparatus as used in Example I-1 was charged with 162.8 g (2.2 moles) of the isobutanol, 152.1 g (1 mole) of 4-cyclohexene-1,2-dicarboxylic anhydride (prepared by usual Diels-Alder reaction of maleic anhydride and 1,3-butadiene) and toluene (5 wt. % based on the starting materials fed). Then the mixture was heated to 150° C. in the presence of p-toluenesulfonic acid catalyst (0.4 wt. % based on the starting materials fed) in a nitrogen atmosphere. While water generated during the reaction was removed by means of water separator, the esterification reaction was conducted at 150° C. under reduced pressure (20000 Pa) for 6 hours, and the reaction was continued at 150° C. under reduced pressure (10000 Pa) for 2 hours.

After the reaction, the excess isobutanol was removed by distillation at 180° C. under a reduced pressure of 1330 Pa, and the obtained liquid residue was neutralized by adding thereto 22 g of a 4% aqueous solution of sodium hydroxide and stirring the mixture at 80° C. for 2 hours, and then washed with water until the aqueous layer became neutral, to thereby give a crude liquid ester. At this point, the crude ester had a total acid number of 0.01 mgKOH/g. Subsequently, to the ester was added activated carbon ("Shirasagi M" manufactured by Sumitomo Chemical Co., Ltd.; 0.2 wt. % based on the starting materials fed), and the mixture was stirred at 90° C. and at 1330 Pa for 1 hour and filtered, whereby 260 g of diisobutyl 4-cyclohexene-1,2-dicarboxylate was obtained. Dehydration was carried out at 100° C. under a reduced pressure of 1330 Pa for 6 hours.

The total acid number and kinematic viscosity of the obtained ester are shown in Table 2. The ester had a hue of 120 in terms of Hazen color number, a water content of 20 ppm, a sulfated ash content of less than 1 ppm, a sulfur content of 22 ppm, a phosphorus content of less than 1 ppm, a hydroxyl value of 0.5 mgKOH/g, a peroxide value of 6.4 meq/kg and a carbonyl value of 15.2.

Comparative Example I-2

Purified diisobutyl 4-cyclohexene-1,2-dicarboxylate was produced in the same manner as in Comparative Example I-i with the exception of using isobutanol having a peroxide value of 0.2 meq/kg and a carbonyl value of 0.3 (the same as used in Example I-1). Thereafter, dehydration was carried out at 100° C. under a reduced pressure of 1330 Pa for 6 hours.

The total acid number and kinematic viscosity of the obtained ester are shown in Table 2. The ester had a hue of 20 in terms of Hazen color number, a water content of 13 ppm, a sulfated ash content of less than 1 ppm, a sulfur content of 25 ppm, a phosphorus content of less than 1 ppm, a hydroxyl value of 0.3 mgKOH/g, a peroxide value of 0.2 meq/kg and a carbonyl value of 0.6.

Comparative Example I-3

When 2-ethylhexanol was stored at room temperature for one year, it showed a peroxide value of 0.7 meq/kg and a carbonyl value of 4.8. Following the procedure of Comparative Example I-1 with the exception of conducting esterification reaction using the 2-ethylhexanol in the presence of phosphoric acid catalyst (0.3 wt. % based on the starting materials fed) and removing the 2-ethylhexanol by distillation at 210° C. under reduced pressure of 1330 Pa, di(2-ethylhexyl) 4-cyclohexene-1,2-dicarboxylate was obtained. Thereafter, dehydration was carried out at 130° C. under a reduced pressure of 1330 Pa for 5 hours.

The total acid number and kinematic viscosity of the obtained ester are shown in Table 2. The ester had a hue of 100 in terms of Hazen color number, a water content of 33 ppm, a sulfated ash content of less than 1 ppm, a sulfur content of less than 1 ppm, a phosphorus content of 32 ppm, a hydroxyl value of 1.2 mgKOH/g, a peroxide value of 1.3 meq/kg and a carbonyl value of 3.9.

Comparative Example I-4

When isodecanol was stored at room temperature for one year, it showed a peroxide value of 1.8 meq/kg and a carbonyl value of 3.9. The same procedure as in Comparative Example I-1 was carried out except that esterification reaction was conducted using the isodecanol and tin oxide as a catalyst (0.2 wt. % based on the starting materials fed) at 230° C. for 4 hours and at 230° C. under reduced pressure (20000 Pa) for 1 hour. After the reaction, the procedure of Comparative Example I-1 was followed with the exception of removing excess isodecanol by distillation at 210° C. under a reduced pressure of 1330 Pa, whereby diisodecyl 4-cyclohexene-1,2-dicarboxylate was obtained. Thereafter, dehydration was carried out at 130° C. under a reduced pressure of 1330 Pa for 5 hours.

The total acid number and kinematic viscosity of the obtained ester are shown in Table 2. The ester had a hue of 70 in terms of Hazen color number, a water content of 27 ppm, a sulfated ash content of 2 ppm, a sulfur content of less than 1 ppm, a phosphorus content of less than 1 ppm, a hydroxyl value of 0.4 mgKOH/g, a peroxide value of 5.0 meq/kg and a carbonyl value of 7.6.

TABLE 2

Properties of esters

| Comparative Example | Ester name | Total acid number (mgKOH/g) | Kinematic viscosity (mm$^2$/s) 40° C. | 100° C. |
|---|---|---|---|---|
| I-1 | Diisobutyl 4-cyclohexene-1,2-dicarboxylate | 0.01 | 9.1 | 2.1 |
| I-2 | Diisobutyl 4-cyclohexene-1,2-dicarboxylate | 0.01 | 9.0 | 2.1 |
| I-3 | Di(2-ethylhexyl) 4-cyclohexene-1,2-dicarboxylate | 0.01 | 17.4 | 3.3 |
| I-4 | Diisodecyl 4-cyclohexene-1,2-dicarboxylate | 0.02 | 29.0 | 4.6 |

Test Example I-1

Electrical insulating property each of the esters of Examples I-1 to I-10 and Comparative Examples I-1 to I-4 was evaluated in terms of volume resistivity. The results are shown in Table 3.

Test Example I-2

Heat stability each of the esters of Examples I-1 to I-10 and Comparative Examples I-1 to I-4 was evaluated. The results are shown in Table 3.

Test Example I-3

Long-term hydrolysis stability each of the esters of Examples I-1 to I-10 and Comparative Examples I-1 to I-4 was evaluated. The results are shown in Table 3.

TABLE 3

| Sample | Volume resistivity (Ω·cm) | Heat stability (increased total acid number, mgKOH/g) | Long-term hydrolysis stability (increased total acid number, mgKOH/g) |
|---|---|---|---|
| Ester of Ex. I-1 | 8.6 × 10$^{11}$ | 0.53 | 0.83 |
| Ester of Ex. I-2 | 9.5 × 10$^{11}$ | 0.48 | 0.72 |
| Ester of Ex. I-3 | 4.5 × 10$^{13}$ | 0.44 | 0.77 |
| Ester of Ex. I-4 | 1.9 × 10$^{13}$ | 0.39 | 0.82 |
| Ester of Ex. I-5 | 8.9 × 10$^{13}$ | 0.70 | 0.83 |
| Ester of Ex. I-6 | 8.5 × 10$^{11}$ | 0.81 | 0.75 |
| Ester of Ex. I-7 | 8.1 × 10$^{12}$ | 0.77 | 0.68 |
| Ester of Ex. I-8 | 4.7 × 10$^{13}$ | 0.42 | 0.60 |
| Ester of Ex. I-9 | 8.2 × 10$^{12}$ | 0.88 | 0.97 |
| Ester of Ex. I-10 | 3.3 × 10$^{13}$ | 0.62 | 0.63 |
| Ester of Comp. Ex. I-1 | 3.2 × 10$^{10}$ | 3.82 | 14.82 |
| Ester of Comp. Ex. I-2 | 3.9 × 10$^{10}$ | 2.99 | 10.27 |
| Ester of Comp. Ex. I-3 | 3.1 × 10$^{10}$ | 3.16 | 7.56 |
| Ester of Comp. Ex. I-4 | 4.1 × 10$^{12}$ | 1.51 | 3.38 |

As apparent from Examples I-1 to I-8, the alicyclic dicarboxylic acid diesters prepared by the process of the present invention are excellent in hue, electrical insulating property, heat stability and hydrolysis stability so that they are suitable for use as a refrigerator oil.

On the other hand, as shown in Comparative Examples I-1 to I-4, the esters prepared by the reaction using a sulfur- or phosphorus-containing catalyst or the esters prepared using an alcohol having a peroxide value in excess of 1.0 mgKOH/g are poor in hue and high in peroxide value and carbonyl value even if neutralization and treatment with an adsorbent are sufficiently carried out. Further, the total acid numbers of these esters are considerably increased in the test for the evaluation of heat stability and hydrolysis stability, and the volume resistivity thereof is also low in the test for the evaluation of electrical insulating property.

As shown by the results of Examples I-9 and I-10, alicyclic dicarboxylic acid diesters having improved performance can be prepared by purifying the produced esters using at least two kinds of adsorbents.

The process of the present invention provides alicyclic dicarboxylic acid diesters which are excellent in electrical insulating property, heat stability and hydrolysis stability and are suited for use as a refrigerator oil.

Embodiment II of the present invention will be described in greater detail with reference to the following examples and comparative examples. The properties of lubricating oils prepared in these examples were evaluated by the following methods.

Kinematic Viscosity

Measured according to JIS-K-2283 using Ubbellohde viscometer.

Total Acid Number

Measured according to JIS-K-2501.

Water Content

Measured according to JIS-K-2275 using Karl Fischer's moisture meter (MKC-510, product of Kyoto Denshi Kabushiki Kaisha)

Sulfated Ash Content

Measured according to JIS-K-2272.5.

Sulfur Content

A sample ester (5.0 g) was diluted with hexane to give a 10.0 ml dilution, and the sulfur content of the ester was measured with a sulfur analyzer, TS-03 (product of Mitsubishi Chemical Corp.).

Phosphorus Content
  Measured according to JIS-K-0102-1998.

Hydroxyl Value
  Measured according to JIS-K-0070.

Peroxide Value
  Measured according to 2.5.2-1996 (Standard Methods for the Analysis of Fats, Oil and Related Materials (Japan Oil Chemists' Society).

Carbonyl Value
  Measured according to 2.5.4-1996 (Standard Methods for the Analysis of Fats, Oil and Related Materials (Japan Oil Chemists' Society).

Test for Electrical Insulating Property
  The volume resistivity was measured at 25° C. according to JIS-C-2101. The higher the volume resistivity is, the more excellent the electrical insulating property is.

Test for Hydrolysis Stability
  Iron wire, copper wire and aluminum wire, 1.6 mm in diameter and 4 cm in length, were placed in a glass test tube of 6.6 mm in inner diameter and 30 cm in height, and 2.0 g of an ester sample and 0.2 g of distilled water were weighed out and introduced into the test tube. The test tube was sealed while it was degassed by an aspirator. The test tube was placed in an oven and heated at 175° C. for 30 hours. Then the ester sample was taken out to measure the total acid number. It is considered that the smaller the increase in total acid number is, the higher the hydrolysis stability is. The result obtained in this test is an index of hydrolysis resistance of the ester as heated in the presence of water.

Test for Heat Stability
  Iron wire, copper wire and aluminum wire, 1.6 mm in diameter and 4 cm in length were placed in a beaker of 53 mm in inner diameter and 56 mm in height, and 40 g of an ester sample was weighed out and introduced into the beaker. The beaker was placed in an oven and heated at 175° C. for 15 hours. Then the ester sample was taken out to measure the total acid number. The smaller the increase in acid number after the test as compared with that before the test is, the higher the heat stability is. The result obtained in this test is an index of resistance of the ester to oxidative deterioration.

Analysis by Gas Chromatography
  The cis isomer/trans isomer ratio of alicyclic dicarboxylic acid diesters were determined by gas chromatography, and expressed in terms of area ratio of the obtained gas chromatogram. The proportions of the esters in the ester mixtures were also expressed in terms of area ratio of the obtained gas chromatogram. Measurement conditions and analysis conditions are as follows.

Measurement Conditions:
Instrument: Gas chromatograph GC-14B (product of Shimadzu Seisakusho)
Column used: 3.2 mm in diameter×3.1 m (made of glass)
Column adsorbent: DEGS Chromosorb WAW, liquid phase support ratio: 15%, 60/80 mesh (GL Science)
Injection temperature: 240° C.
Column temperature: 180° C.
Nitrogen stream: 40 mL/minute
Sample concentration: 5 wt. % (dilution solvent:acetone)

Analysis Conditions:
Data processing apparatus: chromatopack C—R5A (product of Shimadzu Seisakusho)

Analysis parameters: WIDTH=5
  SLOPE=70
  DRIFT=0
  MIN. AREA=1000
  T.DBL=0

Example II-1

A 4-necked flask equipped with a stirrer, a thermometer and a Dean-Stark water separator was charged with 152.1 g (1 mole) of 4-cyclohexene-1,2-dicarboxylic anhydride (prepared by usual Diels-Alder reaction of maleic anhydride and 1,3-butadiene) and 74 g (1 mole) of isobutanol as alcohol component 1. The mixture was heated to 130° C. and stirred for 1 hour in a nitrogen atmosphere. At this point, the total acid number of the reaction mixture was found to be 248 mgKOH/g (theoretical value:248 mgKOH/g).

Then tin hydroxide (0.2 wt. % based on the starting materials fed) was added thereto and the mixture was heated to 220° C. At 220° C., 156 g (1.2 moles) of 2-ethylhexanol as alcohol component 2 was added dropwise. While water generated during the reaction was removed by the water separator, the esterification reaction was carried out in a nitrogen atmosphere at 220° C. for about 6 hours until the total acid number of the reaction mixture became 3 mgKOH/g or less, and further continued at 220° C. and at 20000 Pa for 1 hour.

After the reaction, the excess alcohol was removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 311 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 23 ppm, a sulfated ash content of less than 1 ppm, a sulfur content of less than 1 ppm, a phosphorus content of less than 1 ppm, a hydroxyl value of 0.7 mgKOH/g, a peroxide value of 0.7 meq/kg and a carbonyl value of 0.2. The obtained ester mixture had a cis:trans isomer ratio of 53:47 (area %), as determined from the gas chromatogram thereof. Further, the obtained ester mixture was found to be a mixture of the following esters from the gas chromatogram thereof:

(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=14.5/54.7/30.8 (area %)

Example II-2

Following the procedure of Example II-1, 152.1 g (1 mole) of 4-cyclohexene-1,2-dicarboxylic anhydride (prepared by usual Diels-Alder reaction of maleic anhydride and 1,3-butadiene), 29.6 g (0.4 mole) of isobutanol and 78 g (0.6 mole) of 2-ethylhexanol as alcohol component 1 were subjected to esterification reaction in a 4-necked flask, whereby the total acid number of the reaction mixture became 218 mgKOH/g (theoretical value: 219 mgKOH/g).

Then, to the reaction mixture was added tin hydroxide (0.2 wt. % based on the starting materials fed) as a catalyst, and at 220° C., 156 g (1.2 moles) of 2-ethylhexanol as alcohol component 2 was further added dropwise. While the water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohol was removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 346 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 15 ppm, a sulfated ash content of 3 ppm, a sulfur content of less than 1 ppm, a phosphorus content of less than 1 ppm, a hydroxyl value of 0.4 mgKOH/g, a peroxide value of 0.2 meq/kg and a carbonyl value of 0.5. The obtained ester mixture had a cis:trans isomer ratio of 55:45 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=2.0/23.5/74.5 (area %).

Example II-3

Following the procedure of Example II-1, 152.1 g (1 mole) of 4-cyclohexene-1,2-dicarboxylic anhydride (prepared by usual Diels-Alder reaction of maleic anhydride and 1,3-butadiene) and 74 g (1.0 mole) of isobutanol as alcohol component 1 were subjected to a reaction in a four-necked flask, whereby the total acid number of the reaction mixture became 249 mgKOH/g (theoretical value: 248 mgKOH/g).

Then, to the reaction mixture was added tin hydroxide (0.2 wt. % based on the starting materials fed) as a catalyst, and at 220° C., 64.4 g (0.87 mole) of isobutanol and 42.9 g (0.33 mole) of 2-ethylhexanol as alcohol component 2 were further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 282 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 12 ppm, a sulfated ash content of 2 ppm, a sulfur content of less than 1 ppm, a phosphorus content of less than 1 ppm, a hydroxyl value of 1.1 mgKOH/g, a peroxide value of 0.6 meq/kg and a carbonyl value of 0.9. The obtained ester mixture had a cis:trans isomer ratio of 42:58 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=71.6/25.7/2.7 (area %)

Example II-4

A reaction was carried out following the procedure of Example II-1 and using 152.1 g (1 mole) of 4-cyclohexene-1,2-dicarboxylic anhydride (prepared by usual Diels-Alder reaction of maleic anhydride and 1,3-butadiene), 51.8 g (0.7 mole) of isobutanol and 43.2 g (0.3 mole) of isononanol ("Oxocol 900", product of Kyowa Hakko Kogyo. Co., Ltd.) as alcohol component 1, whereby the total acid number of the reaction mixture became 233 mgKOH/g (theoretical value: 231 mgKOH/g).

Then, to the reaction mixture was added tetraisopropyl titanate (0.3 wt. % based on the starting materials fed), and at 210° C., 172.8 g (1.2 moles) of isononanol as alcohol component 2 was further added dropwise. While water generated during the reaction was removed by water separator, the esterification reaction was carried out at 210° C. for about 6 hours until the total acid number of the reaction mixture became 3 mgKOH/g or less, and further continued at 210° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 346 g of a purified ester mixture containing (isobutyl) (isononyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 10 ppm, a sulfated ash content of less than 1 ppm, a sulfur content of less than 1 ppm, a phosphorus content of less than 1 ppm, a hydroxyl value of 0.7 mgKOH/g, a peroxide value of 0.7 meq/kg and a carbonyl value of 0.5. The obtained ester mixture had a cis:trans isomer ratio of 80:20 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(isononyl) 4-cyclohexene-1,2-dicarboxylate
(3) diisononyl 4-cyclohexene-1,2-dicarboxylate
   (1)/(2)/(3)=6.6/43.2/50.2 (area %)

Example II-5

A reaction was carried out following the procedure of Example II-1 and using 152.1 g (1 mole) of 4-cyclohexene-1,2-dicarboxylic anhydride (prepared by usual Diels-Alder reaction of maleic anhydride and 1,3-butadiene) and 74 g (1 mole) of isobutanol as alcohol component 1, whereby the total acid number of the reaction mixture became 247 mgKOH/g (theoretical value: 248 mgKOH/g).

Then, to the reaction mixture was added tin hydroxide (0.2 wt. % based on the starting materials fed) as a catalyst, and at 220° C., 7.4 g (0.1 mole) of isobutanol and 158.4 g (1.1 moles) of 3,5,5-trimethylhexanol as alcohol component 2 were further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 35 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 334 g of a purified ester mixture containing (isobutyl) (3,5,5-trimethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 28 ppm, a sulfated ash content of 1 ppm, a sulfur content of less than 1 ppm, a phosphorus content of less than 1 ppm, a hydroxyl value of 0.7 mgKOH/g, a peroxide value of 0.9 meq/kg and a carbonyl value of 1.1. The obtained ester had a cis:trans isomer ratio of 51:49 (area %), as determined from the gas chromatogram thereof. Further, the obtained ester mixture was found to be a mixture of the following esters from the gas chromatogram thereof:

(1) diisobutyl 4-cyclohexene-1,2-dicarboxylate
(2) (isobutyl) (3,5,5-trimethylhexyl) 4-cyclohexene-1,2-dicarboxylate
(3) di(3,5,5-trimethylhexyl) 4-cyclohexene-1,2-dicarboxylate
   (1)/(2)/(3)=17.9/56.1/26.0 (area %)

Example II-6

A reaction was carried out following the procedure of Example II-1 and using 154.1 g (1 mole) of 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene) and 74 g of isobutanol (1 mole) as alcohol component 1, whereby the total acid number of the reaction mixture became 247 mgKOH/g (theoretical value: 246 mgKOH/g).

Then, to the reaction mixture was added tin hydroxide (0.2 wt. % based on the starting materials fed) as a catalyst, and at 220° C., 156 g (1.2 moles) of 2-ethylhexanol as alcohol component 2 was further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 311 g of a purified ester mixture containing (isobutyl) (2-ethylhexyl) 1,2-cyclohexanedicarboxylate was obtained. Dehydration was carried out at 100° C. under a reduced pressure of 1330 Pa for 6 hours.

The total acid number and kinematic viscosity of the obtained ester mixture are shown in Table 4. The ester mixture had a water content of 12 ppm, a sulfated ash content of less than 1 ppm, a sulfur content of less than 1 ppm, a phosphorus content of less than 1 ppm, a hydroxyl value of 1.3 mgKOH/g, a peroxide value of 0.5 meq/kg and a carbonyl value of 0.6. The obtained ester had a cis trans isomer ratio of 39:61 (area %), as determined from the gas chromatogram thereof. Further the obtained ester mixture was found to be a mixture of the following esters from the gas chromatogram thereof:

(1) diisobutyl 1,2-cyclohexanedicarboxylate
(2) (isobutyl)(2-ethylhexyl) 1,2-cyclohexanedicarboxylate
(3) di(2-ethylhexyl) 1,2-cyclohexanedicarboxylate
   (1)/(2)/(3)=13.9/52.9/33.2 (area %)

TABLE 4

Properties of esters

| Example | Acid component | Alcohol component | Total acid number (mgKOH/g) | Kinematic viscosity (mm²/s) 40° C. | Kinematic viscosity (mm²/s) 100° C. |
| --- | --- | --- | --- | --- | --- |
| II-1 | 4-Cyclohexene-1,2-dicarboxylic acid | Isobutanol (45 mole %) 2-Ethylhexanol (55 mole %) | 0.01 | 13.1 | 2.7 |
| II-2 | 4-Cyclohexene-1,2-dicarboxylic acid | Isobutanol (18 mole %) 2-Ethylhexanol (82 mole %) | 0.01 | 15.2 | 3.1 |
| II-3 | 4-Cyclohexene-1,2-dicarboxylic acid | Isobutanol (85 mole %) 2-Ethylhexanol (15 mole %) | 0.01 | 9.2 | 2.2 |
| II-4 | 4-Cyclohexene-1,2-dicarboxylic acid | Isobutanol (32 mole %) Isononanol (68 mole %) | 0.01 | 16.5 | 3.3 |
| II-5 | 4-Cyclohexene-1,2-dicarboxylic acid | Isobutanol (50 mole %) 3,5,5-Trimethylhexanol (50 mole %) | 0.01 | 15.3 | 3.0 |
| II-6 | 1,2-Cyclohexane-dicarboxylic acid | Isobutanol (45 mole %) 2-Ethylhexanol (55 mole %) | 0.01 | 13.0 | 2.7 |

Comparative Example II-1

A reaction was carried out following the procedure of Example II-1 using 152.1 g (1 mole) of 4-cyclohexene-1,2-dicarboxylic anhydride (prepared by usual Diels-Alder reaction of maleic anhydride and 1,3-butadiene) and 74 g (1 mole) of isobutanol as alcohol component 1, whereby the total acid number of the reaction mixture became 248 mgKOH/g (theoretical value: 248 mgKOH/g).

Then, to the reaction mixture was added p-toluenesulfonic acid (0.4 wt. % based on the starting materials fed) as a catalyst, and at 220° C., 156 g (1.2 moles) of 2-ethylhexanol as alcohol component 2 was further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 313 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 5. The ester mixture had a water content of 12 ppm, a sulfated ash content of less than 1 ppm, a sulfur content of 28 ppm, a phosphorus content of less than 1 ppm, a hydroxyl value of 0.4 mgKOH/g, a peroxide value of 0.1 meq/kg and a carbonyl value of 0.3. The obtained ester mixture had a cis:trans isomer ratio of 46:54 (area %), as determined from the gas chromatogram thereof. Further the obtained ester mixture was found to be a mixture of the following esters from the gas chromatogram thereof:

(1) diisobutyl 4-cyclohexene-1,2-dicarboxylate (2) (isobutyl)(2-ethylhexyl) 4-cyclohexene-1,2-dicarboxylate (3) di(2-ethylhexyl) 4-cyclohexene-1,2-dicarboxylate (1)/(2)/(3)=14.2/53.9/31.9 (area %)

Comparative Example II-2

A reaction was carried out in the same apparatus as used in Comparative Example II-1 and using 152.1 g (1 mole) of 4-cyclohexene-1,2-dicarboxylic anhydride (prepared by usual Diels-Alder reaction of maleic anhydride and 1,3-butadiene), 74 g (1 mole) of isobutanol and 156 g (1.2 moles) of 2-ethylhexanol. Then the mixture was gradually heated to 210° C. in the presence of tetraisopropyl titanate (0.2 wt. % based on the starting materials fed) to undergo esterification reaction for 26 hours. More specifically, while water generated during the reaction was removed by means of the water separator, the esterification reaction was conducted at 210° C. for about 22 hours until the total acid number of the reaction mixture became 3 mgKOH/g or less. Thereafter, the reaction was continued at 210° C. and at 20000 Pa for about 4 hours. The reaction mixture was worked up (evaporation of excess alcohols, neutralization, washing with water and treatment with adsorbent) in the same manner as in comparative Example II-1 to give 302 g of purified ester mixture containing (isobutyl) (2-ethylhexyl) 4-cyclohexene-1,2-dicarboxylate. Dehydration was carried out at 100° C. under a reduced pressure of 1330 Pa for 6 hours.

The total acid number and kinematic viscosity of the obtained ester mixture are shown in Table 5. The ester mixture had a water content of 22 ppm, a sulfated ash content of 2 ppm, a sulfur content of less than 1 ppm, a phosphorus content of less than 1 ppm, a hydroxyl value of 0.8 mgKOH/g, a peroxide value of 3.1 meq/kg and a carbonyl value of 2.6. The obtained ester mixture had a cis:trans isomer ratio of 78:22 (area %), as determined from the gas chromatogram thereof. Further, the obtained ester mixture was found to be a mixture of the following esters from the gas chromatogram thereof:

(1) diisobutyl 4-cyclohexene-1,2-dicarboxylate (2) (isobutyl) (2-ethylhexyl) 4-cyclohexene-1,2-dicarboxylate (3) di(2-ethylhexyl) 4-cyclohexene-1,2-dicarboxylate (1)/(2)/(3)=13.6/54.1/32.3 (area %)

TABLE 5

Properties of esters

| Comp. Ex. | Acid component | Alcohol component | Total acid number (mgKOH/g) | Kinematic viscosity (mm²/s) 40° C. | Kinematic viscosity (mm²/s) 100° C. |
|---|---|---|---|---|---|
| II-1 | 4-Cyclohexene-1,2-dicarboxylic acid | Isobutanol (45 mole %) 2-Ethylhexanol (55 mole %) | 0.01 | 13.3 | 2.7 |
| II-2 | 4-Cyclohexene-1,2-dicarboxylic acid | Isobutanol (45 mole %) 2-Ethylhexanol (55 mole %) | 0.01 | 13.4 | 2.7 |

Example II-7

A 4-necked flask equipped with a stirrer, a thermometer and a Dean-Stark water separator was charged with 152.1 g (1 mole) of 4-cyclohexene-1,2-dicarboxylic anhydride (prepared by usual Diels-Alder reaction of maleic anhydride and 1,3-butadiene) and 29.6 g (0.4 mole) of isobutanol having a peroxide value of 0.1 meq/kg and a carbonyl value of 0.1 and 78 g (0.6 mole) of 2-ethylhexanol having a peroxide value of 0.2 meq/kg and a carbonyl value of 0.1 as alcohol component 1. The mixture was heated to 130° C. and stirred for 1 hour in a nitrogen atmosphere. At this point, the total acid number of the reaction mixture was found to be 248 mgKOH/g (theoretical value:248 mgKOH/g).

Then tin hydroxide (0.2 wt. % based on the starting materials fed) was added thereto and the mixture was heated to 220° C. At 220° C., 156 g (1.2 moles) of 2-ethylhexanol having a peroxide value of 0.2 meq/kg and a carbonyl value of 0.1 as alcohol component 2 was further added dropwise. While water generated during the reaction was removed by the water separator, the esterification reaction was carried out at 220° C. for about 6 hours in a nitrogen atmosphere, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 314 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours. The total acid number and kinematic viscosity of the obtained ester mixture are shown in Table 6. The ester mixture had a water content of 14 ppm, a sulfated ash content of less than 1 ppm, a sulfur content of less than 1 ppm, a phosphorus content of less than 1 ppm, a hydroxyl value of 0.3 mgKOH/g, a peroxide value of 0.2 meq/kg and a carbonyl value of 0.2. The obtained ester mixture had a cis:trans isomer ratio of 48:52 (area %), as determined from the gas chromatogram thereof. Further the obtained ester mixture was found to be a mixture of the following esters from the gas chromatogram thereof:

(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=15.0/52.6/32.4 (area %)

Example II-8

The same procedure as in Example II-2 was conducted with the exception of using isobutanol with a peroxide value of 0.1 meq/kg and a carbonyl value of 0.1 and 2-ethylhexanol with a peroxide value of 0.2 meq/kg and a carbonyl value of 0.1 as alcohol component 1 and using 2-ethylhexanol with a peroxide value of 0.2 meg/kg and a carbonyl value of 0.1 as alcohol component 2 and tin oxide (0.2 wt. % based on the starting materials fed) as a catalyst, and using, after the neutralization and washing with water, activated carbon ("Shirasagi M" manufactured by Sumitomo Chemical Co., Ltd.; 0.1 wt. % based on the starting materials fed), activated clay ("Galleon earth $V_1$" manufactured by Mizusawa Industrial Chemicals Ltd.; 0.1 wt. % based on the starting materials fed) and synthetic hydrotalcite ("Kyoward 600" manufactured by Kyowa Kagaku Kogyo Kabushiki Kaisha; 0.2 wt. % based on the starting materials fed), whereby a purified ester mixture containing (isobutyl) (2-ethylhexyl) 4-cyclohexene-1,2-dicarboxylate was produced. Dehydration was carried out at 100° C. under a reduced pressure of 1330 Pa for 6 hours.

The total acid number and kinematic viscosity of the obtained ester mixture are shown in Table 6. The ester mixture had a water content of 12 ppm, a sulfated ash content of less than 1 ppm, a sulfur content of less than 1 ppm, a phosphorus content of less than 1 ppm, a hydroxyl value of 0.5 mgKOH/g, a peroxide value of 0.1 meq/kg and a carbonyl value of 0.4. The obtained ester mixture had a cis:trans isomer ratio of 56:44 (area %), as determined from the gas chromatogram thereof. Further the obtained ester mixture was found to be a mixture of the following esters from the gas chromatogram thereof:

(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=1.9/25.1/73.0 (area %)

Example II-9

The same procedure as in Example II-3 was conducted with the exception of using isobutanol with a peroxide value of 0.1 meq/kg and a carbonyl value of 0.1 as alcohol component 1 and isobutanol with a peroxide value of 0.1 meq/kg and a carboxyl value of 0.1 and 2-ethylhexanol with a peroxide value of 0.2 meq/kg and a carbonyl value of 0.1 as alcohol component 2 and tin oxide (0.2 wt. % based on the starting materials fed) as a catalyst, whereby a purified ester mixture containing (isobutyl) (2-ethylhexyl) 4-cyclohexene-1,2-dicarboxylate was produced. Dehydration was carried out at 100° C. under a reduced pressure of 1330 Pa for 6 hours.

The total acid number and kinematic viscosity of the obtained ester mixture are shown in Table 6. The ester mixture had a water content of 22 ppm, a sulfated ash content of less than 1 ppm, a sulfur content of less than 1 ppm, a phosphorus content of less than 1 ppm, a hydroxyl value of 1.0 mgKOH/g, a peroxide value of 0.1 meq/kg and a carbonyl value of 0.2. The obtained ester mixture had a cis:trans isomer ratio of 50:50 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=71.9/24.7/3.4 (area %)

Example II-10

Following the procedure of Example II-1, 152.1 g (1 mole) of 4-cyclohexene-1,2-dicarboxylic anhydride (prepared by usual Diels-Alder reaction of maleic anhydride and 1,3-butadiene) was reacted with 74 g (1.0 mole) of isobutanol with a peroxide value of 0.1 meq/kg and a carbonyl value of 0.1 as alcohol component 1 in a four-necked flask, whereby the total acid number of the reaction mixture became 248 mgKOH/g (theoretical value: 248 mgKOH/g).

Then, to the reaction mixture was added tin oxide (0.2 wt. % based on the starting materials fed), and at 220° C. 7.4 g (0.1 mole) of said isobutanol and 143 g (1.1 moles) of 2-ethylhexanol with a peroxide value of 0.2 meq/kg and a carbonyl value of 0.1 as alcohol component 2 were further added dropwise. While water generated during the reaction was removed by water separator, the esterification reaction was carried out at 200° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 305 g of a purified ester mixture containing (isobutyl) (2-ethylhexyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 16 ppm, a sulfated ash content of less than 1 ppm, a sulfur content of less than 1 ppm, a phosphorus content of less than 1 ppm, a hydroxyl value of 0.3 mgKOH/g, a peroxide value of 0.5 meq/kg and a carbonyl value of 0.6. The obtained ester mixture had a cis:trans isomer ratio of 48:52 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(2-ethylhexyl) 4-cyclohexene-1,2-dicarboxylate
(3) di(2-ethylhexyl) 4-cyclohexene-1,2-dicarboxylate
(1)/(2)/(3)=19.7/43.8/36.5 (area %)

Example II-11

The same procedure as in Example II-4 was conducted with the exception of using isobutanol with a peroxide value of 0.1 meq/kg and a carbonyl value of 0.1 and isononanol with a peroxide value of 0.2 meq/kg and a carbonyl value of 0.3 as alcohol component 1 and using isononanol with a peroxide value of 0.2 meq/kg and a carbonyl value of 0.3 as alcohol component 2 and using tin oxide (0.2 wt. % based on the starting materials fed) as a catalyst, whereby a purified ester mixture containing (isobutyl) (isononyl) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 20 ppm, a sulfated ash content of less than 1 ppm, a sulfur content of less than 1 ppm, a phosphorus content of less than 1 ppm, a hydroxyl value of 0.7 mgKOH/g, a peroxide value of 0.4 meq/kg and a carbonyl value of 0.1. The obtained ester mixture had a cis:trans isomer ratio of 78:22 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(isononyl) 4-cyclohexene-1,2-dicarboxylate
(3) di(isononyl) 4-cyclohexene-1,2-dicarboxylate
(1)/(2)/(3)=6.6/42.9/50.5 (area %)

Example II-12

The same procedure as in Example II-5 was conducted with the exception of using isobutanol with a peroxide value of 0.1 meq/kg and a carbonyl value of 0.1 as alcohol component 1, isobutanol with a peroxide value of 0.1 meq/kg and a carbonyl value of 0.1 and 3,5,5-trimethylhexanol with a peroxide value of 0.1 meq/kg and a carbonyl value of 0.2 as alcohol component 2, and tin oxide (0.2 wt. % based on the starting materials fed) as a catalyst, whereby a purified ester mixture containing (isobutyl) (3,5,5-trimethylhexyl) 4-cyclohexene-1,2-dicarboxylate was produced. Dehydration was carried out at 100° C. under a reduced pressure of 1330 Pa for 6 hours.

The total acid number and kinematic viscosity of the obtained ester mixture are shown in Table 6. The ester mixture had a water content of 13 ppm, a sulfated ash content of less than 1 ppm, a sulfur content of less than 1 ppm, a phosphorus content of less than 1 ppm, a hydroxyl value of 0.4 mgKOH/g, a peroxide value of 0.2 meq/kg and a carbonyl value of 0.2. The obtained ester mixture had a cis:trans isomer ratio of 57:43 (area %), as determined from the gas chromatogram thereof. Further the obtained ester mixture was found to be a mixture of the following esters from the gas chromatogram thereof:
(1) diisobutyl 4-cyclohexene-1,2-dicarboxylate
(2) (isobutyl)(3,5,5-trimethylhexyl) 4-cyclohexene-1,2-dicarboxylate (3) di(3,5,5-trimethylhexyl) 4-cyclohexene-1,2-dicarboxylate
(1)/(2)/(3)=18.0/52.2/29.8 (area %)

Example II-13

Following the procedure of Example II-12, a reaction as carried out using 152.1 g (1 mole) of 4-cyclohexene-1,2-dicarboxylic anhydride (prepared by usual Diels-Alder reaction of maleic anhydride and 1,3-butadiene), 32.6 g (0.44 mole) of isobutanol with a peroxide value of 0.1 meq/kg and a carbonyl value of 0.1 and 80.6 g (0.56 mole) of 3,5,5-trimethylhexanol with a peroxide value of 0.1 meq/kg and a carbonyl value of 0.2 as alcohol component 1, whereby the total acid number of the reaction mixture became 217 mgKOH/g (theoretical value: 214 mgKOH/g).

Then, to the reaction mixture was added tin oxide (0.2 wt. % based on the starting materials fed), and at 220° C., 172.8 g (1.2 moles) of 3,5,5-trimethylhexanol with a peroxide value of 0.1 meq/kg and a carbonyl value of 0.2 as alcohol component 2 was further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 33 g of a 4% aqueous solution of sodium hydroxide and stirring the mixture at. 80° C. for 2 hours, and then washed with water until it became neutral, giving a crude ester mixture. At this point, the crude ester mixture 0.5 had a total acid number of 0.01 mgKOH/g. Subsequently, to the crude ester mixture was added activated carbon (hirasagi M manufactured by Sumitomo Chemical Co., Ltd.; 0.1 wt. % based on the starting materials fed), and the mixture was stirred at 90° C. and at 1330 Pa for 1 hour and filtered, whereby 383 g of a purified ester mixture containing (isobutyl) (3,5,5-trimethylhexanol) 4-cyclohexene-1,2-dicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 19 ppm, a sulfated ash content of less than 1 ppm, a sulfur content of less than 1 ppm, a phosphorus content of less than 1 ppm, a hydroxyl value of 0.7 mgKOH/g, a peroxide value of 0.2 meq/kg and a carbonyl value of 0.2. The obtained ester mixture had a cis:trans isomer ratio of 56:44 (area %), as determined from the gas chromatogram thereof. Further, the obtained ester mixture was found to be a mixture of the following esters from the gas chromatogram thereof:
(1) diisobutyl 4-cyclohexene-1,2-dicarboxylate
(2) (isobutyl)(3,5,5-trimethylhexyl) 4-cyclohexene-1,2-dicarboxylate
(3) di(3,5,5-trimethylhexyl)4-cyclohexene-1,2-dicarboxylate
(1)/(2)/(3)=2.3/28.0/69.7 (area %)

Example II-14

The same procedure as in Example II-6 was conducted with the exception of using isobutanol with a peroxide value of 0.1 meq/kg and a carbonyl value of 0.1 as alcohol component 1,2-ethylhexanol with a peroxide value of 0.2 meq/kg and a carbonyl value of 0.1 as alcohol component 2, giving a purified ester mixture containing (isobutyl)(2-ethylhexyl) 1,2-cyclohexanedicarboxylate. Dehydration was carried out at 100° C. under a reduced pressure of 1330 Pa for 6 hours.

The total acid number and kinematic viscosity of the obtained ester mixture are shown in Table 6. The ester mixture had a water content of 17 ppm, a sulfated ash content of less than 1 ppm, a sulfur content of less than 1 ppm, a phosphorus content of less than 1 ppm, a hydroxyl value of 0.8 mgKOH/g, a peroxide value of 0.1 meq/kg and a carbonyl value of 0.3. The obtained ester mixture had a cis:trans isomer ratio of 38:62 (area %), as determined from the gas chromatogram thereof. Further, the obtained ester mixture was found to be a mixture of the following esters from the gas chromatogram thereof:
(1) diisobutyl 1,2-cyclohexanedicarboxylate
(2) (isobutyl)(2-ethylhexyl) 1,2-cyclohexanedicarboxylate
(3) di(2-ethylhexyl) 1,2-cyclohexanedicarboxylate
(1)/(2)/(3)=14.1/52.6/33.3 (area %)

Example II-15

In the same manner as in Example II-6, a reaction was conducted using 154.1 g (1 mole) of 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene) and 74 g (1 mole) of isobutanol with a peroxide value of 0.1 meq/kg and a carbonyl value of 0.1 as alcohol component 1, whereby the total acid number of the reaction mixture became 248 mgKOH/g (theoretical value: 246 mgKOH/g).

Then, to the reaction mixture was added tin oxide (0.2 wt. % based on the starting materials fed), and at 220° C., 7.4 g (0.1 mole) of isobutanol with a peroxide value of 0.1 meq/kg and a carbonyl value of 0.1 and 143 g (1.1 moles) of 2-ethylhexanol with a peroxide value of 0.2 meq/kg and a carbonyl value of 0.1 as alcohol component 2 was further added dropwise. While water generated during the reaction was removed by water separator, the esterification reaction was carried out at 220° C. for about 9 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 308 g of a purified ester mixture containing (isobutyl) (2-ethylhexyl) 1,2-cyclohexanedicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 26 ppm, a sulfated ash content of less than 1 ppm, a sulfur content of less than 1 ppm, a phosphorus content of less than 1 ppm, a hydroxyl value of 0.9 mgKOH/g, a peroxide value of 0.4 meq/kg and a carbonyl value of 0.4.

The obtained ester mixture had a cis:trans isomer ratio of 30:70 (area %), as determined from the gas chromatogram thereof. Further, the obtained ester mixture was found to be a mixture of the following esters from the gas chromatogram thereof:

(1) diisobutyl 1,2-cyclohexanedicarboxylate
(2) (isobutyl)(2-ethylhexyl) 1,2-cyclohexanedicarboxylate
(3) di(2-ethylhexyl) 1,2-cyclohexanedicarboxylate
    (1)/(2)/(3)=20.4/43.6/36.0 (area %)

Example II-16

In the same manner as in Example II-15, a reaction was conducted using 154.1 g (1 mole) of 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene) and 74 g (1 mole) of isobutanol with a peroxide value of 0.1 meq/kg and a carbonyl value of 0.1 as alcohol component 1, whereby the total acid number of the reaction mixture became 246 mgKOH/g (theoretical value: 246 mgKOH/g).

Then, to the reaction mixture was added tin oxide (0.2 wt. % based on the starting materials fed), and at 220° C., 56.2 g (0.76 mole) of said isobutanol and 57.2 g (0.44 mole) of 2-ethylhexanol with a peroxide value of 0.2 meq/kg and a carbonyl value of 0.1 as alcohol component 2 were further added dropwise. While water generated during the reaction was removed by water separator, the esterification reaction was carried out at 220° C. for about 9 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 308 g of a purified ester mixture containing (isobutyl) (2-ethylhexyl) 1,2-cyclohexanedicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 13 ppm, a sulfated ash content of 1 ppm, a sulfur content of less than 1 ppm, a phosphorus content of less than 1 ppm, a hydroxyl value of 1.0 mgKOH/g, a peroxide value of 0.2 meq/kg and a carbonyl value of 0.1. The obtained ester mixture had a cis:trans isomer ratio of 28:72 (area %), as determined from the gas chromatogram thereof. Further, the obtained ester mixture was found to be a mixture of the following esters from the gas chromatogram thereof:

(1) diisobutyl 1,2-cyclohexanedicarboxylate
(2) (isobutyl) (2-ethylhexyl) 1,2-cyclohexanedicarboxylate
(3) di(2-ethylhexyl) 1,2-cyclohexanedicarboxylate
    (1)/(2)/(3)=60.7/33.4/5.9 (area %)

Example II-17

In the same manner as in Example II-15, a reaction was carried out using 154.1 g (1 mole) of 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene) and 74 g (1 mole) of n-butanol with a peroxide value of 0.2 meq/kg and a carbonyl value of 0.1 as alcohol component 1, whereby the total acid number of the reaction mixture became 246 mgKOH/g (theoretical value: 246 mgKOH/g).

Then, to the reaction mixture was added tin oxide (0.2 wt. % based on the starting materials fed) as a catalyst as a catalyst, and at 220° C., 7.4 g (0.1 mole) of said n-butanol and 173.8 g (1.1 moles) of isodecanol with a peroxide value of 0.1 meq/kg and a carbonyl value of 0.3 as alcohol component 2 were further added dropwise. While water generated during the reaction was removed by water separator, the esterification reaction was carried out at 220° C. for about 9 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 317 g of a purified ester mixture containing (n-butyl)(isodecyl) 1,2-cyclohexanedicarboxylate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 15 ppm, a sulfated ash content of less than 1 ppm, a sulfur content of less than 1 ppm, a phosphorus content of less than 1 ppm, a hydroxyl value of 0.5 mgKOH/g, a peroxide value of 0.3 meq/kg and a carbonyl value of 0.4. The obtained ester mixture had a cis:trans isomer ratio of 48:52 (area %), as determined from the gas chromatogram thereof. Further, the obtained ester mixture was found to be a mixture of the following esters from the gas chromatogram thereof:

(1) di(n-butyl) 1,2-cyclohexanedicarboxylate
(2) (n-butyl)(isodecyl) 1,2-cyclohexanedicarboxylate
(3) diisodecyl 1,2-cyclohexanedicarboxylate
    (1)/(2)/(3)=19.7/46.8/32.5 (area %)

Example II-18

In the same manner as in Example II-15, a reaction was carried out using 154.1 g (1 mole) of 1,2-cyclohexanedicarboxylic anhydride (prepared by hydrogenating 4-cyclohexene-1,2-dicarboxylic anhydride obtained by usual Diels-Alder reaction of maleic anhydride and 1,3-butadiene) and 74 g (1 mole) of isobutanol with a peroxide value of 0.1 meq/kg and a carbonyl value of 0.1 as alcohol component 1, whereby the total acid number of the reaction mixture became 246 mgKOH/g (theoretical value: 246 mgKOH/g).

Then, to the reaction mixture was added tin oxide (0.2 wt. % based on the starting materials fed) as a catalyst, and at 220° C., 7.4 g (0.1 mole) of said isobutanol and 158.4 g (1.1 moles) of 3,5,5-trimethylhexanol with a peroxide value of 0.1 meq/kg and a carbonyl value of 0.2 as alcohol component 2 were further added dropwise. While water generated during the reaction was removed by water separator, the esterification reaction was carried out at 220° C. for about 9 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 320 g of a purified ester mixture containing (isobutyl)(3,5,5-trimethylhexyl) 1,2-cyclohexanedicarboxylate was obtained. Dehydration was carried out at 100° C. under a reduced pressure of 1330 Pa for 6 hours. The total acid number and kinematic viscosity of the obtained ester are shown in Table 6.

The ester mixture had a water content of 12 ppm, a sulfated ash content of less than 1 ppm, a sulfur content of less than 1 ppm, a phosphorus content of less than 1 ppm, a hydroxyl value of 0.2 mgKOH/g, a peroxide value of 0.1 meq/kg and a carbonyl value of 0.2. The obtained ester mixture had a cis:trans isomer ratio of 38:62 (area %), as determined from the gas chromatogram thereof. Further, the obtained ester mixture was found to be a mixture of the following esters from the gas chromatogram thereof:

(1) diisobutyl 1,2-cyclohexanedicarboxylate
(2) (isobutyl)(3,5,5-trimethylhexyl) 1,2-cyclohexanedicarboxylate
(3) di(3,5,5-trimethylhexyl) 1,2-cyclohexanedicarboxylate
(1)/(2)/(3)=21.9/44.2/33.9 (area %)

Example II-19

In the same manner as in Example II-15, 148 g (1 mole) of phthalic anhydride was reacted with 74 g (1 mole) of isobutanol with a peroxide value of 0.1 meq/kg and a carbonyl value of 0.1 as alcohol component 1, whereby the total acid number of the reaction mixture became 254 mgKOH/g (theoretical value: 252 mgKOH/g).

Then, to the reaction mixture was added tin oxide (0.2 wt. % based on the starting materials fed) as a catalyst, and at 220° C., 7.4 g (0.1 mole) of said isobutanol and 143 g (1.1 moles) of 2-ethylhexanol with a peroxide value of 0.2 meq/kg and a carbonyl value of 0.1 as alcohol component 2 were further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 27 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g. Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 320 g of a purified ester mixture containing (isobutyl) (2-ethylhexyl)phthalate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 25 ppm, a sulfated ash content of less than 1 ppm, a sulfur content of less than 1 ppm, a phosphorus content of less than 1 ppm, a hydroxyl value of 0.2 mgKOH/g, a peroxide value of 0.1 meq/kg and a carbonyl value of 0.1. The obtained ester mixture was found to be a mixture of the following esters from the gas chromatogram thereof:

(1) diisobutyl phthalate
(2) (isobutyl) (2-ethylhexyl)phthalate
(3) di(2-ethylhexyl)phthalate
(1)/(2)/(3)=21.1/40.8/38.1 (area %)

Example II-20

In the same manner as in Example II-15, 148 g (1 mole) of phthalic anhydride was reacted with 74 g (1 mole) of isobutanol with a peroxide value of 0.1 meq/kg and a carbonyl value of 0.1 as alcohol component 1, whereby the total acid number of the reaction mixture became 252 mgKOH/g (theoretical value: 252 mgKOH/g).

Then, to the reaction mixture was added tin oxide (0.2 wt. % based on the starting materials fed) as a catalyst, and at 220° C., 7.4 g (0.1 mole) of said isobutanol and 158.4 g (1.1 moles) of 3,5,5-trimethylhexanol with a peroxide value of 0.1 meq/kg and a carbonyl value of 0.2 as alcohol component 2 were further added dropwise. While water generated during the reaction was removed by water separator, the esterification reaction was carried out at 220° C. for about 6 hours until the total acid number of the reaction mixture became 3 mgKOH/g or less, and further continued at 220° C. and at 20000 Pa for 1 hour.

After the reaction, the excess alcohols were removed by distillation at 180° C. under a reduced pressure of 1330 Pa, and the obtained liquid residue was neutralized by adding thereto 30 g of a 4% aqueous solution of sodium hydroxide and stirring the mixture at 80° C. for 2 hours, and then washed with water until it became neutral, giving a crude ester mixture. At this point, the crude ester mixture had a total acid number of 0.01 mgKOH/g.

Subsequently, to the crude ester mixture was added activated carbon ("Shirasagi M" manufactured by Sumitomo Chemical Co., Ltd.; 0.1 wt. % based on the starting materials fed), and the mixture was stirred at 90° C. and at 1330 Pa for 1 hour and filtered, whereby 329 g of a purified ester mixture containing (isobutyl) (3,5,5-trimethylhexyl)phthalate was obtained. Dehydration was carried out at 100° C. under a reduced pressure of 1330 Pa for 6 hours.

The total acid number and kinematic viscosity of the obtained ester mixture are shown in Table 6. The ester mixture had a water content of 11 ppm, a sulfated ash content of less than 1 ppm, a sulfur content of less than 1 ppm, a phosphorus content of less than 1 ppm, a hydroxyl value of 1.4 mgKOH/g, a peroxide value of 0.2 meq/kg and a carbonyl value of 0.2. The obtained ester mixture was found to be a mixture of the following esters from the gas chromatogram thereof:

(1) diisobutyl phthalate
(2) (isobutyl)(3,5,5-trimethylhexyl)phthalate
(3) di(3,5,5-trimethylhexyl)phthalate
(1)/(2)/(3)=21.9/44.2/33.9 (area %)

TABLE 6

Properties of esters

| Ex. | Acid component | Alcohol component | Total acid number | Kinematic viscosity 40° C. | Kinematic viscosity 100° C. |
|---|---|---|---|---|---|
| II-7 | 4-Cyclohexene-1,2-dicarboxylic acid | Isobutanol (45 mole %)/2-Ethylhexanol (55 mole %) | 0.01 | 13.0 | 2.7 |
| II-8 | 4-Cyclohexene-1,2-dicarboxylic acid | Isobutanol (18 mole %)/2-Ethylhexanol (82 mole %) | 0.01 | 15.2 | 3.1 |
| II-9 | 4-Cyclohexene-1,2-dicarboxylic acid | Isobutanol (85 mole %)/2-Ethylhexanol (15 mole %) | 0.01 | 9.3 | 2.2 |
| II-10 | 4-Cyclohexene-1,2-dicarboxylic acid | Isobutanol (50 mole %)/2-Ethylhexanol (50 mole %) | 0.01 | 12.0 | 2.6 |
| II-11 | 4-Cyclohexene-1,2-dicarboxylic acid | Isobutanol (32 mole %)/Isononanol (68 mole %) | 0.01 | 16.5 | 3.3 |
| II-12 | 4-Cyclohexene-1,2-dicarboxylic acid | Isobutanol (50 mole %)/3,5,5-Trimethylhexanol (50 mole %) | 0.01 | 16.0 | 3.1 |
| II-13 | 4-Cyclohexene-1,2-dicarboxylic acid | Isobutanol (20 mole %)/3,5,5-trimethylhexanol (80 mole %) | 0.01 | 22.6 | 4.0 |
| II-14 | 1,2-Cyclohexane-dicarboxylic acid | Isobutanol (45 mole %)/2-Ethylhexanol (55 mole %) | 0.01 | 12.9 | 2.7 |
| II-15 | 1,2-Cyclohexane-dicarboxylic acid | Isobutanol (50 mole %)/2-Ethylhexanol (50 mole %) | 0.01 | 12.7 | 2.6 |
| II-16 | 1,2-Cyclohexane-dicarboxylic acid | Isobutanol (80 mole %)/2-Ethylhexanol (20 mole %) | 0.01 | 10.1 | 2.3 |
| II-17 | 1,2-Cyclohexane-dicarboxylic acid | n-Butanol (50 mole %)/Isodecanol (50 mole %) | 0.01 | 12.5 | 2.8 |
| II-18 | 1,2-Cyclohexane-dicarboxylic acid | Isobutanol (50 mole %)/3,5,5-trimethylhexanol (50 mole %) | 0.01 | 17.3 | 3.3 |
| II-19 | Phthalic acid | Isobutanol (50 mole %)/2-Ethylhexanol (50 mole %) | 0.01 | 20.3 | 3.4 |
| II-20 | Phthalic acid | Isobutanol (50 mole %)/3,5,5-trimethylhexanol (50 mole %) | 0.01 | 25.0 | 4.0 |

*Total acid number: mgKOH/g
*Kinematic viscosity: mm$^2$/s

Test Example II-1

The hydrolysis stability was evaluated with respect to the ester mixtures of Examples II-1 to II-20 and Comparative Examples II-1 and II-2. The results are shown in Table 7.

Test Example II-2

The heat stability was evaluated with respect to the ester mixtures of Examples II-1 to II-20 and Comparative Examples II-1 and II-2. The results are shown in Table 7.

Test Example II-3

The electrical insulating property was evaluated in terms of volume resistivity with respect to the ester mixtures of Examples II-1 to II-20 and Comparative Examples II-1 and II-2. The results are shown in Table 7.

TABLE 7

Hydrolysis stability, Heat stability and Electrical insulating property

| Sample | Hydrolysis stability Total acid number after test (mgKOH/g) | Heat stability Total acid number after test (mgKOH/g) | Volume resistivity (Ω · cm) |
|---|---|---|---|
| Ester of Ex. II-1 | 0.70 | 0.69 | 2.6 × 10$^{12}$ |
| Ester of Ex. II-2 | 0.66 | 0.65 | 4.0 × 10$^{12}$ |
| Ester of Ex. II-3 | 0.81 | 0.65 | 1.0 × 10$^{12}$ |
| Ester of Ex. II-4 | 0.75 | 0.68 | 2.5 × 10$^{12}$ |
| Ester of Ex. II-5 | 0.82 | 0.60 | 5.3 × 10$^{12}$ |
| Ester of Ex. II-6 | 0.66 | 0.81 | 2.0 × 10$^{12}$ |
| Ester of Comp. Ex. II-1 | 3.15 | 2.15 | 4.0 × 10$^{11}$ |
| Ester of Comp. Ex. II-2 | 1.84 | 1.88 | 7.3 × 10$^{11}$ |
| Ester of Ex. II-7 | 0.26 | 0.45 | 8.6 × 10$^{12}$ |
| Ester of Ex. II-8 | 0.25 | 0.49 | 3.0 × 10$^{13}$ |
| Ester of Ex. II-9 | 0.33 | 0.42 | 6.3 × 10$^{12}$ |
| Ester of Ex. II-10 | 0.30 | 0.51 | 9.0 × 10$^{12}$ |
| Ester of Ex. II-11 | 0.36 | 0.45 | 8.3 × 10$^{12}$ |
| Ester of Ex. II-12 | 0.35 | 0.48 | 3.0 × 10$^{13}$ |
| Ester of Ex. II-13 | 0.39 | 0.57 | 3.6 × 10$^{13}$ |
| Ester of Ex. II-14 | 0.28 | 0.62 | 1.7 × 10$^{13}$ |
| Ester of Ex. II-15 | 0.31 | 0.73 | 9.7 × 10$^{12}$ |
| Ester of Ex. II-16 | 0.37 | 0.80 | 6.9 × 10$^{12}$ |
| Ester of Ex. II-17 | 0.64 | 0.85 | 7.0 × 10$^{12}$ |
| Ester of Ex. II-18 | 0.38 | 0.77 | 2.0 × 10$^{13}$ |
| Ester of Ex. II-19 | 0.88 | 0.33 | 1.4 × 10$^{12}$ |
| Ester of Ex. II-20 | 0.98 | 0.27 | 4.0 × 10$^{12}$ |

As apparent from Examples II-1 to II-6, the alicyclic adjacent dicarboxylic acid mixed diesters prepared by the process of the present invention are excellent in hydrolysis stability, heat stability and electrical insulating property.

On the other hand, the alicyclic adjacent dicarboxylic acid mixed diesters prepared by one-step process as described in Comparative Examples II-1 and II-2 are poor in hydrolysis stability and heat stability, since they exhibit a great increase in total acid number, and are also low in volume resistivity. Esters prepared by using a sulfur-containing catalyst are also inferior in these properties.

Furthermore, Examples II-7 to II-20 demonstrate that the alicyclic or aromatic adjacent dicarboxylic acid mixed diesters prepared by using an alcohol low in peroxide value and carbonyl value display notably high hydrolysis stability and heat stability, and are more excellent as a refrigerator oil.

The invention claimed is:

1. An ester selected from the group consisting of alicyclic dicarboxylic acid diesters represented by the formula (E)

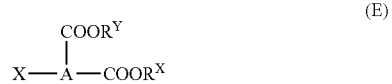

(E)

wherein A represents a cyclohexane ring or a cyclohexene ring, X is a hydrogen atom or methyl, $R^X$ and $R^Y$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, the ester having the following properties:
  1) a total acid number of 0.05 mgKOH/g or less,
  2) a sulfated ash content of 10 ppm or less,
  3) a sulfur content of 20 ppm or less,
  4) a phosphorus content of 20 ppm or less,
  5) a peroxide value of 1.0 meq/kg or less,
  6) a carbonyl value of 10 or less,
  7) a volume resistivity of $1\times10^{11}$ Ω·cm or more,
  8) a hydroxyl value of 3 mgKOH/g or less, and
  9) a water content of 100 ppm or less.

2. An ester selected from the group consisting of (I) alicyclic dicarboxylic acid diesters represented by the formula (1)

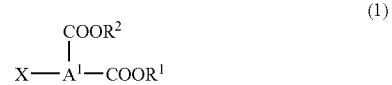

(1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms; and
  (II) alicyclic adjacent dicarboxylic acid mixed diesters represented by the formula (4)

(4)

wherein A represents a cyclohexane ring or a cyclohexene ring, X is a hydrogen atom or methyl, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, and the group —$COOR^5$ and the group —$COOR^6$ are attached to two adjacent carbon atoms of the cyclohexane ring or cyclohexene ring represented by A, the ester having the following properties:
  1) a total acid number of 0.05 mgKOH/g or less,
  2) a sulfated ash content of 10 ppm or less,
  3) a sulfur content of 20 ppm or less,
  4) a phosphorus content of 20 ppm or less,
  5) a peroxide value of 1.0 meq/kg or less,
  6) a carbonyl value of 10 or less,
  7) a volume resistivity of $1\times10^{11}$ Ω·cm or more,
  8) a hydroxyl value of 3 mgKOH/g or less, and
  9) a water content of 100 ppm or less.

3. An alicyclic dicarboxylic acid diester represented by the formula (1)

(1)

wherein $A^1$ represents a cyclohexane ring or cyclohexene ring, X is a hydrogen atom or methyl, $R^1$ and $R^2$ are the same or different and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms; the alicyclic dicarboxylic acid diester having the following properties:
  1) a total acid number of 0.05 mgKOH/g or less,
  2) a sulfated ash content of 10 ppm or less,
  3) a sulfur content of 20 ppm or less,
  4) a phosphorus content of 20 ppm or less,
  5) a peroxide value of 1.0 meq/kg or less,
  6) a carbonyl value of 10 or less,
  7) a volume resistivity of $1\times10^{11}$ Ω·cm or more,
  8) a hydroxyl value of 3 mgKOH/g or less, and
  9) a water content of 100 ppm or less.

4. The alicyclic dicarboxylic acid diester according to claim 3 wherein $A^1$ is a cyclohexane ring and X is a hydrogen atom, or $A^1$ is a cyclohexene ring and X is a hydrogen atom, or $A^1$ is a cyclohexene ring and X is methyl, and the two ester groups —$COOR^1$ and —$COOR^2$ are attached to 1- and 2-positions of the cyclohexane ring or cyclohexene ring represented by $A^1$.

5. The alicyclic dicarboxylic acid diester according to claim 4 wherein $R^1$ and $R^2$ are the same and each represents straight-chain or branched-chain alkyl group having 3 to 11 carbon atoms, $A^1$ is a cyclohexane ring or cyclohexene ring and X is a hydrogen atom.

6. An alicyclic adjacent dicarboxylic acid mixed diester represented by the formula (4)

(4)

wherein A represents a cyclohexane ring or a cyclohexene ring, X is a hydrogen atom or methyl, $R^5$ and $R^6$ are different from each other and each is a branched-chain alkyl group having 3 to 18 carbon atoms, a straight-chain alkyl group having 1 to 18 carbon atoms, a straight-chain alkenyl group having 2 to 18 carbon atoms or a cycloalkyl group having 3 to 10 carbon atoms, and the group —COOR$^5$ and the group —COOR$^6$ are attached to two adjacent carbon atoms of the cyclohexane ring or cyclohexene ring represented by A; and having the following properties:

1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1 \times 10^{11}$ Ω·cm or more,
8) a hydroxyl value of 3 mgKOH/g or less, and
9) a water content of 100 ppm or less.

7. An alicyclic adjacent dicarboxylic acid mixed diester according to claim 6 wherein X is a hydrogen atom, R$^5$ is a straight-chain alkyl group having 1 to 5 carbon atoms or a branched-chain alkyl group having 3 to 5 carbon atoms, and R$^6$ is a straight-chain or branched chain alkyl group having 6 to 11 carbon atoms, and when A is a cyclohexene ring, the group —COOR$^5$ and group —COOR$^6$ are present at the 1- and 2-positions and the double bond is present between the 4- and 5-positions.

8. An ester mixture of
(1) an alicyclic adjacent dicarboxylic acid di(lower alkyl) ester represented by the formula (7)

(7)

wherein A represents a cyclohexane ring or a cyclohexene ring, X is a hydrogen atom or methyl and R$^{5a}$ is a branched-chain alkyl group having 3 to 5 carbon atoms, a straight-chain alkyl group having 1 to 5 carbon atoms, a straight-chain alkenyl group having 2 to 5 carbon atoms or a cycloalkyl group having 3 to 5 carbon atoms, and the two —COOR$^{5a}$ groups are the same and attached to two adjacent carbon atoms of the cyclohexane ring or cyclohexene ring represented by A;

(2) an alicyclic adjacent dicarboxylic acid mixed diester represented by the formula (4a)

(4a)

wherein A and X are as defined in the formula (7), and R$^{5a}$ and R$^{6a}$ are different from each other and R$^{5a}$ is as defined in the formula (7), and R$^{6a}$ is a branched-chain alkyl group having 6 to 18 carbon atoms, a straight-chain alkyl group having 6 to 18 carbon atoms, a straight-chain alkenyl group having 6 to 18 carbon atoms or a cycloalkyl group having 6 to 10 carbon atoms, and the group —COOR$^{5a}$ and the group —COOR$^{6a}$ are attached to two adjacent carbon atoms of the cyclohexane ring or cyclohexene ring represented by A, and (3) an alicyclic adjacent dicarboxylic acid di(higher alkyl) ester represented by the formula (8)

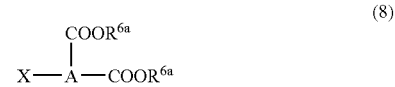

(8)

wherein A, X and R$^{6a}$ are as defined in the formula (4a), and the two —COOR$^{6a}$ groups are the same and attached to two adjacent carbon atoms of the cyclohexane ring or cyclohexene ring represented by A, the ester mixture having the following properties:

1) a total acid number of 0.05 mgKOH/g or less,
2) a sulfated ash content of 10 ppm or less,
3) a sulfur content of 20 ppm or less,
4) a phosphorus content of 20 ppm or less,
5) a peroxide value of 1.0 meq/kg or less,
6) a carbonyl value of 10 or less,
7) a volume resistivity of $1 \times 10^{11}$ Ω·cm or more,
8) a hydroxyl value of 3 mgKOH/g or less, and
9) a water content of 100 ppm or less.

9. The ester mixture according to claim 8 wherein the alicyclic adjacent dicarboxylic acid mixed diester represented by the formula (4a) under (2) is present in a proportion of 100, the alicyclic adjacent dicarboxylic acid di(lower alkyl) ester represented by the formula (7) under (1) is present in a proportion of 5-300, and the alicyclic adjacent dicarboxylic acid di(higher alkyl) ester under (3) is present in a proportion of 7-500, wherein the proportions are expressed in terms of area ratio as determined from a gas chromatogram of the ester mixture.

10. The ester mixture according to claim 8 wherein the ester mixture is a mixture of an alicyclic adjacent dicarboxylic acid di(lower alkyl) ester represented by the formula (7), an alicyclic adjacent dicarboxylic acid mixed diester represented by the formula (4a) and an alicyclic adjacent dicarboxylic acid di(higher alkyl) ester represented by the formula (8), the ester mixture having a trans isomer/cis isomer ratio of 0/100 to 80/20 (by area % as determined by gas chromatography).

* * * * *